US010048277B2

(12) United States Patent
Takeuchi

(10) Patent No.: US 10,048,277 B2
(45) Date of Patent: Aug. 14, 2018

(54) METHOD FOR DETECTING AN FGFR3/TACC3 FUSION PROTEIN, OR ENCODING GENE THEREOF

(71) Applicant: JAPANESE FOUNDATION FOR CANCER RESEARCH, Tokyo (JP)

(72) Inventor: Kengo Takeuchi, Tokyo (JP)

(73) Assignee: JAPANESE FOUNDATION FOR CANCER RESEARCH, Tokyo (JP)

(*) Notice: Subject to any disclaimer, the term of this patent is extended or adjusted under 35 U.S.C. 154(b) by 0 days.

(21) Appl. No.: 15/113,599

(22) PCT Filed: Jan. 23, 2015

(86) PCT No.: PCT/JP2015/051892
§ 371 (c)(1),
(2) Date: Jul. 22, 2016

(87) PCT Pub. No.: WO2015/111716
PCT Pub. Date: Jul. 30, 2015

(65) Prior Publication Data
US 2017/0010275 A1    Jan. 12, 2017

(30) Foreign Application Priority Data
Jan. 24, 2014 (JP) ................................ 2014-011819

(51) Int. Cl.
| | |
|---|---|
| *G01N 33/68* | (2006.01) |
| *G01N 33/574* | (2006.01) |
| *A61K 31/713* | (2006.01) |
| *C12Q 1/6886* | (2018.01) |
| *G01N 33/50* | (2006.01) |
| *G01N 33/74* | (2006.01) |

(52) U.S. Cl.
CPC ......... *G01N 33/689* (2013.01); *A61K 31/713* (2013.01); *C12Q 1/6886* (2013.01); *G01N 33/5011* (2013.01); *G01N 33/5023* (2013.01); *G01N 33/574* (2013.01); *G01N 33/57407* (2013.01); *G01N 33/74* (2013.01); *C12Q 2600/158* (2013.01); *G01N 2333/71* (2013.01); *G01N 2333/82* (2013.01)

(58) Field of Classification Search
CPC .......... G01N 33/5011; G01N 33/5023; G01N 33/574; G01N 33/57407; G01N 33/689; G01N 33/71; G01N 33/74; G01N 2333/82; C12Q 1/6886; C12Q 2600/158; A61K 31/713
See application file for complete search history.

(56) References Cited

U.S. PATENT DOCUMENTS 9,481,911 B2 * 11/2016 Suzuki ................ C12Q 1/6886
2013/0102006 A1    4/2013 Takeuchi et al.
2015/0031703 A1    1/2015 Suzuki et al.
2015/0111888 A1    4/2015 Yao et al.
2016/0009785 A1 *  1/2016 Lipson .................. C07K 14/47
                                                514/211.08

FOREIGN PATENT DOCUMENTS

| | | |
|---|---|---|
| EP | 1914240 A1 | 4/2008 |
| JP | 4303303 B2 | 7/2009 |
| JP | 2012-5479 A | 1/2012 |
| WO | 2011/162295 A1 | 12/2011 |
| WO | 2013/165008 A1 | 11/2013 |
| WO | 2013/133351 A1 | 7/2015 |
| WO | 2016/048833 A2 | 3/2016 |

OTHER PUBLICATIONS

Wu et al., "Somatic mutations of fibroblast growth factor receptor 3 (FGFR3) are uncommon in carcinomas of the uterine cervix" Oncogene, 2000, vol. 19, pp. 5543-5546.
Cappellen et al. "Frequent activating mutations of FGFR3 in human bladder and cervix carcinomas" Nature Genetics, 1999, vol. 23, pp. 18-20.
Tyler et al. "VX-680 Inhibits Aurora A and Aurora B Kinase Activity in Human Cells" Cell Cycle, 2007, vol. 6, Issue 22, pp. 2846-2854.
Babic et al. "Multiple functions of a glioblastoma fusion oncogene" Journal of Clinical Investigation, 2013, vol. 123, No. 2, pp. 548-551.
Lugo et al. "Tyrosine kinase activity and transformation potency of bcr-abl oncogene products" Science, Mar. 2, 1990; 247(4946), pp. 1079-1082.
Singh et al. "Transforming fusions of FGFR and TACC genes in human glioblastoma" Science, Sep. 7, 2012, 337 (6099):1231-35.
Williams et al. "Oncogenic FGFR3 gene fusions in bladder cancer" Human Molecular Genetics, 2013, vol. 22, No. 4, pp. 795-803.
Majewski et al. "Identification of recurrent FGFR3 fusion genes in lung cancer through kinome-centred RNA sequencing" Journal of Pathology, Jul. 2013, 230(3), pp. 270-276.
International Search Report for International Application No. PCT/JP2015/051892, dated Apr. 14, 2015.
Supplementary Partial European Search Report for corresponding European Application 15740164.7, dated Oct. 10, 2017.

* cited by examiner

*Primary Examiner* — Robert S Landsman
(74) *Attorney, Agent, or Firm* — Helsin Rothenberg Farley and Mesiti, PC

(57) ABSTRACT

A polynucleotide, which is a novel causative gene for cancer, is elucidated, and, based on this finding, provided are a method for detecting the polynucleotide, or a polypeptide encoded by the polynucleotide; a kit and a primer set for the detection; a method for screening an inhibitor of the polypeptide; and a pharmaceutical composition for treating a cancer containing the inhibitor. In the detection method of the present invention, an FGFR3 fusion protein, or a fusion gene encoding the fusion protein, or a TACC3 fusion protein, or a fusion gene encoding the fusion protein, is detected in a sample derived from female genitalia obtained from a subject.

6 Claims, No Drawings

US 10,048,277 B2

METHOD FOR DETECTING AN FGFR3/TACC3 FUSION PROTEIN, OR ENCODING GENE THEREOF

CROSS-REFERENCE TO RELATED APPLICATIONS

This application is a national phase filing under 35 U.S.C. § 371 of PCT International Application No. PCT/JP2015/051892, filed on Jan. 23, 2015, which claims priority to Japanese Application No. 2014-011819, filed Jan. 24, 2014, the contents of which are hereby incorporated by reference in their entirety into the present application.

SEQUENCE LISTING

The instant application contains a Sequence Listing, which was updated on Jul. 21, 2016; the file, in ASCII format, is designated 2352068_SequenceListing_ST25.txt and is 83.6 kilobytes in size. The file is hereby incorporated by reference in its entirety into the instant application.

TECHNICAL FIELD

The present invention relates to a fusion protein comprising an FGFR3 kinase region, or a fusion gene encoding the fusion protein, and a method for detecting the same.

The present invention relates to a novel fusion protein comprising at least a portion of a TACC3 protein, or a fusion gene encoding the fusion protein, and a method for detecting the same.

BACKGROUND ART

As a result of chromosomal translocation, originally separate genes fuse into a fusion gene. It is known that fusion genes containing part of a kinase gene, such as a BCR-ABL1 fusion in chronic myelogenous leukemia, an EML4-ALK fusion in lung cancer, and an ROS1 fusion in a variety of cancers including lung cancer, often play an essential role in carcinogenesis, and that drugs which inhibit the function become an extremely effective anti-cancer agent (Non-patent literature 1, and Patent literatures 1 and 2).

Nowadays, the relationship between molecular diagnosis and therapeutic effects on cancer is being shown clinically by the appearance of, for example, tyrosine kinase inhibitors Iressa and Tarceva. As a result, the concept of drug administration to eligible patients stratified by molecular diagnosis is spreading.

With respect to a FGFR3 (Fibroblast Growth Factor Receptor 3)-TACC3 (Transforming, Acidic Coiled-coil Containing protein 3) fusion, its presence was reported in glioblastoma (Non-patent literature 2), bladder cancer (Patent literature 3 and Non-patent literature 3), and lung cancer (Patent literature 3 and Non-patent literature 4), but there has been no report in female genital cancer. There has been no report that a kinase domain of FGFR3 can be part of a fusion (i.e., the presence of a fusion containing the kinase domain of FGFR3), and TACC3 can be part of a fusion (i.e., the presence of a fusion containing at least a portion of TACC3) in female genital cancer.

CITATION LIST

Patent Literature

[Patent literature 1] Japanese Patent No. 4303303
[Patent literature 2] WO 2011/162295
[Patent literature 3] WO 2013/133351

Non-Patent Literature

[Non-patent literature 1] Lugo T G, Pendergast A M, Muller A J, Witte O N. Tyrosine kinase activity and transformation potency of bcr-abl oncogene products. Science. 1990 Mar. 2; 247(4946): 1079-1082
[Non-patent literature 2] Singh D et al. Transforming fusions of FGFR and TACC genes in human glioblastoma. Science. 2012 Sep. 7; 337(6099): 1231-1235.
[Non-patent literature 3] Williams S V et al. Oncogenic FGFR3 gene fusions in bladder cancer. Hum Mol Genet. 2013 Feb. 15; 22(4): 795-803.
[Non-patent literature 4] Majewski I J. Identification of recurrent FGFR3 fusion genes in lung cancer through kinome-centred RNA sequencing. J Pathol. 2013 July; 230(3): 270-276.

SUMMARY OF INVENTION

Technical Problem

An object of the present invention is to elucidate a fusion (a fusion protein and a fusion gene), which is a novel causative factor for cancer, and, based on this finding, to provide a method for detecting the fusion protein, or the fusion gene encoding the fusion protein; a method for diagnosing a cancer using the detection method; a method for determining an application target for a pharmaceutical composition for treating a cancer; a kit and a primer set for the detection method; a method for screening an inhibitor of the activity and/or the expression of a polypeptide, which is the fusion protein; and a pharmaceutical composition for treating a cancer containing the inhibitor, and a method for treating a cancer by administering the pharmaceutical composition for treating the cancer.

Solution to Problem

The inventors of the present invention confirmed the fusion of part of a TACC3 gene and part of an FGFR3 gene, which was a kinase, in a specimen obtained from a patient with cervical cancer (Example 2), and found that these fusion genes were present in specimens from a plurality of patients with cervical cancer (Examples 3 and 4).

From these findings, the inventors of the present invention provides a method for detecting an FGFR3 fusion protein, or a fusion gene encoding the fusion protein; and provides a kit and a primer set for the detection method; and make it possible to select cancer patients to be treated with an FGFR3 inhibitor by detecting the fusion protein, or the fusion gene encoding the fusion protein; and provides a method for treating a cancer, comprising the step of administrating an FGFR3 inhibitor to a cancer patient.

From these findings, the inventors of the present invention provides a method for detecting a TACC3 fusion protein, or a fusion gene encoding the fusion protein; and provides a kit and a primer set for the detection method; and make it possible to select cancer patients to be treated with a TACC3 inhibitor by detecting the fusion protein, or the fusion gene encoding the fusion protein; and provides a method for treating a cancer, comprising the step of administrating a TACC3 inhibitor to the cancer patients.

The present invention relates to the following inventions:

[1] An FGFR3 fusion protein.

[2] A fusion protein of an FGFR3 protein and a TACC3 protein.

[3] The fusion protein of [1], which is selected from the group consisting of the following (a) to (f):
(a) a polypeptide consisting of the amino acid sequence of SEQ ID NO: 2,
(b) a polypeptide consisting of the amino acid sequence of SEQ ID NO: 4,
(c) a polypeptide consisting of the amino acid sequence of SEQ ID NO: 6,
(d) a polypeptide with oncogenic potential comprising the amino acid sequence of SEQ ID NO: 2, SEQ ID NO: 4, or SEQ ID NO: 6,
(e) a polypeptide with oncogenic potential comprising an amino acid sequence that has at least 80% identity to the amino acid sequence of SEQ ID NO: 2, SEQ ID NO: 4, or SEQ ID NO: 6, and
(f) a polypeptide with oncogenic potential comprising an amino acid sequence in which one or several amino acids are deleted, substituted, and/or inserted in the amino acid sequence of SEQ ID NO: 2, SEQ ID NO: 4, or SEQ ID NO: 6.

[4] A polynucleotide encoding the fusion protein of any one of [1] to [3].

[5] A vector comprising the polynucleotide of [4].

[6] A cell transformed with the vector of [5].

[7] A method for detecting an FGFR3 fusion protein, or a fusion gene encoding the fusion protein in a sample obtained from a subject.

[8] The method of [7], comprising a step of detecting the cleavage of an FGFR3 protein, or the cleavage of a gene encoding the FGFR3 protein.

[9] The method of [7], comprising a step of detecting the presence of a fusion protein constructed from an FGFR3 protein and a protein other than the FGFR3 protein, or the presence of a fusion gene encoding the fusion protein.

[10] The method of any one of [7] to [9], wherein the fusion protein is a fusion protein of an FGFR3 protein and a TACC3 protein.

[11] The method of any one of [7] to [10], wherein the fusion protein is a polypeptide selected from the group consisting of the following (a) to (f):
(a) a polypeptide consisting of the amino acid sequence of SEQ ID NO: 2,
(b) a polypeptide consisting of the amino acid sequence of SEQ ID NO: 4,
(c) a polypeptide consisting of the amino acid sequence of SEQ ID NO: 6,
(d) a polypeptide with oncogenic potential comprising the amino acid sequence of SEQ ID NO: 2, SEQ ID NO: 4, or SEQ ID NO: 6,
(e) a polypeptide with oncogenic potential comprising an amino acid sequence that has at least 80% identity to the amino acid sequence of SEQ ID NO: 2, SEQ ID NO: 4, or SEQ ID NO: 6, and
(f) a polypeptide with oncogenic potential comprising an amino acid sequence in which one or several amino acids are deleted, substituted, and/or inserted in the amino acid sequence of SEQ ID NO: 2, SEQ ID NO: 4, or SEQ ID NO: 6.

[12] The method of any one of [7] to [11], wherein the FGFR3 fusion gene is a polynucleotide encoding the polypeptide described in [3].

[13] The method of any one of [7] to [12], wherein the fusion gene is DNA or mRNA.

[14] The method of any one of [7] to [13], wherein the sample is derived from female genitalia.

[15] The method of [14], wherein the female genitalia are the uterus, vagina, or vulva.

[16] The method of [14], wherein the female genitalia are the cervix of the uterus, the vagina, or the vulva.

[17] The method of [14], wherein the female genitalia are the cervix of the uterus.

[18] A kit for detecting an FGFR3 fusion gene, comprising one probe capable of specifically recognizing a genomic region at the 5' terminus of an FGFR3 gene, and another probe capable of specifically recognizing a genomic region at the 3' terminus of the FGFR3 gene.

[19] A kit for detecting an FGFR3 fusion gene, comprising one probe capable of specifically recognizing a genomic region at the 3' terminus of a gene that constitutes an FGFR3 fusion gene together with an FGFR3 gene, and another probe capable of specifically recognizing a genomic region at the 5' terminus of the FGFR3 gene.

[20] A kit for detecting an FGFR3 fusion gene, comprising a sense primer and an antisense primer designed so as to specifically amplify a region at the 5' terminus of a polynucleotide encoding an FGFR3 protein, and a sense primer and an antisense primer designed so as to specifically amplify a region at the 3' terminus of the polynucleotide.

[21] A kit for detecting an FGFR3-TACC3 fusion gene, comprising a sense primer and an antisense primer designed so as to specifically amplify a polynucleotide encoding a polypeptide, which is a fusion protein of an FGFR3 protein and a TACC3 protein.

[22] A kit for detecting an FGFR3-TACC3 fusion gene, comprising a sense primer and an antisense primer designed so as to specifically amplify a polynucleotide encoding a polypeptide selected from the group consisting of the following (a) to (f):
(a) a polypeptide consisting of the amino acid sequence of SEQ ID NO: 2,
(b) a polypeptide consisting of the amino acid sequence of SEQ ID NO: 4,
(c) a polypeptide consisting of the amino acid sequence of SEQ ID NO: 6,
(d) a polypeptide with oncogenic potential comprising the amino acid sequence of SEQ ID NO: 2, SEQ ID NO: 4, or SEQ ID NO: 6,
(e) a polypeptide with oncogenic potential comprising an amino acid sequence that has at least 80% identity to the amino acid sequence of SEQ ID NO: 2, SEQ ID NO: 4, or SEQ ID NO: 6, and
(f) a polypeptide with oncogenic potential comprising an amino acid sequence in which one or several amino acids are deleted, substituted, and/or inserted in the amino acid sequence of SEQ ID NO: 2, SEQ ID NO: 4, or SEQ ID NO: 6.

[23] A kit for detecting an FGFR3 fusion protein, comprising an anti-FGFR3 antibody capable of specifically recognizing an N-terminal region of an FGFR3 protein, and an anti-FGFR3 antibody capable of specifically recognizing a C-terminal region of the FGFR3 protein.

[24] A kit for detecting an FGFR3 fusion protein, comprising an antibody which specifically binds to a polypeptide of a C-terminal region of a protein which constitutes an FGFR3 fusion protein together with an FGFR3 protein, and an antibody which specifically binds to a polypeptide of an N-terminal region of the FGFR3 protein.

[25] The kit of [24], wherein the protein which constitutes an FGFR3 fusion protein together with an FGFR3 protein is a TACC3 protein.

[26] A primer set for detecting a fusion gene of an FGFR3 gene and a TACC3 gene, comprising a sense primer designed from a polynucleotide portion encoding an FGFR3 protein, and an anti sense primer designed from a polynucleotide portion encoding a TACC3 protein, wherein the antisense primer consists of a nucleic acid molecule which anneals to the polynucleotide described in [22] under stringent conditions, and the sense primer consists of a nucleic acid molecule which anneals to a complementary strand to the polynucleotide described in [22] under stringent conditions.

[27] A primer set for detecting a fusion gene of an FGFR3 gene and a TACC3 gene, comprising an antisense primer consisting of a nucleic acid molecule which anneals to a polynucleotide consisting of the nucleotide sequence of SEQ ID NO: 1, SEQ ID NO: 3, or SEQ ID NO: 5 under stringent conditions, and a sense primer consisting of a nucleic acid molecule which anneals to a complementary strand to the polynucleotide under stringent conditions.

[28] A primer set comprising a sense primer and an antisense primer selected from the group consisting of the following (a) to (c):
(a) a sense primer, which is an oligonucleotide consisting of at least 16 consecutive nucleotides in the region of nucleotides 1-2628 of SEQ ID NO: 1, and an antisense primer, which is an oligonucleotide complementary to an oligonucleotide consisting of at least 16 consecutive nucleotides in the region of nucleotides 2635-5004 of SEQ ID NO: 1,
(b) a sense primer, which is an oligonucleotide consisting of at least 16 consecutive nucleotides in the region of nucleotides 1-2628 of SEQ ID NO: 3, and an antisense primer, which is an oligonucleotide complementary to an oligonucleotide consisting of at least 16 consecutive nucleotides in the region of nucleotides 2635-3561 of SEQ ID NO: 3, and
(c) a sense primer, which is an oligonucleotide consisting of at least 16 consecutive nucleotides in the region of nucleotides 1-2536 of SEQ ID NO: 5, and an antisense primer, which is an oligonucleotide complementary to an oligonucleotide consisting of at least 16 consecutive nucleotides in the region of nucleotides 2537-3270 of SEQ ID NO: 5.

[29] A method for screening a substance which inhibits the activity and/or the expression of the polypeptide described in [3], the method comprising:
(1) bringing a test substance into contact with the polypeptide, or a cell expressing the polypeptide,
(2) analyzing whether or not the activity and/or the expression of the polypeptide is inhibited, and
(3) selecting a substance which inhibits the activity and/or the expression of the polypeptide.

[30] The method of [29], wherein the substance which inhibits the activity and/or the expression of the polypeptide is a therapeutic agent for an FGFR3 fusion-positive cancer.

[31] The method of [29] or [30], wherein the cancer is a female genital cancer.

[32] The method of [29] or [30], wherein the cancer is a uterine cancer, a vaginal cancer, or a vulvar cancer.

[33] The method of [29] or [30], wherein the cancer is a cervical cancer, a vaginal cancer, or a vulvar cancer.

[34] The method of [29] or [30], wherein the cancer is a cervical cancer.

[35] A pharmaceutical composition for treating an FGFR3 fusion-positive cancer, comprising a substance which inhibits the activity and/or the expression of an FGFR3 fusion protein.

[36] The pharmaceutical composition of [35], wherein the substance which inhibits the activity and/or the expression of an FGFR3 fusion protein is a kinase inhibitor.

[37] The pharmaceutical composition of [35] or [36], wherein the FGFR3 fusion protein is the polypeptide described in [3].

[38] The pharmaceutical composition of any one of [35] to [37], wherein the cancer is a female genital cancer.

[39] The pharmaceutical composition of any one of [35] to [37], wherein the cancer is a uterine cancer, a vaginal cancer, or a vulvar cancer.

[40] The pharmaceutical composition of any one of [35] to [37], wherein the cancer is a cervical cancer, a vaginal cancer, or a vulvar cancer.

[41] The pharmaceutical composition of any one of [35] to [37], wherein the cancer is a cervical cancer.

[42] A TACC3 fusion protein.

[43] A fusion protein of an FGFR3 protein and a TACC3 protein.

[44] The fusion protein of [42], which is selected from the group consisting of the following (a) to (f):
(a) a polypeptide consisting of the amino acid sequence of SEQ ID NO: 2,
(b) a polypeptide consisting of the amino acid sequence of SEQ ID NO: 4,
(c) a polypeptide consisting of the amino acid sequence of SEQ ID NO: 6,
(d) a polypeptide with oncogenic potential comprising the amino acid sequence of SEQ ID NO: 2, SEQ ID NO: 4, or SEQ ID NO: 6,
(e) a polypeptide with oncogenic potential comprising an amino acid sequence that has at least 80% identity to the amino acid sequence of SEQ ID NO: 2, SEQ ID NO: 4, or SEQ ID NO: 6, and
(f) a polypeptide with oncogenic potential comprising an amino acid sequence in which one or several amino acids are deleted, substituted, and/or inserted in the amino acid sequence of SEQ ID NO: 2, SEQ ID NO: 4, or SEQ ID NO: 6.

[45] A polynucleotide encoding the fusion protein of any one of [42] to [44].

[46] A vector comprising the polynucleotide of [45].

[47] A cell transformed with the vector of [46].

[48] A method for detecting a TACC3 fusion protein, or a fusion gene encoding the fusion protein in a sample obtained from a subject.

[49] The method of [48], comprising a step of detecting the cleavage of a TACC3 protein, or the cleavage of a gene encoding the TACC3 protein.

[50] The method of [48], comprising a step of detecting the presence of a fusion protein constructed from a TACC3 protein and a protein other than the TACC3 protein, or the presence of a fusion gene encoding the fusion protein.

[51] The method of any one of [48] to [50], wherein the fusion protein is a fusion protein of an FGFR3 protein and a TACC3 protein.

[52] The method of any one of [48] to [51], wherein the fusion protein is a polypeptide selected from the group consisting of the following (a) to (f):
(a) a polypeptide consisting of the amino acid sequence of SEQ ID NO: 2,
(b) a polypeptide consisting of the amino acid sequence of SEQ ID NO: 4,
(c) a polypeptide consisting of the amino acid sequence of SEQ ID NO: 6, (d) a polypeptide with oncogenic potential comprising the amino acid sequence of SEQ ID NO: 2, SEQ ID NO: 4, or SEQ ID NO: 6,
(e) a polypeptide with oncogenic potential comprising an amino acid sequence that has at least 80% identity to the amino acid sequence of SEQ ID NO: 2, SEQ ID NO: 4, or SEQ ID NO: 6, and
(f) a polypeptide with oncogenic potential comprising an amino acid sequence in which one or several amino acids are deleted, substituted, and/or inserted in the amino acid sequence of SEQ ID NO: 2, SEQ ID NO: 4, or SEQ ID NO: 6.

[53] The method of any one of [48] to [52], wherein the FGFR3 fusion gene is a polynucleotide encoding the polypeptide described in [44].

[54] The method of any one of [48] to [53], wherein the fusion gene is DNA or mRNA.

[55] The method of any one of [48] to [54], wherein the sample is derived from female genitalia.

[56] The method of [55], wherein the female genitalia are the uterus, vagina, or vulva.

[57] The method of [55], wherein the female genitalia are the cervix of the uterus, the vagina, or the vulva.

[58] The method of [55], wherein the female genitalia are the cervix of the uterus.

[59] A kit for detecting a TACC3 fusion gene, comprising one probe capable of specifically recognizing a genomic region at the 5' terminus of a TACC3 gene, and another probe capable of specifically recognizing a genomic region at the 3' terminus of the TACC3 gene.

[60] A kit for detecting a TACC3 fusion gene, comprising one probe capable of specifically recognizing a genomic region at the 5' terminus of a gene that constitutes a TACC3 fusion gene together with a TACC3 gene, and another probe capable of specifically recognizing a genomic region at the 3' terminus of the TACC3 gene.

[61] A kit for detecting a TACC3 fusion gene, comprising a sense primer and an antisense primer designed so as to specifically amplify a region at the 5' terminus of a polynucleotide encoding a TACC3 protein, and a sense primer and an anti sense primer designed so as to specifically amplify a region at the 3' terminus of the polynucleotide.

[62] A kit for detecting an FGFR3-TACC3 fusion gene, comprising a sense primer and an antisense primer designed so as to specifically amplify a polynucleotide encoding a polypeptide, which is a fusion protein of an FGFR3 protein and a TACC3 protein.

[63] A kit for detecting an FGFR3-TACC3 fusion gene, comprising a sense primer and an antisense primer designed so as to specifically amplify a polynucleotide encoding a polypeptide selected from the group consisting of the following (a) to (f):
(a) a polypeptide consisting of the amino acid sequence of SEQ ID NO: 2,
(b) a polypeptide consisting of the amino acid sequence of SEQ ID NO: 4,
(c) a polypeptide consisting of the amino acid sequence of SEQ ID NO: 6,
(d) a polypeptide with oncogenic potential comprising the amino acid sequence of SEQ ID NO: 2, SEQ ID NO: 4, or SEQ ID NO: 6,
(e) a polypeptide with oncogenic potential comprising an amino acid sequence that has at least 80% identity to the amino acid sequence of SEQ ID NO: 2, SEQ ID NO: 4, or SEQ ID NO: 6, and
(f) a polypeptide with oncogenic potential comprising an amino acid sequence in which one or several amino acids are deleted, substituted, and/or inserted in the amino acid sequence of SEQ ID NO: 2, SEQ ID NO: 4, or SEQ ID NO: 6.

[64] A kit for detecting a TACC3 fusion protein, comprising an anti-TACC3 antibody capable of specifically recognizing an N-terminal region of a TACC3 protein, and an anti-TACC3 antibody capable of specifically recognizing a C-terminal region of the TACC3 protein.

[65] A kit for detecting a TACC3 fusion protein, comprising an antibody which specifically binds to a polypeptide of a N-terminal region of a protein which constitutes a TACC3 fusion protein together with a TACC3 protein, and an antibody which specifically binds to a polypeptide of an C-terminal region of the TACC3 protein.

[66] The kit of [65], wherein the protein which constitutes a TACC3 fusion protein together with a TACC3 protein is an FGFR3 protein.

[67] A primer set for detecting a fusion gene of an FGFR3 gene and a TACC3 gene, comprising a sense primer designed from a polynucleotide portion encoding an FGFR3 protein, and an anti sense primer designed from a polynucleotide portion encoding a TACC3 protein, wherein the antisense primer consists of a nucleic acid molecule which anneals to the polynucleotide described in [63] under stringent conditions, and the sense primer consists of a nucleic acid molecule which anneals to a complementary strand to the polynucleotide described in [63] under stringent conditions.

[68] A primer set for detecting a fusion gene of an FGFR3 gene and a TACC3 gene, comprising an antisense primer consisting of a nucleic acid molecule which anneals to a polynucleotide consisting of the nucleotide sequence of SEQ ID NO: 1, SEQ ID NO: 3, or SEQ ID NO: 5 under stringent conditions, and a sense primer consisting of a nucleic acid molecule which anneals to a complementary strand to the polynucleotide under stringent conditions.

[69] A primer set comprising a sense primer and an antisense primer selected from the group consisting of the following (a) to (c):
(a) a sense primer, which is an oligonucleotide consisting of at least 16 consecutive nucleotides in the region of nucleotides 1-2628 of SEQ ID NO: 1, and an antisense primer, which is an oligonucleotide complementary to an oligonucleotide consisting of at least 16 consecutive nucleotides in the region of nucleotides 2635-5004 of SEQ ID NO: 1,
(b) a sense primer, which is an oligonucleotide consisting of at least 16 consecutive nucleotides in the region of nucleotides 1-2628 of SEQ ID NO: 3, and an antisense primer, which is an oligonucleotide complementary to an oligonucleotide consisting of at least 16 consecutive nucleotides in the region of nucleotides 2635-3561 of SEQ ID NO: 3, and
(c) a sense primer, which is an oligonucleotide consisting of at least 16 consecutive nucleotides in the region of nucleotides 1-2536 of SEQ ID NO: 5, and an antisense primer, which is an oligonucleotide complementary to an oligonucleotide consisting of at least 16 consecutive nucleotides in the region of nucleotides 2537-3270 of SEQ ID NO: 5.

[70] A method for screening a substance which inhibits the activity and/or the expression of the polypeptide described in [44], the method comprising:
(1) bringing a test substance into contact with the polypeptide, or a cell expressing the polypeptide,
(2) analyzing whether or not the activity and/or the expression of the polypeptide is inhibited, and
(3) selecting a substance which inhibits the activity and/or the expression of the polypeptide.

[71] The method of [70], wherein the substance which inhibits the activity and/or the expression of the polypeptide is a therapeutic agent for a TACC3 fusion-positive cancer.

[72] The method of [70] or [71], wherein the cancer is a female genital cancer.

[73] The method of [70] or [71], wherein the cancer is a uterine cancer, a vaginal cancer, or a vulvar cancer.

[74] The method of [70] or [71], wherein the cancer is a cervical cancer, a vaginal cancer, or a vulvar cancer.

[75] The method of [70] or [71], wherein the cancer is a cervical cancer.

[76] A pharmaceutical composition for treating a TACC3 fusion-positive cancer, comprising a substance which inhibits the activity and/or the expression of a TACC3 fusion protein.

[77] The pharmaceutical composition of [76], wherein the substance which inhibits the activity and/or the expression of a TACC3 fusion protein is a kinase inhibitor.

[78] The pharmaceutical composition of [76] or [77], wherein the TACC3 fusion protein is the polypeptide described in [44].

[79] The pharmaceutical composition of any one of [76] to [78], wherein the cancer is a female genital cancer.

[80] The pharmaceutical composition of any one of [76] to [78], wherein the cancer is a uterine cancer, a vaginal cancer, or a vulvar cancer.

[81] The pharmaceutical composition of any one of [76] to [78], wherein the cancer is a cervical cancer, a vaginal cancer, or a vulvar cancer.

[82] The pharmaceutical composition of any one of [76] to [78], wherein the cancer is a cervical cancer.

[83] A method for treating an FGFR3 fusion-positive cancer, wherein a substance which inhibits the activity and/or the expression of an FGFR3 fusion protein is a kinase inhibitor.

[84] Use of a substance which inhibits the activity and/or the expression of an FGFR3 fusion protein in the manufacture of a pharmaceutical composition for treating an FGFR3 fusion-positive cancer.

[85] The method of any one of [29] to [34], wherein the cell expressing the polypeptide is the transformed cell of [6].

[86] A method for treating a TACC3 fusion-positive cancer, wherein a substance which inhibits the activity and/or the expression of a TACC3 fusion protein is a kinase inhibitor.

[87] Use of a substance which inhibits the activity and/or the expression of a TACC3 fusion protein in the manufacture of a pharmaceutical composition for treating a TACC3 fusion-positive cancer.

[88] The method of any one of [70] to [75], wherein the cell expressing the polypeptide is the transformed cell of [47].

Advantageous Effects of Invention

The detection method of the present invention can be used as a method for detecting an FGFR3 fusion-positive cancer (in particular, a female genital cancer). Further, according to the detection method of the present invention, the FGFR3 fusion-positive cancer can be diagnosed in a subject, and it can be determined whether or not a patient is an application target for an FGFR3 inhibitor. The detection kit and the primer set of the present invention can be used in the detection method of the present invention. Further, drugs effective in the treatment of patients with the FGFR3 fusion-positive cancer can be screened by the inhibitor screening method of the present invention. The drugs obtained by the screening can be used as active ingredients of a pharmaceutical composition for treating the FGFR3 fusion-positive cancer, and can be used in treating the FGFR3 fusion-positive cancer.

The detection method of the present invention can be used as a method for detecting a TACC3 fusion-positive cancer (in particular, a female genital cancer). Further, according to the detection method of the present invention, the TACC3 fusion-positive cancer can be diagnosed in a subject, and it can be determined whether or not a patient is an application target for a TACC3 inhibitor. The detection kit and the primer set of the present invention can be used in the detection method of the present invention. Further, drugs effective in the treatment of patients with the TACC3 fusion-positive cancer can be screened by the inhibitor screening method of the present invention. The drugs obtained by the screening can be used as active ingredients of a pharmaceutical composition for treating the TACC3 fusion-positive cancer, and can be used in treating the TACC3 fusion-positive cancer.

DESCRIPTION OF EMBODIMENTS

<<Definitions and the Like>>
<Fusion Point>

The term "fusion point in an FGFR3 fusion gene" as used herein means a point or a region in which a polynucleotide derived from the FGFR3 gene, in the FGFR3 fusion gene, is fused to a polynucleotide derived from a gene that constitutes the fusion gene together with the FGFR3 gene.

The term "fusion point in a TACC3 fusion gene" as used herein means a point or a region in which a polynucleotide derived from the TACC3 gene, in the TACC3 fusion gene, is fused to a polynucleotide derived from a gene that constitutes the fusion gene together with the TACC3 gene.

For example, in the case where the FGFR3 fusion gene or the TACC3 fusion gene is FGFR3-TACC3 fusion gene variant 1 (FGFR3ex18-TACC3ex4) of SEQ ID NO: 1, the fusion point is a region containing a point (2628th/2629th) in which the 3' terminal nucleotide (2628th) of a polynucleotide derived from the FGFR3 gene is fused to an insert sequence (AAACAG; 2629th-2634th), the insert sequence (AAACAG), and a point (2634th/2635th) in which the insert sequence (AAACAG) is fused to the 5' terminal nucleotide (2635th) of a polynucleotide derived from the TACC3 gene.

In the case where the FGFR3 fusion gene or the TACC3 fusion gene is FGFR3-TACC3 fusion gene variant 2 (FGFR3ex18-TACC3ex9) of SEQ ID NO: 3, the fusion point is a region containing a point in which the 3' terminal nucleotide (2628th) of a polynucleotide derived from the FGFR3 gene is fused to an insert sequence (AAACAG; 2629th-2634th), the insert sequence (AAACAG), and a point (2634th/2635th) in which the insert sequence (AAACAG) is fused to the 5' terminal nucleotide (2635th) of a polynucleotide derived from the TACC3 gene.

In the case where the FGFR3 fusion gene or the TACC3 fusion gene is FGFR3-TACC3 fusion gene variant 3 (FGFR3ex17-TACC3ex11) of SEQ ID NO: 5, the fusion point is a point (2536th/2537th) in which the 3' terminal nucleotide (2536th) of a polynucleotide derived from the FGFR3 gene is fused to the 5' terminal nucleotide (2537th) of a polynucleotide derived from the TACC3 gene.

The term "fusion point in an FGFR3 fusion protein" as used herein means a point or a region in which a polypeptide encoded by a polynucleotide derived from the FGFR3 gene, in the FGFR3 fusion protein, is fused to a polypeptide encoded by a polynucleotide derived from a gene that constitutes the fusion gene together with the FGFR3 gene.

The term "fusion point in a TACC3 fusion protein" as used herein means a point or a region in which a polypeptide encoded by a polynucleotide derived from the TACC3 gene, in the TACC3 fusion protein, is fused to a polypeptide encoded by a polynucleotide derived from a gene that constitutes the fusion gene together with the TACC3 gene.

For example, in the case where the FGFR3 fusion protein or the TACC3 fusion protein is FGFR3-TACC3 fusion gene variant 1 of SEQ ID NO: 2, the fusion point is a region containing a point (791st/792nd) in which the C-terminal amino acid (791st) of a polypeptide derived from the FGFR3 protein is fused to an insert sequence (Asn-Ser; 792nd-793rd), the insert sequence (Asn-Ser), and a point (793rd/794th) in which the insert sequence (Asn-Ser) is fused to the N-terminal amino acid (794th) of a polypeptide derived from the TACC3 protein.

In the case where the FGFR3 fusion protein or the TACC3 fusion protein is FGFR3-TACC3 fusion gene variant 2 of SEQ ID NO: 4, the fusion point is a region containing a point in which the C-terminal amino acid (791st) of a polypeptide derived from the FGFR3 protein is fused to an insert sequence (Asn-Ser; 792nd-793rd), the insert sequence (Asn-Ser), and a point (793rd/794th) in which the insert sequence (Asn-Ser) is fused to the N-terminal amino acid (794th) of a polypeptide derived from the TACC3 protein.

In the case where the FGFR3 fusion protein or the TACC3 fusion protein is FGFR3-TACC3 fusion gene variant 3 of SEQ ID NO: 6, the fusion point is a point (760th/761st) in which the C-terminal amino acid (760th) of a polypeptide derived from the FGFR3 protein is fused to the N-terminal amino acid (761st) of a polypeptide derived from the TACC3 protein.

<Cleavage of FGFR3 Gene or FGFR3 Protein>

The term "cleavage of an FGFR3 gene" or "an FGFR3 gene is cleaved" as used herein means a state in which the continuity of the FGFR3 gene is lost due to translocation, inversion, or the like of the gene, namely, a state in which the FGFR3 gene is separated into at least two polynucleotides, including a polynucleotide containing an FGFR3 kinase region and a polynucleotide containing other regions. The break point of the FGFR3 gene is not particularly limited, so long as a protein encoded by at least one polynucleotide generated by the cleavage of the FGFR3 gene maintains the FGFR3 kinase activity.

The term "cleavage of a gene other than FGFR3" or "a gene other than FGFR3 is cleaved" as used herein means a state in which the continuity of the gene other than FGFR3 (also called the other gene) is lost due to translocation, inversion, or the like of the gene, namely, a state in which the other gene is separated into at least two polynucleotides.

The term "cleavage of an FGFR3 protein" or "an FGFR3 protein is cleaved" as used herein means, based on the fact that the FGFR3 gene is cleaved as previously described, a state in which the continuity of the FGFR3 protein is lost, namely, a state in which the FGFR3 protein is separated into at least two polypeptides, including a polypeptide containing an FGFR3 kinase region and a polypeptide containing other regions. The break point of the FGFR3 protein is not particularly limited, so long as at least one protein generated by the cleavage of the FGFR3 protein maintains the FGFR3 kinase activity.

The term "cleavage of a protein other than FGFR3" or "a protein other than FGFR3 is cleaved" as used herein means, based on the fact that the other gene is cleaved as previously described, a state in which the continuity of the protein other than FGFR3 (also called the other protein) is lost, namely, a state in which the other protein is separated into at least two polypeptides.

<Cleavage of TACC3 Gene or TACC3 Protein>

The term "cleavage of a TACC3 gene" or "a TACC3 gene is cleaved" as used herein means a state in which the continuity of the TACC3 gene is lost due to translocation, inversion, or the like, of the gene. The break point of the TACC3 gene is not particularly limited, so long as a protein encoded by the other gene that constitutes the TACC3 fusion gene together with the TACC3 gene maintains its function (for example, when the protein has a kinase domain, the function is a kinase activity).

The term "cleavage of a gene other than a TACC3 gene" or "a gene other than a TACC3 gene is cleaved" as used herein means a state in which the continuity of the gene other than TACC3 (also called the other gene) is lost due to translocation, inversion, or the like of the gene, namely, a state in which the other gene is separated into at least two polynucleotides.

The term "cleavage of a TACC3 protein" or "a TACC3 protein is cleaved" as used herein means, based on the fact that the TACC3 gene is cleaved as previously described, a state in which the continuity of the TACC3 protein is lost, namely, a state in which the TACC3 protein is separated into at least two polypeptides. The break point of the TACC3 protein is not particularly limited, so long as the other protein that constitutes the TACC3 fusion protein together with the TACC3 protein maintains its function (for example, when the other protein has a kinase domain, the function is a kinase activity).

The term "cleavage of a protein other than a TACC3 protein" or "a protein other than a TACC3 protein is cleaved" as used herein means, based on the fact that the other gene is cleaved as previously described, a state in which the continuity of the protein other than TACC3 (also called the other protein) is lost, namely, a state in which the other protein is separated into at least two polypeptides.

<5' Terminal Region/3' Terminal Region, and N-Terminal Region/C-Terminal Region>

The term "5' terminal region" means, in the case of a fusion gene, a polynucleotide at the 5' terminal side from the fusion point, and in the case of a wild-type gene (a gene that is not a fusion gene), a polynucleotide at the 5' terminal side from the break point when the wild-type gene constitutes a fusion gene. The 5' terminal region may be genomic DNA, an mRNA, or a cDNA. For example, in the case of genomic DNA, the region is also called a 5' terminal genomic region.

The term "3' terminal region" means, in the case of a fusion gene, a polynucleotide at the 3' terminal side from the fusion point, and in the case of a wild-type gene (a gene that is not a fusion gene), a polynucleotide at the 3' terminal side from the break point when the wild-type gene constitutes a fusion gene. The 3' terminal region may be genomic DNA, an mRNA, or a cDNA. For example, in the case of genomic DNA, the region is also called a 3' terminal genomic region.

The term "N-terminal region" means, in the case of a fusion protein, a polypeptide at the N-terminal side from the fusion point, and in the case of a wild-type protein (a protein that is not a fusion protein), a polypeptide at the N-terminal side from the break point when the wild-type protein constitutes a fusion protein.

The term "C-terminal region" means, in the case of a fusion protein, a polypeptide at the C-terminal side from the fusion point, and in the case of a wild-type protein (a protein that is not a fusion protein), a polypeptide at the C-terminal side from the break point when the wild-type protein constitutes a fusion protein.

For example, in the case of FGFR3-TACC3 fusion gene variant 1 (FGFR3ex18-TACC3ex4) of SEQ ID NO: 1, the 5' terminal region is a polynucleotide consisting of nucleotides 1-2628, and the 3' terminal region is a polynucleotide consisting of nucleotides 2635-5004. In the case of FGFR3-TACC3 fusion protein variant 1 of SEQ ID NO: 2, the N-terminal region is a polypeptide (amino acids 1-791 of SEQ ID NO: 2) encoded by the CDS (nucleotides 257-2628 of SEQ ID NO: 1) at the 5' terminal region of FGFR3ex18-TACC3ex4, and the C-terminal region is a polypeptide (amino acids 794-1529 of SEQ ID NO: 2) encoded by the CDS (nucleotides 2635-4846 of SEQ ID NO: 1) at the 3' terminal region of FGFR3ex18-TACC3ex4.

In the case of FGFR3-TACC3 fusion gene variant 2 (FGFR3ex18-TACC3ex9) of SEQ ID NO: 3, the 5' terminal region is a polynucleotide consisting of nucleotides 1-2628, and the 3' terminal region is a polynucleotide consisting of nucleotides 2635-3561. In the case of FGFR3-TACC3 fusion protein variant 2 of SEQ ID NO: 4, the N-terminal region is a polypeptide (amino acids 1-791 of SEQ ID NO: 4) encoded by the CDS (nucleotides 257-2628 of SEQ ID NO: 3) at the 5' terminal region of FGFR3ex18-TACC3ex9, and the C-terminal region is a polypeptide (amino acids 794-1048 of SEQ ID NO: 4) encoded by the CDS (nucleotides 2635-3403 of SEQ ID NO: 3) at the 3' terminal region of FGFR3ex18-TACC3ex9.

In the case of FGFR3-TACC3 fusion gene variant 3 (FGFR3ex17-TACC3ex11) of SEQ ID NO: 5, the 5' terminal region is a polynucleotide consisting of nucleotides 1-2536, and the 3' terminal region is a polynucleotide consisting of nucleotides 2537-3270. In the case of FGFR3-TACC3 fusion protein variant 3 of SEQ ID NO: 6, the N-terminal region is a polypeptide (amino acids 1-760 of SEQ ID NO: 6) encoded by the CDS (nucleotides 257-2536 of SEQ ID NO: 5) at the 5' terminal region of GFR3ex17-TACC3ex11, and the C-terminal region is a polypeptide (amino acids 761-951 of SEQ ID NO: 6) encoded by the CDS (nucleotides 2537-3112 of SEQ ID NO: 5) at the 3' terminal region of GFR3ex17-TACC3ex11.

<cDNA Reference Sequences>

As cDNA reference sequences of each original gene, ENST00000340107 for FGFR3, and ENST00000313288 for TACC3 are used, respectively. As amino acid reference sequences of each protein, ENSP00000339824 for FGFR3, and ENSP00000326550 for TACC3 are used, respectively.

<Stringent Conditions>

The term "under stringent conditions" as used herein means that the hybridization is carried out in a solution containing 5×SSPE, 5×Denhardt's solution, 0.5% SDS, 50% formamide, and 200 μg/mL salmon sperm DNA at 42° C. overnight, and the washing is carried out in a solution containing 0.5×SSC and 0.1% SDS at 42° C. The term "under more stringent conditions" as used herein means that the hybridization is carried out in a solution containing 5×SSPE, 5×Denhardt's solution, 0.5% SDS, 50% formamide, and 200 μg/mL salmon sperm DNA at 42° C. overnight, and that the washing is carried out in a solution containing 0.2×SSC and 0.1% SDS at 65° C.

<Oncogenic Potential>

Whether or not a certain polypeptide has "oncogenic potential" can be confirmed by a known method, for example, a method described in Example 4 of WO 2011/162295. More particularly, a nude mouse is subcutaneously inoculated with a host (3T3 fibroblast) into which a plasmid capable of expressing the polypeptide is introduced, and the oncogenic potential is confirmed by judging the presence or absence of tumor formation. With respect to the FGFR3-TACC3 fusion gene, transformation in transduced cells, and oncogenic potential in transduced-cell-transplanted mice were shown, and it is suggested that the presence of the fusion gene or its transcriptional product is a cause of cancer in the expression site (See Non-patent literature 2).

<<Sample in the Detection Method of the Present Invention>>

<Target Organ>

The detection method of the present invention can be preferably used in the detection of cancer that occurs in the target organ. As a site to be analyzed (target organ) in the subject, female genitalia is preferable, the uterus, vagina, or vulva is more preferable, the cervix of the uterus, the vagina, or the vulva is still more preferable, and the cervix of the uterus is most preferable.

The histological type of the site to be analyzed is not limited, so long as the detection method of the present invention can be applied. Squamous epithelial tissues and glandular tissues may be exemplified, and squamous epithelial tissues are preferable.

<Specimen Collected from Subject>

As a sample obtained from a subject in the detection method of the present invention, specimens collected from a subject (i.e., samples isolated from a living body), more particularly, any body fluid collected (preferably blood), an excised specimen from the affected area of the subject, a biopsy sample or scraping specimen, menstrual blood, secretions from the uterus, a lavage fluid, or the like, can be used. In view of detection sensitivity, a sample containing cells from the site to be analyzed in the target organ is preferable, and an excised specimen or a biopsy sample from the site to be analyzed of the subject is more preferable.

<Treatment of Specimen>

The detection method of the FGFR3 fusion gene or the FGFR3 fusion protein of the present invention can be carried out by preparing a tissue section, a cell suspension, or the like of the sample obtained from the subject, and detecting the FGFR3 fusion gene or the FGFR3 fusion protein in the cells contained in the tissue section or the cell suspension by a technique well-known to those skilled in the art. Alternatively, a lysate is prepared from the sample obtained from the subject, and the genes or proteins contained in the lysate are extracted, and the FGFR3 fusion gene or the FGFR3 fusion protein can be detected in the obtained extract by a technique well-known to those skilled in the art. In connection with this, the detection of the FGFR3 fusion gene may be a detection of genomic DNA of the FGFR3 fusion gene; a detection of mRNA, which is a transcript of the genomic DNA; or a detection of cDNA obtained from the mRNA as a template.

The detection method of the TACC3 fusion gene or the TACC3 fusion protein of the present invention can be carried out by preparing a tissue section, a cell suspension, or the like of the sample obtained from the subject, and detecting the TACC3 fusion gene or the TACC3 fusion protein in the cells contained in the tissue section or the cell suspension by a technique well-known to those skilled in the art. Alternatively, a lysate is prepared from the sample obtained from the subject, and the genes or proteins contained in the lysate are extracted, and the TACC3 fusion gene or the TACC3 fusion protein can be detected in the obtained extract by a technique well-known to those skilled in the art. In connection with this, the detection of the TACC3 fusion gene may be a detection of genomic DNA of the TACC3 fusion gene; a detection of mRNA, which is a transcript of the genomic DNA; or a detection of cDNA obtained from the mRNA as a template.

<<Target to be Detected in the Detection Method of the Present Invention>>

The detection method of the present invention includes a method for detecting an FGFR3 fusion in a sample obtained from a subject, namely, a method for detecting a fusion protein containing the FGFR3 kinase region (also called "FGFR3 fusion protein"), and a method for detecting a fusion gene encoding the fusion protein (also called "FGFR3 fusion gene").

The detection method of the present invention includes a method for detecting a TACC3 fusion in a sample obtained from a subject, namely, a method for detecting a TACC3 fusion protein, and a method for detecting a fusion gene encoding the fusion protein (also called "TACC3 fusion gene").

<FGFR3 Fusion: FGFR3 Fusion Protein and FGFR3 Fusion Gene>

The term "FGFR3 fusion" as used herein includes the FGFR3 fusion protein and the FGFR3 fusion gene.

The FGFR3 fusion protein in the present invention is a fusion protein constructed from a polypeptide derived from the FGFR3 protein, and a polypeptide derived from a protein other than the FGFR3 protein. The polypeptide derived from the FGFR3 protein is not particularly limited, so long as it comprises at least a polypeptide of the FGFR3 kinase region in the FGFR3 protein. The polypeptide derived from the protein other than the FGFR3 protein is not particularly limited, so long as it comprises at least a portion of the other protein.

The other protein is not particularly limited, so long as the FGFR3 fusion protein, which is constructed by fusing the other protein to a portion of the FGFR3 protein containing the FGFR3 kinase domain, has oncogenic potential. It is preferable that the constructed FGFR3 fusion protein has oncogenic potential by constitutively maintaining the FGFR3 kinase activation in the FGFR3 fusion protein.

The FGFR3 fusion protein may comprise the third polypeptide, which is neither the polypeptide derived from the FGFR3 protein, nor the polypeptide derived from a protein other than the FGFR3 protein, so long as the FGFR3 kinase activation is constitutively maintained, and the constructed FGFR3 fusion protein has oncogenic potential. The third polypeptide may be located at the N-terminus of the FGFR3 fusion protein, at the C-terminus of the FGFR3 fusion protein, or between the polypeptide derived from the FGFR3 protein and the polypeptide derived from a protein other than the FGFR3 protein.

As the FGFR3 fusion protein, a fusion protein in which the other protein is the TACC3 protein is most preferable. More particularly, a fusion protein of the FGFR3 protein and the TACC3 protein (hereinafter also referred to as a FGFR3-TACC3 fusion protein), constructed from an FGFR3-derived polypeptide comprising at least a polypeptide of the FGFR3 kinase region, and a TACC3-derived polypeptide comprising a polypeptide of at least a portion of the TACC3 protein, is preferable.

<TACC3 Fusion: TACC3 Fusion Protein and TACC3 Fusion Gene>

The term "TACC3 fusion" as used herein includes the TACC3 fusion protein and the TACC3 fusion gene.

The TACC3 fusion protein in the present invention is a fusion protein constructed from a polypeptide derived from the TACC3 protein, and a polypeptide derived from a protein other than the TACC3 protein. The polypeptide derived from the TACC3 protein is not particularly limited, so long as it comprises at least a polypeptide of the TACC3 protein. The polypeptide derived from the protein other than the TACC3 protein is not particularly limited, so long as it comprises at least a portion of the other protein.

The other protein is not particularly limited, so long as the TACC3 fusion protein, which is constructed by fusing the other protein to a portion of the TACC3 protein, has oncogenic potential. It is preferable that the TACC3 fusion protein has oncogenic potential by constitutively maintaining the activation of a functional domain (preferably a kinase domain) of the other protein.

The TACC3 fusion protein may comprise the third polypeptide, which is neither the polypeptide derived from the TACC3 protein, nor the polypeptide derived from a protein other than the TACC3 protein, so long as the activation of the functional domain of the protein other than the TACC3 protein is constitutively maintained by fusing it to a portion of the TACC3 protein, and the constructed TACC3 fusion protein has oncogenic potential. The third polypeptide may be located at the N-terminus of the TACC3 fusion protein, at the C-terminus of the TACC3 fusion protein, or between the polypeptide derived from the TACC3 protein and the polypeptide derived from the protein other than the TACC3 protein.

As the TACC3 fusion protein, a fusion protein in which the other protein is the FGFR3 protein is most preferable. More particularly, a fusion protein of the TACC3 protein and the FGFR3 protein (hereinafter also referred to as a FGFR3-TACC3 fusion protein), constructed from a TACC3-derived polypeptide comprising a polypeptide of at least a portion of the TACC3 protein, and a polypeptide of at least a portion of the FGFR3 protein comprising a polypeptide of at least the FGFR3 kinase region, is preferable.

As the "FGFR3-TACC3 fusion protein", the following polypeptides (a) to (f) are most preferable:

(a) a polypeptide consisting of the amino acid sequence of SEQ ID NO: 2, (b) a polypeptide consisting of the amino acid sequence of SEQ ID NO: 4, (c) a polypeptide consisting of the amino acid sequence of SEQ ID NO: 6, (d) a polypeptide with oncogenic potential comprising the amino acid sequence of SEQ ID NO: 2, SEQ ID NO: 4, or SEQ ID NO: 6, (e) a polypeptide with oncogenic potential comprising an amino acid sequence that has at least 80% identity to the amino acid sequence of SEQ ID NO: 2, SEQ ID NO: 4, or SEQ ID NO: 6 (hereinafter referred to as a "homologous polypeptide"), and (f) a polypeptide with oncogenic potential comprising an amino acid sequence in which one or several amino acids are deleted, substituted, and/or inserted in the amino acid sequence of SEQ ID NO: 2, SEQ ID NO: 4, or SEQ ID NO: 6 (hereinafter referred to as a "variation functionally equivalent").

The amino acid sequence of SEQ ID NO: 2 is a sequence encoded by the nucleotide sequence of SEQ ID NO: 1, in particular, the nucleotide sequence (CDS) of nucleotides 257-4846 of SEQ ID NO: 1. The nucleotide sequence of SEQ ID NO: 1 consists of a 5'-UTR (5' untranslated region) sequence of the FGFR3 gene, a nucleotide sequence from the initiation codon ATG to the 92nd nucleotide of exon 18 of the FGFR3 gene, AAACAG as an insertion sequence, a nucleotide sequence from exon 4 to the stop codon in exon 16 of the TACC3 gene, and a 3'-UTR (3' untranslated region) sequence of the TACC3 gene. In the nucleotide sequence of SEQ ID NO: 1, the sequence of nucleotides 1-2628 is derived from the FGFR3 gene, and the sequence of nucleotides 2635-5004 is derived from the TACC3 gene. Hereinafter the polypeptide consisting of the amino acid sequence of SEQ ID NO: 2, and the polynucleotide consisting of the nucleotide sequence encoding the amino acid sequence (including the polynucleotide consisting of the nucleotide sequence of SEQ ID NO: 1) are referred to as FGFR3ex18-TACC3ex4 fusions (sometimes referred to as FGFR3ex18-TACC3ex4).

The amino acid sequence of SEQ ID NO: 4 is a sequence encoded by the nucleotide sequence of SEQ ID NO: 3, in particular, the nucleotide sequence (CDS) of nucleotides 257-3403 of SEQ ID NO: 3. The nucleotide sequence of SEQ ID NO: 3 consists of a 5'-UTR sequence of the FGFR3 gene, a nucleotide sequence from the initiation codon ATG to the 92nd nucleotide of exon 18 of the FGFR3 gene, AAACAG as an insertion sequence, a nucleotide sequence from exon 9 to the stop codon in exon 16 of the TACC3 gene, and a 3'-UTR sequence of the TACC3 gene. In the nucleotide sequence of SEQ ID NO: 3, the sequence of nucleotides 1-2628 is derived from the FGFR3 gene, and the sequence of nucleotides 2635-3561 is derived from the TACC3 gene. Hereinafter the polypeptide consisting of the amino acid sequence of SEQ ID NO: 4, and the polynucleotide consisting of the nucleotide sequence encoding the amino acid sequence (including the polynucleotide consisting of the nucleotide sequence of SEQ ID NO: 3) are referred to as FGFR3ex18-TACC3ex9 fusions (sometimes referred to as FGFR3ex18-TACC3ex9).

The amino acid sequence of SEQ ID NO: 6 is a sequence encoded by the nucleotide sequence of SEQ ID NO: 5, in particular, the nucleotide sequence (CDS) of nucleotides 257-3112 of SEQ ID NO: 5. The nucleotide sequence of SEQ ID NO: 5 consists of a 5'-UTR sequence of the FGFR3 gene, a nucleotide sequence from the initiation codon ATG to exon 17 of the FGFR3 gene, a nucleotide sequence from exon 11 to the stop codon in exon 16 of the TACC3 gene, and a 3'-UTR sequence of the TACC3 gene. In the nucleotide sequence of SEQ ID NO: 5, the sequence of nucleotides 1-2536 is derived from the FGFR3 gene, and the sequence of nucleotides 2537-3270 is derived from the TACC3 gene. Hereinafter the polypeptide consisting of the amino acid sequence of SEQ ID NO: 6, and the polynucleotide consisting of the nucleotide sequence encoding the amino acid sequence (including the polynucleotide consisting of the nucleotide sequence of SEQ ID NO: 5) are referred to as FGFR3ex17-TACC3ex11 fusions (sometimes referred to as FGFR3ex17-TACC3ex11).

The number of amino acids capable of being deleted, substituted, and/or inserted in the "variation functionally equivalent" is 1 to several amino acids, preferably 1 to 10, more preferably 1 to 7, and most preferably 1 to 5.

The "homologous polypeptide" is a "polypeptide with oncogenic potential comprising an amino acid sequence that has at least 80% identity to the amino acid sequence of SEQ ID NO: 2, SEQ ID NO: 4, or SEQ ID NO: 6". With respect to the identity, a polypeptide comprising an amino acid sequence that has, preferably at least 90% identity, more preferably at least 95% identity, and still more preferably at least 98% identity, is preferable. In connection with this, the "polypeptide with oncogenic potential comprising an amino acid sequence that has at least 80% identity to the amino acid sequence of SEQ ID NO: 2, SEQ ID NO: 4, or SEQ ID NO: 6" includes a "polypeptide that has at least 80% identity and at least one substitution, deletion and/or insertion (preferably substitution)" (a homologous polypeptide in a narrow sense) as well as a "polypeptide that has 100% identity".

The term "identity" as used herein means the value "Identity" obtained by a NEEDLE program (J Mol Biol 1970; 48: 443-453) search, using the following default parameters:
Gap penalty=10
Extend penalty=0.5
Matrix=EBLOSUM62

The FGFR3 fusion gene of the present invention is a polynucleotide encoding the FGFR3 fusion protein. The FGFR3 fusion protein and the FGFR3 fusion gene are sometimes and collectively referred to as the "FGFR3 fusion".

As the FGFR3 fusion of the present invention, FGFR3-TACC3 fusion variant 1 (FGFR3ex18-TACC3ex4), FGFR3-TACC3 fusion variant 2 (FGFR3ex18-TACC3ex9), and FGFR3-TACC3 fusion variant 3 (FGFR3ex17-TACC3ex11) are preferable. In particular, as the FGFR3 fusion protein of the present invention, FGFR3-TACC3 fusion protein variant 1 (FGFR3ex18-TACC3ex4), FGFR3-TACC3 fusion protein variant 2 (FGFR3ex18-TACC3ex9), and FGFR3-TACC3 fusion protein variant 3 (FGFR3ex17-TACC3ex11) are preferable. Further, as the FGFR3 fusion gene of the present invention, FGFR3-TACC3 fusion gene variant 1 (FGFR3ex18-TACC3ex4), FGFR3-TACC3 fusion gene variant 2 (FGFR3ex18-TACC3ex9), and FGFR3-TACC3 fusion gene variant 3 (FGFR3ex17-TACC3ex11) are preferable.

The TACC3 fusion gene of the present invention is a polynucleotide encoding the TACC3 fusion protein. The TACC3 fusion protein and the TACC3 fusion gene are sometimes and collectively referred to as the "TACC3 fusion".

As the TACC3 fusion of the present invention, FGFR3-TACC3 fusion variant 1 (FGFR3ex18-TACC3ex4), FGFR3-TACC3 fusion variant 2 (FGFR3ex18-TACC3ex9), and FGFR3-TACC3 fusion variant 3 (FGFR3ex17-TACC3ex11) are preferable. In particular, as the TACC3 fusion protein of the present invention, FGFR3-TACC3 fusion protein variant 1 (FGFR3ex18-TACC3ex4), FGFR3-TACC3 fusion protein variant 2 (FGFR3ex18-TACC3ex9), and FGFR3-TACC3 fusion protein variant 3 (FGFR3ex17-TACC3ex11) are preferable. Further, as the TACC3 fusion gene of the present invention, FGFR3-TACC3 fusion gene variant 1 (FGFR3ex18-TACC3ex4), FGFR3-TACC3 fusion gene variant 2 (FGFR3ex18-TACC3ex9), and FGFR3-TACC3 fusion gene variant 3 (FGFR3ex17-TACC3ex11) are preferable.

<<Embodiments of Detection Method of the Present Invention (Method for Detecting Fusion Protein and Fusion Gene)>>

The detection method of the present invention includes: a detection method comprising a step of detecting the cleavage of the FGFR3 protein, or the cleavage of a gene encoding the FGFR3 protein, in a sample derived from female genitalia obtained from a subject; and a detection method comprising a step of detecting the presence of a fusion protein constructed from the FGFR3 protein and a protein other than the FGFR3 protein, or the presence of a fusion gene encoding the fusion protein, in a sample derived from female genitalia obtained from a subject.

The detection method of the present invention includes: a detection method comprising a step of detecting the cleavage of the TACC3 protein, or the cleavage of a gene encoding the FGFR3 TACC3, in a sample derived from female genitalia obtained from a subject; and a detection method comprising a step of detecting the presence of a fusion protein constructed from the TACC3 protein and a protein other than the TACC3 protein, or the presence of a fusion gene encoding the fusion protein, in a sample derived from female genitalia obtained from a subject.

<Embodiments of Detecting FGFR3 Fusion Gene>

Hereinafter, embodiments of detecting the FGFR3 fusion gene will be explained, but the present invention is not limited to these embodiments.

In connection with this, the detection of the specific region of the gene in each of the following embodiments may be carried out, regardless of the examples, using a probe or primers designed based on the pre-analyzed nucleotide sequence, or by sequencing.

[Embodiments of Detecting FGFR3 Fusion Gene (1)]
<Embodiment of Detecting FGFR3 Fusion Gene (1-a)>

As an embodiment of detecting the FGFR3 fusion gene, on the basis of the fact that, when the FGFR3 fusion gene is constructed, the FGFR3 gene is cleaved into two or more polynucleotides, the FGFR3 fusion gene can be detected by detecting a state in which the FGFR3 gene is cleaved, namely, a state in which the continuity of the 5' terminal region of the FGFR3 gene and the 3' terminal region of the FGFR3 gene is lost.

More particularly, the FGFR3 fusion gene can be detected, for example, using the first probe that specifically hybridizes to the 5' terminal region of the FGFR3 gene, and the second probe that specifically hybridizes to the 3' terminal region of the FGFR3 gene, by detecting the fact that the two gene regions are apart from each other on a chromosome.

In connection with this, the FGFR3 fusion gene may be detected by confirming a state in which the other gene, which constitutes the fusion gene by fusing it to a polynucleotide derived from the FGFR3 gene, is cleaved, using the above-mentioned method.

<Embodiment of Detecting FGFR3 Fusion Gene (1-b)>

As another embodiment, the FGFR3 fusion gene can be detected by separately and specifically detecting the expression levels of the 5' terminal region and the 3' terminal region of the FGFR3 gene, and calculating the ratio of the expression levels. More particularly, for example, when the expression level of the 5' terminal region of the FGFR3 gene is different from the expression level of the 3' terminal region of the FGFR3 gene, the FGFR3 fusion gene can be detected.

Alternatively, the FGFR3 fusion gene may be detected by confirming the other gene (i.e., the gene other than the FGFR3 gene), which constitutes the FGFR3 fusion gene together with the FGFR3 gene, using the above-mentioned method.

<Embodiment of Detecting FGFR3 Fusion Gene (1-c)>

As still another embodiment, in the case where the forming process of the FGFR3 fusion gene is accompanied by a duplication of at least a portion of the FGFR3 or the other gene, namely, in the case where the FGFR3 fusion gene is constructed from a duplicated polynucleotide derived from the FGFR3 gene, and a duplicated polynucleotide derived from the other gene (i.e., the gene other than the FGFR3 gene), which constitutes the FGFR3 fusion gene together with the FGFR3, the FGFR3 fusion gene can be detected by detecting the duplication of the polynucleotide derived from the FGFR3 gene, or the polynucleotide derived from the other gene.

[Embodiment of Detecting FGFR3 Fusion Gene (2)]

As an embodiment of detecting the FGFR3 fusion gene, on the basis of the fact that the FGFR3 fusion gene is constructed by fusing a polynucleotide derived from the FGFR3 gene to a polynucleotide derived from the gene other than the FGFR3, the FGFR3 fusion gene can be detected by detecting a fusion polynucleotide sequentially containing at least a portion of the polynucleotide derived from the FGFR3 gene, and at least a portion of the polynucleotide derived from the gene other than the FGFR3, in the FGFR3 fusion gene.

More particularly, the FGFR3 fusion gene can be detected, for example, using the first probe that specifically hybridizes to the 5' terminal region of a polynucleotide derived from the FGFR3 gene, and the second probe that specifically hybridizes to the 3' terminal region of the gene other than the FGFR3, by detecting the fact that the two gene regions are adjacent to each other on a chromosome. When the gene other than the FGFR3 is TACC3, namely, when the FGFR3 fusion gene is the FGFR3-TACC3 fusion gene, a probe specifically hybridizing to the 3' terminal region of a polynucleotide derived from the TACC3 gene may be used, as the second probe.

[Embodiment of Detecting FGFR3 Fusion Gene (3)]

As an embodiment of detecting the FGFR3 fusion gene, on the basis of the fact that the FGFR3 fusion gene is constructed by fusing a polynucleotide derived from the FGFR3 gene to a polynucleotide derived from the gene other than the FGFR3 at the fusion point, the FGFR3 fusion gene can be detected by detecting a fusion polynucleotide containing the fusion point and sequentially containing at least a portion of the polynucleotide derived from the FGFR3 gene, and at least a portion of the polynucleotide derived from the gene other than the FGFR3, in the FGFR3 fusion gene.

More particularly, the FGFR3 fusion gene can be detected by carrying out a PCR reaction, for example, using the first primer that specifically anneals to the 5' terminal region of a polynucleotide derived from the FGFR3 gene, and the second primer that specifically anneals to the 3' terminal region of a polynucleotide derived from the gene other than the FGFR3 gene, and confirming the fact that a desired PCR product showing the presence of the fusion point can be obtained.

<Embodiments of Detecting FGFR3 Fusion Protein>

Hereinafter, embodiments of detecting the FGFR3 fusion protein will be explained, but the present invention is not limited to these embodiments.

[Embodiments of Detecting FGFR3 Fusion Protein (1)]
<Embodiment of Detecting FGFR3 Fusion Protein (1-a)>

As an embodiment of detecting the FGFR3 fusion protein, on the basis of the fact that, when the FGFR3 fusion gene is constructed, the FGFR3 protein encoded by the FGFR3 gene is also cleaved, the FGFR3 fusion protein can be detected by detecting a state in which the FGFR3 protein is cleaved, namely, a state in which the N-terminal region and the C-terminal region of the FGFR3 protein are not continuous.

More particularly, the FGFR3 fusion protein can be detected, for example, using the first antibody that specifically binds to the N-terminal region of the FGFR3 protein, and the second antibody that specifically binds to the C-terminal region of the FGFR3 protein, by confirming the fact that the two regions are not present in the same protein.

Alternatively, the FGFR3 fusion protein may be detected by confirming the cleaved state of the other protein, which constitutes the FGFR3 fusion protein together with the FGFR3 protein, using the above-mentioned method.

<Embodiment of Detecting FGFR3 Fusion Protein (1-b)>

As another embodiment, the FGFR3 fusion protein can be detected by separately and specifically detecting the expression levels of the N-terminal region and the C-terminal region of the FGFR3 protein, and calculating the ratio of the expression levels. More particularly, the FGFR3 fusion protein can be detected, for example, using the fact that the expression level of the N-terminal region of the FGFR3 protein is different from the expression level of the C-terminal region of the FGFR3 protein, as an index.

Alternatively, the FGFR3 fusion protein may be detected by confirming the other protein, which constitutes the FGFR3 fusion protein together with the FGFR3 protein, using the above-mentioned method.

[Embodiment of Detecting FGFR3 Fusion Protein (2)]

As an embodiment of detecting the FGFR3 fusion protein, on the basis of the fact that the FGFR3 fusion protein is constructed by fusing a polypeptide derived from the FGFR3 protein to a polypeptide derived from the protein other than the FGFR3 protein, the FGFR3 fusion protein can be detected by detecting a fusion polypeptide sequentially containing at least a portion of the polypeptide derived from the FGFR3 protein, and at least a portion of the polypeptide derived from the protein other than the FGFR3 protein, in the FGFR3 fusion protein.

More particularly, the FGFR3 fusion protein can be detected, for example, using the first antibody that specifically binds to the N-terminal region of the FGFR3 protein, and the second antibody that specifically binds to the C-terminal region of the protein other than the FGFR3 protein, by confirming the fact that the two regions are present in the same protein.

[Embodiment of Detecting FGFR3 Fusion Protein (3)]

As an embodiment of detecting the FGFR3 fusion protein, on the basis of the fact that the FGFR3 fusion protein is constructed by fusing a polypeptide derived from the FGFR3 protein to a polypeptide derived from the protein other than the FGFR3 at the fusion point, the FGFR3 fusion protein can be detected by detecting a fusion polypeptide containing the fusion point and sequentially containing at least a portion of the polypeptide derived from the FGFR3 protein, and at least a portion of the polypeptide derived from the protein other than the FGFR3, in the FGFR3 fusion protein.

More particularly, the FGFR3 fusion protein can be detected, for example, by an immunoassay using an antibody that specifically recognizes a polypeptide containing the fusion point of the FGFR3 fusion protein.

[Embodiment of Detecting FGFR3 Fusion Protein (4)]

As an embodiment of detecting the FGFR3 fusion protein, the FGFR3 fusion protein can be detected using the activity of the FGFR3 fusion protein, as an index.

More particularly, the FGFR3 fusion protein can be detected, for example, by measuring a kinase activity of the FGFR3 protein, under the conditions that the activity of the wild-type FGFR3 protein is inhibited using an inhibitor for the wild-type FGFR3 protein, and using, as an index, the fact that the activity is higher, in comparison with the case where the FGFR3 fusion protein is not contained (namely, the wild-type FGFR3 protein is contained alone). In connection with this, the measurement method for the kinase activity of the FGFR3 protein may be appropriately selected from well-known methods for those skilled in the art. For example, the phosphorylation state of a molecule to be phosphorylated by the FGFR3 may be detected.

The detection of the FGFR3 fusion protein may be carried out using, as an index, the presence of the full-length polypeptide that constitutes the FGFR3 fusion protein, or the presence of a polypeptide that constitutes part of the FGFR3 fusion protein, and it is not particularly limited, so long as the presence of the FGFR3 fusion protein can be confirmed.

<Embodiments of Detecting TACC3 Fusion Gene>

Hereinafter, embodiments of detection of the TACC3 fusion gene will be explained, but the present invention is not limited to these embodiments.

In connection with this, the detection of the specific region of the gene in each of the following embodiments may be carried out, regardless of the examples, using a probe or primers designed based on the pre-analyzed nucleotide sequence, or by sequencing.

[Embodiments of Detecting TACC3 Fusion Gene (1)]

<Embodiment of Detecting TACC3 Fusion Gene (1-a)>

As an embodiment of detecting the TACC3 fusion gene, on the basis of the fact that, when the TACC3 fusion gene is constructed, the TACC3 gene is cleaved into two or more polynucleotides, the TACC3 fusion gene can be detected by detecting a state in which the TACC3 gene is cleaved, namely, a state in which the continuity of the 5' terminal region of the TACC3 gene and the 3' terminal region of the TACC3 gene is lost.

More particularly, the TACC3 fusion gene can be detected, for example, using the first probe that specifically hybridizes to the 5' terminal region of the TACC3 gene, and the second probe that specifically hybridizes to the 3' terminal region of the TACC3 gene, by detecting the fact that the two gene regions are apart from each other on a chromosome.

In connection with this, the TACC3 fusion gene may be detected by confirming a state in which the other gene, which constitutes the fusion gene by fusing it to a polynucleotide derived from the TACC3 gene, is cleaved, using the above-mentioned method.

<Embodiment of Detecting TACC3 Fusion Gene (1-b)>

As another embodiment, the TACC3 fusion gene can be detected by separately and specifically detecting the expression levels of the 5' terminal region and the 3' terminal region of the TACC3 gene, and calculating the ratio of the expression levels. More particularly, for example, when the expression level of the 5' terminal region of the TACC3 gene is different from the expression level of the 3' terminal region of the TACC3 gene, the TACC3 fusion gene can be detected.

Alternatively, the TACC3 fusion gene may be detected by confirming the other gene, which constitutes the TACC3 fusion gene together with the TACC3 gene, using the above-mentioned method.

<Embodiment of Detecting TACC3 Fusion Gene (1-c)>

As still another embodiment, in the case where the forming process of the TACC3 fusion gene is accompanied by a duplication of at least a portion of the TACC3 gene or the other gene, namely, in the case where the TACC3 fusion gene is constructed from a duplicated polynucleotide derived from the TACC3 gene, and a duplicated polynucleotide derived from the other gene, which constitutes the TACC3 fusion gene together with the TACC3, the TACC3 fusion gene can be detected by detecting the duplication of the polynucleotide derived from the TACC3 gene, or the polynucleotide derived from the other gene.

[Embodiment of Detecting TACC3 Fusion Gene (2)]

As an embodiment of detecting the TACC3 fusion gene, on the basis of the fact that the TACC3 fusion gene is constructed by fusing a polynucleotide derived from the TACC3 gene to a polynucleotide derived from the gene other than the TACC3, the TACC3 fusion gene can be detected by detecting a fusion polynucleotide sequentially containing at least a portion of the polynucleotide derived from the TACC3 gene, and at least a portion of the polynucleotide derived from the gene other than the TACC3, in the TACC3 fusion gene.

More particularly, the TACC3 fusion gene can be detected, for example, using the first probe that specifically hybridizes to the 3' terminal region of a polynucleotide derived from the TACC3 gene, and the second probe that specifically hybridizes to the 5' terminal region of a polynucleotide derived from the gene other than the TACC3 gene, by detecting the fact that the two gene regions are adjacent to each other on a chromosome. When the gene other than the TACC3 is FGFR3, namely, when the TACC3 fusion gene is the FGFR3-TACC3 fusion gene, a probe specifically hybridizes to the 5' terminal region of a polynucleotide derived from the FGFR3 gene may be used, as the second probe.

[Embodiment of Detecting TACC3 Fusion Gene (3)]

As an embodiment of detecting the TACC3 fusion gene, on the basis of the fact that the TACC3 fusion gene is constructed by fusing a polynucleotide derived from the TACC3 gene to a polynucleotide derived from the gene other than the TACC3 at the fusion point, the TACC3 fusion gene can be detected by detecting a fusion polynucleotide containing the fusion point and sequentially containing at least a portion of the polynucleotide derived from the TACC3 gene, and at least a portion of the polynucleotide derived from the gene other than the TACC3, in the TACC3 fusion gene.

More particularly, the TACC3 fusion gene can be detected by carrying out a PCR reaction, for example, using the first primer that specifically anneals to the 3' terminal region of a polynucleotide derived from the TACC3 gene, and the second primer that specifically anneals to the 5' terminal region of a polynucleotide derived from the gene other than the TACC3 gene, and confirming the fact that a desired PCR product showing the presence of the fusion point can be obtained.

<Embodiments of Detecting TACC3 Fusion Protein>

Hereinafter, embodiments of detection of the TACC3 fusion protein will be explained, but the present invention is not limited to these embodiments.

[Embodiments of Detecting TACC3 Fusion Protein (1)]
<Embodiment of Detecting TACC3 Fusion Protein (1-a)>

As an embodiment of detecting the TACC3 fusion protein, on the basis of the fact that, when the TACC3 fusion gene is constructed, the TACC3 protein encoded by the TACC3 gene is also cleaved, the TACC3 fusion protein can be detected by detecting a state in which the TACC3 protein is cleaved, namely, a state in which the continuity between the N-terminal region and the C-terminal region of the TACC3 protein is lost.

More particularly, the TACC3 fusion protein can be detected, for example, using the first antibody that specifically binds to the N-terminal region of the TACC3 protein, and the second antibody that specifically binds to the C-terminal region of the TACC3 protein, by confirming the fact that the two regions are not present in the same protein.

Alternatively, the TACC3 fusion protein may be detected by confirming the cleaved state of the other protein, which constitutes the TACC3 fusion protein together with the TACC3 protein, using the above-mentioned method.

<Embodiment of Detecting TACC3 Fusion Protein (1-b)>

As another embodiment, the TACC3 fusion protein can be detected by separately and specifically detecting the expression levels of the N-terminal region and the C-terminal region of the TACC3 protein, and calculating the ratio of the expression levels. More particularly, the TACC3 fusion protein can be detected, for example, using the fact that the expression level of the N-terminal region of the TACC3 protein is different from the expression level of the C-terminal region of the TACC3 protein, as an index.

Alternatively, the TACC3 fusion protein may be detected by confirming the other protein, which constitutes the TACC3 fusion protein together with the TACC3 protein, using the above-mentioned method.

[Embodiment of Detecting TACC3 Fusion Protein (2)]

As an embodiment of detecting the TACC3 fusion protein, on the basis of the fact that the TACC3 fusion protein is constructed by fusing a polypeptide derived from the TACC3 protein to a polypeptide derived from the protein other than the TACC3 protein, the TACC3 fusion protein can be detected by detecting a fusion polypeptide sequentially containing at least a portion of the polypeptide derived from the TACC3 protein, and at least a portion of the polypeptide derived from the protein other than the TACC3 protein, in the TACC3 fusion protein.

More particularly, the TACC3 fusion protein can be detected, for example, using the first antibody that specifically binds to the C-terminal region of the TACC3 protein, and the second antibody that specifically binds to the N-terminal region of the protein other than the TACC3 protein, by confirming the fact that the two regions are present in the same protein.

[Embodiment of Detecting TACC3 Fusion Protein (3)]

As an embodiment of detecting the TACC3 fusion protein, on the basis of the fact that the TACC3 fusion protein is constructed by fusing a polypeptide derived from the TACC3 protein to a polypeptide derived from the protein other than the TACC3 protein at the fusion point, the TACC3 fusion protein can be detected by detecting a fusion polypeptide containing the fusion point and sequentially containing at least a portion of the polypeptide derived from the TACC3 protein, and at least a portion of the polypeptide derived from the protein other than the TACC3, in the TACC3 fusion protein.

More particularly, the TACC3 fusion protein can be detected, for example, by an immunoassay using an antibody that specifically recognizes a polypeptide containing the fusion point of the TACC3 fusion protein.

[Embodiment of Detecting TACC3 Fusion Protein (4)]

As an embodiment of detecting the TACC3 fusion protein, the TACC3 fusion protein can be detected using the activity of the TACC3 fusion protein, as an index.

More particularly, for example, when the other protein, which constitutes the fusion protein together with the TACC3 protein, is a protein having an enzyme activity, the TACC3 fusion protein can be detected by using, as an index, the fact that the activity is higher, in comparison with the case where the TACC3 fusion protein is not contained (namely, the wild-type TACC3 protein is contained alone). In connection with this, the measurement method for the enzyme activity may be appropriately selected from well-known methods for those skilled in the art. For example, when the other protein is a protein having a kinase activity (preferably the FGFR3 protein), the phosphorylation state of a molecule to be phosphorylated by the TACC3 fusion protein may be detected.

The detection of the TACC3 fusion protein may be carried out using, as an index, the presence of the full-length polypeptide that constitutes the TACC3 fusion protein, or the presence of a polypeptide that constitutes part of the TACC3 fusion protein, and it is not particularly limited, so long as the presence of the TACC3 fusion protein can be confirmed.

<<Techniques Used in Detection Method>>

Hereinafter, the steps and detection techniques of the detection of the FGFR3 fusion gene (genomic DNA, mRNA, or cDNA), the detection of the TACC3 fusion gene (genomic DNA, mRNA, or cDNA), the detection of the FGFR3 fusion protein, and the detection of the TACC3 fusion protein will be further explained in detail, but the present invention is not limited thereto.

In the case where a gene (genomic DNA or mRNA) or a protein is extracted from the sample obtained from a subject, or in the case where tissue sections, a cell suspension, or the like is prepared, those skilled in the art can appropriately select preferred techniques for detecting the FGFR3 fusion gene or the TACC3 fusion gene, or the FGFR3 fusion protein or the TACC3 fusion protein in the prepared sample.

<Detection of Fusion Gene>

The detection of the FGFR3 fusion gene or the TACC3 fusion gene may be a detection of genomic DNA of the FGFR3 fusion gene or the TACC3 fusion gene, a detection of an mRNA that is a transcriptional product from the genomic DNA, or a detection of a cDNA obtained by using the mRNA as a template.

As a technique for detecting the FGFR3 fusion gene (genomic DNA or mRNA) or the TACC3 fusion gene (genomic DNA or mRNA) in the sample obtained from a subject, any technique, well-known by those skilled in the art, used in the detection of a gene, for example, a hybridization technique using a probe (a nucleic acid probe or the like) which hybridizes to at least a portion of the FGFR3 fusion gene or the TACC3 fusion gene, a gene amplification technique using primers which anneal to at least a portion of the FGFR3 fusion gene or the TACC3 fusion gene, or the like, and a technique obtained by modifying these techniques, can be used.

More particularly, any technique, for example, PCR, LCR (Ligase chain reaction), SDA (Strand displacement amplification), NASBA (Nucleic acid sequence-based amplification), ICAN (Isothermal and chimeric primer-initiated amplification of nucleic acids), an LAMP (Loop-mediated isothermal amplification) method, a TMA method (Gen-Probe's TMA system), an in situ hybridization method, a microarray method, Northern hybridization, Southern hybridization, a dot blot method, an RNA protection method, DNA sequencing, RNA sequencing, or the like, can be used.

[Detection of Genomic DNA]

The in situ hybridization technique may be preferably used in the detection of genomic DNA. The detection utilizing the in situ hybridization technique may be carried out, for example, in accordance with a known FISH method, or by a fusion assay, which is a combination of a chromogenic in situ hybridization (CISH) method and a silver in situ hybridization (SISH) method. Preferably, it can be detected by a FISH method, split assay; or a FISH method, fusion assay, as described in detail below.

Alternatively, the DNA sequencing technique can be preferably used in the detection of genomic DNA. For the sequencing, a sequencer based on a conventional Sanger method may be used, but it is preferable to use a next-generation sequencer in view of the efficiency of the analysis (for example, see Metzker M L, Nat Rev Genet. 2010 January; 11(1): 31-46). As the next-generation sequencer, MiSeq/HiSeq (Illumina), SOLiD System (Life Technologies), 454 Sequence System (GS FLX+/GS Junior) (Roche), or the like, may be exemplified. In the sequencing, the efficiency of analysis can be improved by enriching the regions where the FGFR3 fusion gene or the TACC3 fusion gene might be present, using a sequence capture technique, or the like. As the sequence capture technique, Roche NimbleGen (Roche), Sure Select (Agilent Technologies), or the like, may be exemplified.

Hereinafter, typical methods for detecting genomic DNA will be exemplified, but the present invention is not limited to these methods.

<FISH Method, Split Assay>

In the FISH method, split assay for the FGFR3 fusion gene, a combination of a polynucleotide that covers the 5' terminal genomic region of the FGFR3 gene and is fluorescent-labeled, and another polynucleotide that covers the 3' terminal genomic region of the FGFR3 gene and is fluorescent-labeled with a different fluorescent dye is used as the probe for detection. In the normal case (in the case of the wild-type FGFR3 gene), since two gene regions (the 5' terminal region and the 3' terminal region of each gene) are adjacent to each other, two signals are detected as an overlapped color (for example, when a red fluorescent dye and a green fluorescent dye are used, yellow). On the other hand, in the case where two gene regions are cleaved due to translocation or inversion, two signals (for example, red and green) derived from the fluorescent dyes are detected separately and apart from each other. Therefore, in the FISH method, split assay, the presence of the FGFR3 fusion gene is detected by detecting the fact that the 5' terminal genomic region of the FGFR3 gene and the 3' terminal genomic region of the FGFR3 gene are apart from each other on a chromosome.

In the FISH method, split assay for the TACC3 fusion gene, a combination of a polynucleotide that covers the 5' terminal genomic region of the TACC3 gene and is fluorescent-labeled, and another polynucleotide that covers the 3' terminal genomic region of the TACC3 gene and is fluorescent-labeled with a different fluorescent dye is used as the probe for detection. In the normal case (in the case of the wild-type TACC3 gene), since two gene regions (the 5' terminal region and the 3' terminal region of each gene) are adjacent to each other, two signals are detected as an overlapped color (for example, when a red fluorescent dye and a green fluorescent dye are used, yellow). On the other hand, in the case where two gene regions are cleaved due to translocation or inversion, two signals (for example, red and green) derived from the fluorescent dyes are detected separately and apart from each other. Therefore, in the FISH method, split assay, the presence of the TACC3 fusion gene is detected by detecting the fact that the 5' terminal genomic region of the TACC3 gene and the 3' terminal genomic region of the TACC3 gene are apart from each other on a chromosome.

In the case where the FGFR3 fusion gene or the TACC3 fusion gene is the FGFR3-TACC3 fusion gene, the FGFR3-TACC3 fusion gene can be detected by using, as the probe for detection, a combination of a polynucleotide that covers the 5' terminal genomic region of the FGFR3 gene and is fluorescent-labeled, and another polynucleotide that covers the 3' terminal genomic region of the FGFR3 gene and is fluorescent-labeled with a different fluorescent dye, or a combination of a polynucleotide that covers the 5' terminal genomic region of the TACC3 gene and is fluorescent-labeled, and another polynucleotide that covers the 3' terminal genomic region of the TACC3 gene and is fluorescent-labeled with a different fluorescent dye.

<FISH Method, Fusion Assay>

In the FISH method, fusion assay for the FGFR3 fusion gene, for example, in the case where the FGFR3 fusion gene is the FGFR3-TACC3 fusion gene, a combination of a polynucleotide that covers the 5' terminal genomic region of the FGFR3 gene and is fluorescent-labeled, and another polynucleotide that covers the 3' terminal genomic region of the TACC3 gene and is fluorescent-labeled with a different fluorescent dye can be used as the probe for detection. In the normal case (in the case of the wild-type FGFR3 gene), two signals (for example, red and green) derived from the fluorescent dyes are detected separately and apart from each other. On the other hand, in the case where two gene regions are adjacent to each other due to translocation or inversion, two signals are detected as an overlapped color (for example, yellow).

In the FISH method, fusion assay for the TACC3 fusion gene, for example, in the case where the TACC3 fusion gene is the FGFR3-TACC3 fusion gene, a combination of a polynucleotide that covers the 5' terminal genomic region of the FGFR3 gene and is fluorescent-labeled, and another polynucleotide that covers the 3' terminal genomic region of the TACC3 gene and is fluorescent-labeled with a different fluorescent dye can be used as the probe for detection. In the normal case (in the case of the wild-type TACC3 gene), two signals (for example, red and green) derived from the fluorescent dyes are detected separately and apart from each other. On the other hand, in the case where two gene regions are adjacent to each other due to translocation or inversion, two signals are detected as an overlapped color (for example, yellow).

<Detection of Gene Duplication Using FISH Method>

With respect to a gene duplication associated with the construction of the FGFR3 fusion gene, for example, in the case where the FGFR3 fusion gene is the FGFR3-TACC3 fusion gene, a polynucleotide that covers at least a portion of the 5' terminal genomic region of the FGFR3 gene and fluorescent-labeled can be used as the probe for detection, as described in detail in Example 1 below. The FGFR3 fusion gene can be detected by detecting the fact that a strong signal (for example, two times or more) is obtained, in comparison with the case of the wild-type FGFR3 gene alone.

In connection with this, the FGFR3 fusion gene may be detected by this method, using a probe for detecting the 3' genomic region of another gene that constitutes the fusion gene by fusing it to a polynucleotide derived from the FGFR3 gene (for example, when the FGFR3 fusion gene is the FGFR3-TACC3 fusion gene, another gene is the TACC3 gene).

With respect to a gene duplication associated with the construction of the TACC3 fusion gene, for example, in the case where the TACC3 fusion gene is the FGFR3-TACC3 fusion gene, a polynucleotide that covers at least a portion of the 3' terminal genomic region of the TACC3 gene and is fluorescent-labeled, can be used as the probe for detection, as described in detail in Example 1 below. The TACC3 fusion gene can be detected by detecting the fact that a strong signal (for example, two times or more) is obtained, in comparison with the case of the wild-type TACC3 gene alone.

In connection with this, the TACC3 fusion gene may be detected by this method, using a probe for detecting the 5' genomic region of another gene that constitutes the fusion gene by fusing it to a polynucleotide derived from the TACC3 gene (for example, when the TACC3 fusion gene is the FGFR3-TACC3 fusion gene, another gene is the FGFR3 gene).

<Detection of Gene Duplication Using CGH Array Analysis>

The gene duplication associated with the construction of the FGFR3 fusion gene or the construction of the TACC3 fusion gene can be detected by a comparative genomic hybridization (CGH) array analysis (for example, Agilent CGH/CNV Array Analysis; Agilent Technologies).

<Detection of Gene Duplication Using Next-Generation Sequencer>

The gene duplication associated with the construction of the FGFR3 fusion gene or the construction of the TACC3 fusion gene can be detected by a next-generation sequencer. More particularly, the FGFR3 fusion gene or the TACC3 fusion gene can be detected by detecting the fact that the coverage of the gene duplication portion is high (the redundancy of the portion is high at the time of the annotation, using the sequence of a DNA fragment to be analyzed, as the reference sequence) in the analysis using a next-generation sequencer.

<Probe to be Used in Detection (for Genome)>

As the probe used in hybridization to detect the FGFR3 fusion gene, a probe that hybridizes to a polynucleotide of at least a portion of the FGFR3 fusion gene, or a complementary strand thereof, under stringent conditions (preferably, under more stringent conditions), is preferable.

For example, in the case where genomic DNA of the FGFR3 fusion gene containing the fusion point is detected, a probe comprising a nucleic acid molecule consisting of at least 32 consecutive nucleotides containing 16 nucleotides at the upstream and 16 nucleotides at the downstream, by which the fusion point of the FGFR3 fusion gene is sandwiched, or a probe comprising a complementary strand of the nucleic acid molecule, may be used.

As the probe used in hybridization to detect the TACC3 fusion gene, a probe that hybridizes to a polynucleotide of at least a portion of the TACC3 fusion gene, or a complementary strand thereof, under stringent conditions (preferably, under more stringent conditions), is preferable.

For example, in the case where genomic DNA of the TACC3 fusion gene containing the fusion point is detected, a probe comprising a nucleic acid molecule consisting of at least 32 consecutive nucleotides containing 16 nucleotides at the upstream and 16 nucleotides at the downstream, by which the fusion point of the TACC3 fusion gene is sandwiched, or a probe comprising a complementary strand of the nucleic acid molecule, may be used.

For example, in the case where the FGFR3 fusion gene or the TACC3 fusion gene is the FGFR3-TACC3 fusion gene, as the probe that can be used in the FISH method, fusion assay, a combination of the first probe that specifically recognizes the 5' terminal genomic region of either of the TACC3 gene or the FGFR3 gene, and the second probe that specifically recognizes the 3' terminal genomic region of the other (preferably, a combination of the first probe that specifically recognizes the 5' terminal genomic region of the FGFR3 gene, and the second probe that specifically recognizes the 3' terminal genomic region of the TACC3 gene) can be used.

On the other hand, for example, in the case where the FGFR3 fusion gene or the TACC3 fusion gene is the FGFR3-TACC3 fusion gene, as the probe that can be used in the FISH method, split assay, a combination of the first probe that specifically recognizes the 5' terminal genomic region of the FGFR3 gene, and the second probe that specifically recognizes the 3' terminal genomic region of the FGFR3 gene, or a combination of the first probe that specifically recognizes the 5' terminal genomic region of the TACC3 gene, and the second probe that specifically recognizes the 3' terminal genomic region of the TACC3 gene (preferably, a combination of the first probe that specifically recognizes the 5' terminal genomic region of the FGFR3 gene, and the second probe that specifically recognizes the 3' terminal genomic region of the FGFR3 gene) can be used.

[Detection of mRNA]

Detection of mRNA can be carried out by analyzing the mRNA per se using a Northern hybridization method or the like, or by analyzing a complementary DNA (cDNA), which is synthesized by a well-known method for those skilled in the art, using the mRNA as a template.

The detection of RNA can be carried out, preferably using a sequence technique. In view of the efficiency of analysis, it is preferable to use a next-generation sequencer in the sequencing (for example, see Metzker M L, Nat Rev Genet. 2010 January; 11(1): 31-46). As the next-generation sequencer, MiSeq/HiSeq (Illumina), SOLiD System (Life Technologies), 454 Sequence System (GS FLX+/GS Junior) (Roche), or the like, may be exemplified. In the sequencing, the efficiency of analysis can be improved by enriching the regions where the FGFR3 fusion gene might be present, using a gene amplification reaction method as described below, a sequence capture technique, or the like. As the sequence capture technique, Roche NimbleGen (Roche), Sure Select (Agilent Technologies), or the like, may be exemplified.

<Detection by Gene Amplification Reaction Method> mRNA can be detected by a gene amplification method, using primers designed so as to specifically amplify a polynucleotide of at least a portion of the FGFR3 fusion gene or the TACC3 fusion gene to be detected. Hereinafter typical methods for detecting mRNA will be exemplified, but the present invention is not limited to these methods.

==PCR Method==

For example, in the PCR method, a PCR product is analyzed by an agarose gel electrophoresis, and it can be confirmed whether or not an amplified fragment of the desired size can be obtained by an ethidium bromide staining or the like. When the amplified fragment of the desired size is obtained, it may be concluded that the FGFR3 fusion gene or the TACC3 fusion gene is present in a sample obtained from a subject. The FGFR3 fusion gene or the TACC3 fusion gene can be detected in this manner.

As the detection method of the FGFR3 fusion gene or the TACC3 fusion gene of the present invention, it is preferable that, in addition to the step of amplifying a specific polynucleotide by a gene amplification reaction in a sample obtained from a subject, it further comprises the step of detecting whether or not the amplified fragment of the desired size is obtained.

The PCR method is suitable to quantitatively detect the FGFR3 fusion gene or the TACC3 fusion gene.

Therefore, as previously described in <Embodiment of detecting FGFR3 fusion protein (1-b)>, the FGFR3 fusion gene can be detected by separately and specifically detecting the expression levels of the 5' terminal region and the 3' terminal region of the FGFR3 fusion gene, and calculating the ratio of the expression levels. Alternatively, the FGFR3 fusion gene can be detected by separately and specifically detecting the expression levels of the 5' terminal region and the 3' terminal region of the other gene (i.e., the gene other than the FGFR3 gene), which constitutes the FGFR3 fusion gene together with the FGFR3 gene, and calculating the ratio of the expression levels.

Further, as previously described in <Embodiment of detecting TACC3 fusion protein (1-b)>, the PCR method is preferably used in the method of detecting the TACC3 fusion gene by separately and specifically detecting the expression levels of the 5' terminal region and the 3' terminal region of the TACC3 fusion gene, and calculating the ratio of the expression levels. Alternatively, the TACC3 fusion gene can be detected by separately and specifically detecting the expression levels of the 5' terminal region and the 3' terminal region of the other gene (i.e., the gene other than the TACC3 gene), which constitutes the TACC3 fusion gene together with the TACC3 gene, and calculating the ratio of the expression levels.

With respect to the PCR method, and the method of designing primers used in this method, the methods can be carried out by those skilled in the art in accordance with known methods.

For example, a sense primer and an antisense primer that are designed so as to specifically amplify the 5' terminal region of the FGFR3 gene, and a sense primer and an antisense primer that are designed so as to specifically amplify the 3' terminal region of the FGFR3 gene, can be used.

For example, a sense primer and an antisense primer that are designed so as to specifically amplify the 5' terminal region of the TACC3 gene, and a sense primer and an antisense primer that are designed so as to specifically amplify the 3' terminal region of the TACC3 gene, can be used.

==Real-Time PCR Method==

Further, in the PCR method, a more quantitative analysis can be carried out in the detection of the FGFR3 fusion or the TACC3 fusion gene, by using a PCR amplification monitor (real-time PCR) method in the gene amplification step (Genome Res., 6(10), 986, 1996). As the PCR amplification monitor method, for example, ABI PRISM7900 (PE Biosystems) can be used. The real-time PCR is a known method, and apparatuses and kits for the method are commercially available, and it can be easily carried out using them.

More particularly, for example, in the case where the FGFR3 fusion gene is the FGFR3-TACC3 fusion gene and is detected using mRNA as an index, the sense primer (5'-primer, forward primer) is designed based on any portion derived from the FGFR3 gene, and the antisense primer (3'-primer, reverse primer) is designed based on any portion derived from the TACC3 gene.

In the case where the TACC3 fusion gene is the FGFR3-TACC3 fusion gene and is detected using mRNA as an index, the sense primer (5'-primer, forward primer) is designed based on any portion derived from the FGFR3 gene, and the antisense primer (3'-primer, reverse primer) is designed based on any portion derived from the TACC3 gene.

==Multiplex PCR==

In the PCR method for detecting the FGFR3 fusion gene, a Multiplex PCR, in which all of the fusion polynucleotides are detected using a single reaction solution, can be designed by mixing the above-mentioned sense primers corresponding to each of the other genes that constitute the FGFR3 fusion gene together with the FGFR3 gene, and corresponding to multiple fusion points.

In the PCR method for detecting the TACC3 fusion gene, a Multiplex PCR, in which all of the fusion polynucleotides are detected using a single reaction solution, can be designed by mixing the above-mentioned sense primers corresponding to each of the other genes that constitute the TACC3 fusion gene together with the TACC3 gene, and corresponding to multiple fusion points.

==Detection by Mass Spectrometry==

A mass spectrometric method disclosed in JP2012-100628A can be used in order to analyze amplified fragments in the detection methods using the above-mentioned gene amplification reaction methods.

==Primer Set Used in Detection==

The primer set used in the detection method for detecting the FGFR3 fusion gene of the present invention is not particularly limited, so long as at least a portion of the FGFR3 fusion gene to be detected can be specifically amplified, and the FGFR3 fusion gene can be detected. Those skilled in the art can design the primer set, based on the nucleotide sequence of the polynucleotide to be detected.

The primer set used in the detection method for detecting the TACC3 fusion gene of the present invention is not particularly limited, so long as at least a portion of the TACC3 fusion gene to be detected can be specifically amplified, and the TACC3 fusion gene can be detected. Those skilled in the art can design the primer set, based on the nucleotide sequence of the polynucleotide to be detected.

Primers used in the PCR amplification monitoring method can be designed using a primer design software (for example, Primer Express; PE Biosystems), or the like. Since when the size of the PCR product is increased, the amplification efficiency becomes poor, it is preferable that the sense primer and the antisense primer are designed so that the size of the amplified product obtained when mRNA or cDNA is amplified as the target is 1 kb or less.

<Detection by Hybridization Method> mRNA can be detected by a hybridization method using a probe that hybridizes to a polynucleotide of at least a portion of the FGFR3 fusion gene or the TACC3 fusion gene to be detected.

As the detection using the hybridization technique, Northern hybridization, dot blotting, a DNA microarray method, and an RNA protection method can be exemplified.

==Probe (for mRNA)==

As the probe used in hybridization, a probe that hybridizes to a polynucleotide of at least a portion of the FGFR3 fusion gene, or a complementary strand thereof, under stringent conditions (preferably, under more stringent conditions), is preferable.

<Detection of Fusion Protein>

Any technique that is well-known by those skilled in the art and is used in the analysis of proteins, or any technique that is obtained by applying these techniques can be used, as the technique of detecting the FGFR3 fusion protein or the TACC3 fusion protein in samples obtained from a subject.

For example, as the method of detecting the FGFR3 fusion protein, an immunological measurement method (an immunoassay), an enzyme activity measurement method (an ELISA), a two-antibodies sandwich ELISA, a fluorescence immunoassay, a radioimmunoassay, a Western blotting, an immunohistochemical method, an immunoprecipitation method, an intercalated antibody-enhanced polymer (iAEP) method, and a FRET method, using an antibody that specifically recognizes the FGFR3 protein, an antibody that specifically recognizes a protein that is other than FGFR3 and constitutes the FGFR3 fusion protein together with the FGFR3 protein, or an antibody that specifically recognizes the FGFR3 fusion protein, can be exemplified. Further, mass spectrometry or amino acid sequencing can either be used in combination with these methods or alone.

For example, as the method of detecting the TACC3 fusion protein, an immunological measurement method (an immunoassay), an enzyme activity measurement method (an ELISA), a two-antibodies sandwich ELISA, a fluorescence immunoassay, a radioimmunoassay, a Western blotting, an immunohistochemical method, an immunoprecipitation method, an intercalated antibody-enhanced polymer (iAEP) method, and a FRET method, using an antibody that specifically recognizes the TACC3 protein, an antibody that specifically recognizes a protein that is other than TACC3 and constitutes the TACC3 fusion protein together with the TACC3 protein, or an antibody that specifically recognizes the TACC3 fusion protein, can be exemplified. Further, mass spectrometry or amino acid sequencing can either be used in combination with these methods or alone.

Hereinafter typical methods for detecting proteins will be exemplified, but the present invention is not limited to these methods.

[Typical Techniques Used in Detection]

The above-mentioned known methods, such as the following methods, may be used as detection methods using antibodies.

<Immunohistochemical Method>

For example, in the case where the FGFR3 fusion protein or the TACC3 fusion protein to be detected is the FGFR3-TACC3 fusion protein, a tissue section potential for the presence of the fusion protein to be detected can be subjected to immunostaining, using an anti-FGFR3 antibody that binds to a polypeptide at the N-terminal region of the FGFR3 protein, and an anti-TACC3 antibody that binds to a polypeptide at the C-terminal region of the TACC3 protein, to detect the presence of the fusion protein to be detected, by confirming that these antibodies are adjacent to each other.

Alternatively, the tissue section can be subjected to immunostaining, using an antibody that specifically binds to a polypeptide at the N-terminal region of the FGFR3 protein, and an antibody that specifically binds to a polypeptide at the C-terminal region of the FGFR3 protein, to detect the presence of the fusion protein to be detected, by confirming that these antibodies are located apart from each other.

Alternatively, the tissue section can be subjected to immunostaining, using an antibody that specifically binds to a polypeptide at the N-terminal region of the TACC3 protein, and an antibody that specifically binds to a polypeptide at the C-terminal region of the TACC3 protein, to detect the presence of the fusion protein to be detected, by confirming that these antibodies are located apart from each other.

Alternatively, the tissue section can be subjected to immunostaining, using an antibody that specifically binds to a polypeptide containing the fusion point, to detect the presence of the fusion protein to be detected.

<Western Blotting>

For example, in the case where the FGFR3 fusion protein or the TACC3 fusion protein to be detected is the FGFR3-TACC3 fusion protein, a cell extract potential for the presence of the fusion protein to be detected is subjected to electrophoresis, which is well-known for those skilled in the art, to separate the proteins contained in the cell extract from each other, and the separated proteins are blotted on a membrane.

Next, the membrane on which the proteins are blotted can be subjected to immunostaining, using an anti-FGFR3 antibody that binds to a polypeptide at the N-terminal region of the FGFR3 protein, and an anti-TACC3 antibody that binds to a polypeptide at the C-terminal region of the TACC3 protein, to detect the presence of the fusion protein to be detected, by confirming that the anti-FGFR3 antibody and the anti-TACC3 antibody are bound to the desired site on the membrane.

Alternatively, an antibody that specifically binds to a polypeptide containing the fusion point can be used to detect the presence of the fusion protein to be detected, by confirming that the antibody is bound to the desired site on the membrane.

Alternatively, an anti-FGFR3 antibody can be used to detect the presence of the fusion protein to be detected, by confirming that the antibody is bound to the FGFR3-TACC3 fusion protein on the membrane. In connection with this, the presence of the fusion protein to be detected can be detected by confirming that the anti-FGFR3 antibody is bound to a site different from the predicted site of the wild-type FGFR3 protein on the membrane.

Alternatively, an anti-TACC3 antibody can be used to detect the FGFR3-TACC3 fusion protein, on the same principle as that in the case of using the anti-FGFR3 antibody.

<Immunoprecipitation>

For example, in the case where the FGFR3 fusion protein or the TACC3 fusion protein to be detected is the FGFR3-TACC3 fusion protein, a cell extract potential for the presence of the fusion protein to be detected can be subjected to immunoprecipitation, using either an anti-FGFR3 antibody that binds to a polypeptide at the N-terminal region of the FGFR3 protein, or an anti-TACC3 antibody that binds to a polypeptide at the C-terminal region of the TACC3 protein, to detect the presence of the fusion protein to be detected, by detecting the precipitate using another antibody. After the immunoprecipitation and the detection as described above, it is preferable to further detect that the detected polypeptide has the same size as that of the polypeptide to be detected of interest, using a detection antibody.

Alternatively, a cell extract potential for the presence of the FGFR3 fusion protein to be detected can be subjected to immunoprecipitation, using an anti-FGFR3 antibody that binds to a polypeptide at the N-terminal region of the FGFR3 protein, and the precipitate can be subjected to mass spectrometry, to detect the presence of the fusion protein to be detected, by confirming the presence of a protein that has a mass different from that of the wild-type FGFR3 and binds to the FGFR3 antibody.

Alternatively, a cell extract potential for the presence of the TACC3 fusion protein to be detected can be subjected to immunoprecipitation, using an anti-TACC3 antibody that binds to a polypeptide at the C-terminal region of the TACC3 protein, and the precipitate can be subjected to mass spectrometry, to detect the presence of the fusion protein to be detected, by confirming the presence of a protein that has a mass different from that of the wild-type TACC3 and binds to the TACC3 antibody.

[Antibody Used in Detection]

The antibodies used in the detection method of the present invention are not particularly limited, so long as they specifically bind to the desired sites of the FGFR3 fusion protein or the TACC3 fusion protein. The antibodies may be monoclonal antibodies or polyclonal antibodies, and may be used in combination thereof. The antibodies may be immunoglobulins per se, or antibody fragments that retain the antigen binding activity, such as Fab, Fab', F(ab')$_2$, or Fv. In order to detect the binding of antibodies, any labeling or any signal amplification method, which is well-known for those skilled in the art, can be used.

<Labeling Technique>

In the detection method of the gene (genomic DNA, mRNA, cDNA, or the like) or the protein, the labeling of a probe, primers, an amplified product, an antibody, or the like may be carried out using known techniques, for example, fluorescent labeling, chemiluminescent labeling, radioactive labeling, enzyme labeling, biotin labeling, avidin labeling, or the like.

In the detection method using a probe, the probe can be labeled by a known method, as described above. For example, when a labeled nucleic acid probe is prepared from a BAC clone, a known technique, such as a nick translation method, a random prime method, or the like, can be used. In connection with this, the probe can be biotin-labeled using biotin-dUTP (for example, manufactured by Roche Applied Science), and can be further treated with a fluorescent substance, a radioisotope, an enzyme, or the like, to which avidin is bound, to label the probe.

In the detection method using antibodies, the antibodies can be labeled by a known method, as described above. The following labeling methods can be exemplified.

[iAEP (Intercalated Antibody-Enhanced Polymer) Method]

The sensitivity in staining can be improved by intercalating an intervening antibody between the first antibody that binds to the protein to be detected, and a polymer reagent (Takeuchi et al., Clin Cancer Res, 2009 May 1; 15(9): 3143-3149).

[Fluorescence Resonance Energy Transfer (FRET)]

For example, a probe utilizing a FRET phenomenon (FRET probe) can be used as a technique for detecting the proximity of the two antibodies. In the case where one antibody is labeled with a donor fluorescent substance (CFP or the like), and another antibody is labeled with an acceptor fluorescent substance (YFP or the like), when both are sufficiently adjacent to each other, YFP becomes the excited state, due to the FRET phenomenon, and emits fluorescence when returning to the ground state. The proximity of the two antibodies can be detected by detecting this fluorescence.

<<Judgment of Subject to Whom Treatment with FGFR3 Inhibitor is Applied>>

In the case where the FGFR3 fusion gene or the FGFR3 fusion protein to be detected by the detection method of the present invention is detected in a sample obtained from a subject, the subject is a subject (patient) with an FGFR3 fusion-positive cancer, and a subject to whom a treatment with an FGFR3 inhibitor is applied.

<<Judgment of Subject to Whom Treatment with TACC3 Inhibitor is Applied>>

In the case where the TACC3 fusion gene or the TACC3 fusion protein to be detected by the detection method of the present invention is detected in a sample obtained from a subject, the subject is a subject (patient) with a TACC3 fusion-positive cancer, and a subject to whom a treatment with a TACC3 inhibitor is applied.

<<Kit for Detection>>

The kit for detection of the present invention includes a kit for detection of the FGFR3 fusion gene to be detected, and a kit for detection of the FGFR3 fusion protein to be detected.

The kit for detection of the present invention includes a kit for detection of the TACC3 fusion gene to be detected, and a kit for detection of the TACC3 fusion protein to be detected.

The kit for detection of the FGFR3 fusion gene to be detected of the present invention, or the kit for detection of the TACC3 fusion gene comprises the probe that can be used in the FISH method, fusion assay or the FISH method, split assay in the detection method of the present invention; or the sense and antisense primers that are designed so as to specifically amplify at least a portion of the FGFR3 fusion gene or the TACC3 fusion gene to be detected in the detection method of the present invention. The sense and antisense primer set is a set of polynucleotides that are at least portions of the FGFR3 fusion gene or the TACC3 fusion gene, and that function as amplification primers for the polynucleotide to be amplified.

The kit for detection of the FGFR3 fusion protein to be detected of the present invention, or the kit for detection of the TACC3 fusion protein comprises the antibody that can be used in the detection method of the present invention.

<Probe>

The detection kit for the FGFR3 fusion gene of the present invention can comprise one probe, or a combination of two or more probes that can hybridize to a polynucleotide of at least a portion of the FGFR3 fusion gene, or a complementary strand thereof under stringent conditions, and that can detect the FGFR3 fusion gene.

The detection kit for the TACC3 fusion gene of the present invention can comprise one probe, or a combination of two or more probes that can hybridize to a polynucleotide of at least a portion of the TACC3 fusion gene, or a complementary strand thereof under stringent conditions, and that can detect the TACC3 fusion gene.

As the probe, one or more probes previously described in <<Techniques used in detection method>> can be exemplified.

For example, in the case where the FGFR3 fusion gene or the TACC3 fusion gene is the FGFR3-TACC3 fusion gene, the kit can comprise either of one or more (preferably two or more) probes that hybridize to a polynucleotide derived from the FGFR3 gene, or one or more (preferably two or more) probes that hybridize to a polynucleotide derived from the TACC3 gene; both of one or more probes that hybridize to a polynucleotide derived from the FGFR3 gene, and one or more probes that hybridize to a polynucleotide derived from the TACC3 gene; or one or more probes that hybridize to a polynucleotide containing the fusion point of the FGFR3 gene, or one or more probes that hybridize to a polynucleotide containing the fusion point of the TACC3 gene.

<Primer Set>

The kit for detection of the FGFR3 fusion gene of the present invention can comprise one set of primers that can specifically amplify at least a portion of the FGFR3 fusion gene, and that can detect the FGFR3 fusion gene; or a combination of two sets or more thereof.

The kit for detection of the TACC3 fusion gene of the present invention can comprise one set of primers that can specifically amplify at least a portion of the TACC3 fusion gene, and that can detect the TACC3 fusion gene; or a combination of two sets or more thereof.

As the primer set, one or more primer sets previously described in <<Embodiments of detection method of the present invention>> or <<Techniques used in detection method>> can be exemplified.

The primer set of the present invention preferably includes:

(1) a primer set for detecting the fusion gene of the FGFR3 gene and the TACC3 gene, comprising a sense primer designed from a polynucleotide portion encoding the FGFR3 protein, and an anti sense primer designed from a polynucleotide portion encoding the TACC3 protein, wherein the antisense primer is composed of a nucleic acid molecule (preferably a nucleic acid molecule consisting of at least 16 nucleotides) that anneals to the "polynucleotide to be detected" under stringent conditions (preferably more stringent conditions), and the sense primer is composed of a nucleic acid molecule (preferably a nucleic acid molecule consisting of at least 16 nucleotides) that anneals to a complementary strand of the "polynucleotide to be detected" under stringent conditions (preferably more stringent conditions).

The primer set of the present invention includes the following primer sets (2) to (6), as more concrete embodiments of the above-mentioned primer set (1).

(2) A primer set comprising a sense primer consisting of at least 16 consecutive nucleotides in the region of nucleotides 1-2634, preferably nucleotides 1-2628, of SEQ ID NO: 1 (FGFR3ex18-TACC3ex4), and an antisense primer consisting of an oligonucleotide complementary to an oligonucleotide consisting of at least 16 consecutive nucleotides in the region of nucleotides 2629-5004, preferably nucleotides 2635-5004, of SEQ ID NO: 1.

(3) A primer set comprising a sense primer consisting of at least 16 consecutive nucleotides in the region of nucleotides 1-2634, preferably nucleotides 1-2628, of SEQ ID NO: 3 (FGFR3ex18-TACC3ex9), and an antisense primer consisting of an oligonucleotide complementary to an oligonucleotide consisting of at least 16 consecutive nucleotides in the region of nucleotides 2629-3561, preferably nucleotides 2635-3561, of SEQ ID NO: 3.

(4) A primer set comprising a sense primer consisting of at least 16 consecutive nucleotides in the region of nucleotides 1-2536 of SEQ ID NO: 5 (FGFR3ex17-TACC3ex11), and an antisense primer consisting of an oligonucleotide complementary to an oligonucleotide consisting of at least 16 consecutive nucleotides in the region of nucleotides 2537-3270 of SEQ ID NO: 5.

(5) A primer set for detecting the FGFR3 fusion gene of SEQ ID NOS: 1, 3, and 5, consisting of:

```
                                     (SEQ ID NO: 14)
fgfr3-1781-F: GTGAAGATGCTGAAAGACGATG (SEQ ID NO: 15)
tacc3-2559-R: GGTCAGCTCCTCGTTCTCTTTAG
```

(6) A primer set for detecting the FGFR3 fusion gene of SEQ ID NOS: 1, 3, and 5, consisting of:

```
                                     (SEQ ID NO: 7)
fgfr3-1990-F: CTACTCCTTCGACACCTGCAAG (SEQ ID NO: 8)
tacc3-2612-R: CCGTGGAGGTCAGATCTTCTC
```

(7) A primer set for detecting the FGFR3 fusion gene of SEQ ID NOS: 1, 3, and 5, consisting of the following sense primer, and an antisense primer which can be used in a 3'-RACE method together with the sense primer:

```
                                     (SEQ ID NO: 13)
fgfr3-2022-F: AGCAGCTCACCTTCAAGGACCTGG
```

The primer set of the present invention may be a primer set for detecting the expression levels of the 5' terminal region and the 3' terminal region of the FGFR3 gene, or a primer set for detecting the expression levels of the 5' terminal region and the 3' terminal region of the other gene, which constitutes the fusion gene together with the FGFR3 gene, as previously described in <Detection by gene amplification reaction method>, ==PCR method==.

As the primer set, the following primer sets (8) and (9) can be exemplified, for detecting the 5' terminal region and the 3' terminal region of the FGFR3 gene.

(8) A primer set for detecting of the 5' terminal region of the FGFR3 gene.

fgfr3-469-F: CACTGTCTGGGTCAAGGATG (SEQ ID NO: 9)

fgfr3-651-R: TCCCCGTCTTCGTCATCTC (SEQ ID NO: 10)

(9) A primer set for detecting of the 3' terminal region of the FGFR3 gene.

fgfr3-3213-F: CTGAAATTACGGGTACCTGAAG (SEQ ID NO: 11)

fgfr3-3352-R: TCCGTTGTACCAGCCTTTTC (SEQ ID NO: 12)

In these primer sets (1) to (9), it is preferable that the interval of the selected positions of the sense primer and the antisense primer is 1 kb or less, or that the size of the amplified product amplified by the sense primer and the antisense primer is 1 kb or less.

The primer of the present invention generally has a strand length of 15-40 nucleotides, preferably 16-24 nucleotides, more preferably 18-24, and most preferably 20-24.

The primer set of the present invention can be used in the amplification and detection of the polynucleotide to be detected, in the detection method of the present invention. Each primer contained in the primer set of the present invention is not particularly limited, but can be prepared by chemical synthesis.

<Antibody>

The kit for detection of the FGFR3 fusion protein of the present invention can comprise one antibody that specifically binds to any site of the FGFR3 fusion protein, or a combination of two or more thereof. More particularly, the antibodies described in <detection of fusion protein> can be exemplified.

The kit for detection of the TACC3 fusion protein of the present invention can comprise one antibody that specifically binds to any site of the TACC3 fusion protein, or a combination of two or more thereof. More particularly, the antibodies described in <detection of fusion protein> can be exemplified.

For example, in the case where the FGFR3 fusion protein or the TACC3 fusion protein is the FGFR3-TACC3 fusion protein, the kit can comprise either of one or more (preferably two or more) antibodies that bind to a polypeptide derived from the FGFR3 protein, or one or more (preferably two or more) antibodies that bind to a polypeptide derived from the TACC3 protein; both of one or more antibodies that bind to a polypeptide derived from the FGFR3 protein, and one or more antibodies that bind to a polypeptide derived from the TACC3 protein; or one or more antibodies that bind to a polypeptide containing the fusion point of the FGFR3 fusion protein, or one or more antibodies that bind to a polynucleotide containing the fusion point of the TACC3 fusion gene.

<<Screening Method of Inhibitor>>

<Step of Screening Substance that Inhibits Polypeptide>

According to the method for screening an inhibitor of the present invention, a substance that inhibits the polypeptide to be detected can be screened. The screening method comprises the steps of:

(1) bringing a test substance into contact with the polypeptide to be detected, or a cell expressing the polypeptide, (2) analyzing whether or not the polypeptide is inhibited, and (3) selecting a substance that inhibits the polypeptide.

The term "inhibition of the polypeptide" as used herein includes an inhibition of the activity of the polypeptide, and an inhibition of the expression of the polypeptide. The term "inhibition" means at least a part of inhibition.

<Step of Screening Inhibitor and Its Index>

The screening method of the present invention includes:

(A) a method in which a purified or crude polypeptide is used, and the inhibition of the activity of the polypeptide in vitro is regarded as an index;

(B) a method in which a cell expressing the polypeptide is used, and the inhibition of the activity of the polypeptide is regarded as an index; and (C) a method in which a cell expressing the polypeptide is used, and the inhibition of the expression of the polypeptide is regarded as an index.

[(A) A Method in which a Purified or Crude Polypeptide is Used, and the Inhibition of the Activity is Regarded as an Index]

The method (A) includes a method comprising the steps of: bringing a test substance into contact with the polypeptide in vitro; analyzing whether or not the activity of the polypeptide is inhibited by the test substance by comparing it with a control (a polypeptide with which the test substance is not brought into contact); and selecting the substance that inhibits the activity of the polypeptide.

The activity of the polypeptide in vitro can be measured using a known kinase activity assay. For example, the amount of ADP generated by the kinase reaction can be used as an index; a tyrosine phosphorylation level of the polypeptide can be used as an index; or a commercially available kinase activity assay kit can be used.

[(B) A Method in Which a Cell Expressing the Polypeptide is Used, and the Inhibition of the Activity is Regarded as an Index]

The method (B) includes a method comprising the steps of: bringing a test substance into contact with a cell expressing the polypeptide; analyzing whether or not the activity of the polypeptide is inhibited by the test substance by comparing it with a control (a cell with which the test substance is not brought into contact); and selecting the substance that inhibits the activity of the polypeptide.

The activity of the polypeptide in the cell can be measured using a known kinase activity assay. For example, the amount of ADP generated by the kinase reaction can be used as an index; a tyrosine phosphorylation level of the polypeptide can be used as an index; or a commercially available kinase activity assay kit can be used.

[(C) A Method in Which a Cell Expressing the Polypeptide is Used, and the Inhibition of the Expression is Regarded as an Index]

The method (C) includes a method comprising the steps of: bringing a test substance into contact with a cell expressing the polypeptide; analyzing whether or not the expression of the polypeptide is inhibited by the test substance by comparing it with a control (a cell with which the test substance is not brought into contact); and selecting the substance that inhibits the expression of the polypeptide.

The expression of the polypeptide in the cell can be analyzed by measuring the amount of the protein or mRNA. The amount of the protein can be measured by, for example, an ELISA method or immunoblotting. The amount of mRNA can be measured by, for example, an RT-PCR method or Northern blotting.

The FGFR3 fusion gene is a gene with oncogenic potential. Therefore, the polypeptide inhibitor, which is selected by the inhibitor screening method of the present invention, is useful as an active substance, or a candidate thereof, of a pharmaceutical composition for treating the FGFR3 fusion-positive cancer. The method of the present invention further comprises the step of confirming that the inhibitor has a therapeutic activity against the FGFR3 fusion-positive cancer, if desired.

The TACC3 fusion gene is a gene with oncogenic potential. Therefore, the polypeptide inhibitor, which is selected by the inhibitor screening method of the present invention, is useful as a therapeutic agent for the TACC3 fusion-positive cancer, or a candidate thereof. The method of the present invention further comprises the step of confirming that the inhibitor has a therapeutic activity against the TACC3 fusion-positive cancer, if desired.

The confirming step can be carried out using a known evaluation system, for example, an in vitro evaluation system using cultured cells, or a tumor-bearing animal model implanted with tumor cells.

The polypeptide-expressing cell can be obtained by introducing the polynucleotide of the present invention into a desired cell by a conventional method (see, for example, Molecular Cloning: A Laboratory Manual 4th Edition (2012), Cold Spring Harbor Laboratory Press). More particularly, for example, cDNA, which is the FGFR3 fusion gene or the TACC3 fusion gene of the present invention, is introduced into a recombinant vector, and the resulting DNA construct is introduced into cells to obtain the polypeptide-expressing cells (transformed cells).

<<Pharmaceutical Composition for Treating Cancer Containing Inhibitor>>

The pharmaceutical composition for treating an FGFR3 fusion-positive cancer (for example, a uterine cancer) of the present invention comprises the inhibitor against the FGFR3 fusion gene or its transcript. For example, the pharmaceutical composition contains, as the active ingredient, the inhibitor (for example, low molecular weight compounds, double-stranded nucleic acids (including siRNA), proteins (including an antibody or antibody fragment), peptides, or other compounds), which is obtained by the inhibitor screening method of the present invention, and further contains a pharmaceutically acceptable carrier, if desired.

The pharmaceutical composition for treating a TACC3 fusion-positive cancer (for example, digestive system cancer) of the present invention comprises the inhibitor against the TACC3 fusion gene or its transcript. For example, the pharmaceutical composition contains, as the active ingredient, the inhibitor (for example, low molecular weight compounds, double-stranded nucleic acids (including siRNA), proteins (including an antibody or antibody fragment), peptides, or other compounds), which is obtained by the inhibitor screening method of the present invention, and further contains a pharmaceutically acceptable carrier, if desired.

<Inhibitor Against FGFR3 Fusion Gene or its Transcript, or TACC3 Fusion Gene or Its Transcript>

Examples of the inhibitor against the FGFR3 fusion gene or its transcript include a kinase inhibitor (for example, an inhibitor for FGFR3), and an inhibitor against another gene that constitutes the fusion gene together with the FGFR3 gene, or its transcript.

Examples of the inhibitor against the TACC3 fusion gene or its transcript include a kinase inhibitor (for example, an inhibitor for TACC3), and an inhibitor against another gene that constitutes the fusion gene together with the TACC3 gene, or its transcript.

[Low Molecular Weight Compounds]

Among inhibitors, examples of the low molecular weight compound include:

LY287455 ((R)-(E)-2-(4-(2-(5-(1-(3,5-Dichloropyridin-4-yl)ethoxy)-1H-indazol-3yl)vinyl)-1H-pyrazol-1-yl)ethanol, Zhao G et al. Mol Cancer Ther. 2011 November; 10(11): 2200-2010);

PD173074 (1-tert-butyl-3-[6-(3,5-dimethoxy-phenyl)-2-(4-diethylamino-butylamino)-pyrido[2,3-d]pyrimidin-7-yl]-urea, Miyake M et al. J Pharmacol Exp Ther. 2010 March; 332(3): 795-802);

SU5402 (3-[(3-(2-carbox-yethyl)-4-methylpyrrol-2-yl) methylene]-2-indolinone), Grand E K et al. Leukemia. 2004 May; 18(5): 962-966);

Dovitinib (TKI-258, CHI-258, 4-amino-5-fluoro-3-[6-(4-methylpiperazin-1-yl)-1H-benzimidazole-2-yl]quinolin-2 (1H)-one, Trudel S et al. Blood. 2005 Apr. 1; 105(7): 2941-2948);

masitinib (4-[(4-methylpiperazin-1-yl)methyl]-N-(4-methyl-3-{[4-(pyridin-3-yl)-1,3-thiazol-2-yl] amino}phenyl)benzamide, Dubreuil P et al. PLoS One. 2009 Sep. 30; 4(9): e7258);

Ponatinib (3-[2-(imidazo[1,2-b]pyridazin-3-yl)ethynyl]-4-methyl-N-{4-[(4-methylpiperazin-1-yl)methyl]-3-(trifluoromethyl)phenyl}benzamide, Katoh, M. and Nakagama, H. Med. Res. Rev. 2013 May. doi: 10.1002/med.21288);

TAS-2985 (Taiho Pharmaceutical Co Ltd);

JNJ-42756493 (Janssen Biotech Inc);

Lenvatinib (4-{3-chloro-4-[(cyclopropylcarbamoyl) amino]phenoxy}-7-methoxyquinoline-6-carboxamide);

BGJ-398 (3-(2,6-dichloro-3,5-dimethoxy-phenyl)-1-{6-[4-(4-ethyl-piperazin-1-yl)-phenylamino]-pyrimidin-4-yl}-1-methyl-urea, Cheng T et al. PLoS One. 2013; 8(2): e57284);

AZD-4547 (N-[5-[2-(3,5-Dimethoxyphenyl)ethyl]-2H-pyrazol-3-yl]-4-(3,5-diemthylpiperazin-1-yl)benzamide, Gavine P R et al. Cancer Res. 2012 Apr. 15; 72(8): 2045-2056);

KHS-101 (N4-isobutyl-N2-((2-phenylthiazol-4-yl) methyl)pyrimidine-2,4-diamine, Sigma-Aldrich, Wurdak H. et al., Proc Natl Acad Sci USA. 2010 Sep. 21; 107(38): 16542-7); and pharmaceutically acceptable salts of these compounds.

[Double-Stranded Nucleic Acids]

The double-stranded nucleic acid is composed of a double-stranded nucleic acid (RNA or DNA) portion, and preferably overhangs at the 3' terminus of the sense strand and the antisense strand, and induces RNAi. RNAi is an evolutionally conserved phenomenon, and occurs through the double-stranded nucleic acid consisting of 21-23 nucleotides, which is generated by RNase III endonuclease (Genes Dev. 15, 485-490, 2001). The overhangs at the 3' terminus are nucleic acids consisting of one or two arbitrary nucleotides, and two nucleotides are preferable. In connection with this, the number of nucleotides (21-23 nucleotides) means the number of nucleotides that constitute the sense strand or the antisense strand including each overhang. The nucleotide numbers in the sense strand and the antisense strand may be the same or different, and are preferably the same.

The ribonucleic acids, which constitute the overhangs at the 3'-terminus of the double-stranded nucleic acid, may be, for example, U (uridine), A (adenosine), G (guanosine), or C (cytidine). The deoxyribonucleic acids, which constitute the overhangs at the 3'-terminus, may be, for example, dT (deoxythymidine), dA (deoxyadenosine), dG (deoxyguanosine), or dC (deoxycytidine).

The double-stranded nucleic acid, which may be used as the active ingredient of the pharmaceutical composition of the present invention, is not particularly limited, so long as it has the inhibitory activity against the FGFR3 fusion gene, or the inhibitory activity against the TACC3 fusion gene. For example, it can be designed on the basis of the nucleotide sequence of a polynucleotide, in which the double-stranded portion contains a fusion point, such as a nucleotide sequence containing nucleotides 2628-2635 of SEQ ID NO: 1, a nucleotide sequence containing nucleotides 2628-2635 of SEQ ID NO: 3, or a nucleotide sequence containing nucleotides 2536-2537 of SEQ ID NO: 5. Alternatively, it can be designed on the basis of the nucleotide sequence of a polynucleotide, in which the double-stranded portion encodes the kinase portion. The double-stranded nucleic acid of the present invention can be prepared by a conventional method (for example, J. Am. Chem. Soc., 120, 11820-11821, 1998; and Methods, 23, 206-217, 2001). Companies which manufacture double-stranded nucleic acids under contract (for example, RNAi Inc.) are well-known to those skilled in the art, and can be used in the preparation of double-stranded nucleic acid. Double-stranded nucleic acid can be designed by an siRNA sequence design system (siDirect (trademark), RNAi Inc.)

[Proteins and Antibodies]

The antibody, which may be used as the active ingredient of the pharmaceutical composition of the present invention, is not particularly limited, so long as it can inhibit a transcript of the FGFR3 fusion gene or a transcript of the TACC3 fusion gene, preferably a transcript of the FGFR3-TACC3 gene. For example, an antibody that inhibits the activity (preferably kinase activity) of the FGFR3 fusion protein or the TACC3 fusion protein can be exemplified.

EXAMPLES

The present invention now will be further illustrated by, but is by no means limited to, the following Examples.

In the case where there is no explanation in DESCRIPTION OF EMBODIMENTS and EXAMPLES, methods described in standard protocols, such as J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd.; and the like, or variations or modifications thereof may be used. In the case where commercially available reagent kits or measurement apparatus, protocols attached thereto may be used, unless otherwise specified.

[Example 1] Detection of Genetic Abnormalities by FISH Method in Clinical Specimens Genetic abnormalities were detected by a FISH method in clinical specimens. Surgically-removed, and 20% formalin-fixed, paraffin-embedded uterine cancer tissues were sliced at a thickness of 4 and placed on slides to prepare pathological sections. The FISH method was carried out in accordance with the method described in a reference (Takeuchi K, Choi Y L, Soda M, Inamura K, Togashi Y, Hatano S, Enomoto M, Takada S, Yamashita Y, Satoh Y, Okumura S, Nakagawa K, Ishikawa Y, Mano H. Multiplex reverse transcription-PCR screening for EML4-ALK fusion transcripts. Clin Cancer Res. 2008; 14: 6618-6624.). The prepared, unstained sections were treated using a Histology FISH accessory kit (Dako), and then were hybridized with a BAC (bacterial artificial chromosome) clone (clone No. RP11-585J22), which covered the 5' terminal region of the FGFR3 gene and was fluorescent-labeled with red (Texas-Red), and a BAC clone (clone No. RP11-241P10, RP11-262P20), which covered the 3' terminal region of the FGFR3 gene and was fluorescent-labeled with green (FITC). The sections were further stained with 4,6-diamino-2-phenylindole. A fluorescence microscopy BX51 (Olympus Corporation) was used for fluorescence observation. From the examination of about 240 cases of pathological specimens, 1 specimen case (derived from a patient with cervical cancer) that suggested the genomic structural abnormalities in the FGFR3 gene region, in which a strong green signal (FITC) was observed in comparison with the wild-type FGFR3 gene region not having structural abnormalities, was found. Further, it was suggested from the detected signal pattern that the genomic structural abnormalities in the FGFR3 gene region was accompanied by a duplication of the FGFR3 gene on the same chromosome.

[Example 2] Detection of FGFR3 Fusion Gene (RT-PCR (1))

The fusion gene was detected by an RT-PCR, by which the region containing the fusion point was directly amplified, and it was shown that the fusion gene was present in the cancer tissue. More particularly, cDNA was synthesized from an RNA template derived from the specimen, in which the genomic structural abnormalities in the FGFR3 gene region were suggested in Example 1. A PCR was carried out using the cDNA, as well as a sense primer fgfr3-1990-F (SEQ ID NO: 7, Table 1) designed on the FGFR3 gene and an antisense primer TACC3-2612-R (SEQ ID NO: 8, Table 1) designed on the TACC3 gene.

As a result, amplified products having different sizes of about 3000 bp and about 1500 bp were obtained, and the presence of a fusion gene of the FGFR3 gene and the TACC3 gene, and the presence of plural variants were suggested.

These DNA fragments were purified and subjected to TA cloning (pT7Blue-2) in accordance with a conventional method, and the sequences were analyzed. As a result, it was revealed that a portion of the FGFR3 gene containing its kinase region was fused to a 3' terminal portion of the TACC3 gene. Further, it was revealed that the fusions were generated between exon 18 of the FGFR3 gene and exon 4 of the TACC3 gene, or between exon 18 of the FGFR3 gene and exon 9 of the TACC3 gene.

[Example 3] Identification of FGFR3 Fusion Gene (3'-RACE)

With respect to about 240 cases of the pathological specimens used in Example 1, a real-time PCR method was carried out using a primer set of a sense primer fgfr3-469-F (SEQ ID NO: 9) and an antisense primer fgfr3-651-R (SEQ ID NO: 10) for the 5' terminal region of the FGFR3 gene, and a primer set of a sense primer fgfr3-3213-F (SEQ ID NO: 11) and an antisense primer fgfr3-3352-R (SEQ ID NO: 12) for the 3' terminal region of the FGFR3 gene, respectively, and the difference in expression level was compared. As a result, plural specimens in which the expression level of the 5' terminal region of the FGFR3 gene was higher than that of the 3' terminal region of the FGFR3 gene were detected. From the specimens, 5 cases in which the expression level of the 5' terminal region of the FGFR3 gene was extremely higher than that of the 3' terminal region of the FGFR3 gene were selected, and RNAs derived from these tissues were used as templates to analyze a gene that was present at the 3' terminus of the kinase region of the FGFR3 gene, in accordance with a protocol attached to a 3'-RACE kit (SMARTer (registered trademark) RACE cDNA Amplification Kit; Clonetech).

More particularly, the first strand cDNA was synthesized using 0.5 µg of RNA derived from clinical specimens. Next, the 3'-RACE (rapid amplification of cDNA ends) PCR was carried out using a UPM primer, which was contained in the kit, a sense primer (SEQ ID NO: 13), and DNA polymerase (AmpliTaq Gold (registered trademark); Life Technologies Japan The resulting RACE products were electrophoresed, and DNA fragments of around 1-2 kbp were purified. After TA cloning was carried out in accordance with a conventional method, and the sequences were analyzed using MiSeq (Illumina). As a result, it was revealed that a 5' terminal portion of the FGFR3 gene containing its kinase region was fused to a 3' terminal portion of the TACC3 gene.

Further, it was revealed that the fusions were generated between exon 18 of the FGFR3 gene and exon 4 of the TACC3 gene (SEQ ID NO: 1, FGFR3ex18-TACC3ex4, variant 1), between exon 18 of the FGFR3 gene and exon 9 of the TACC3 gene (SEQ ID NO: 3, FGFR3ex18-TACC3ex9, variant 2), or between exon 17 of the FGFR3 gene and exon 11 of the TACC3 gene (SEQ ID NO: 5, FGFR3ex17-TACC3ex11, variant 3).

In FGFR3ex18-TACC3ex4, FGFR3 was to the 92nd nucleotide of exon 18 (not containing the remaining 1665 nucleotides of exon 18), followed by an insertion of 6 nucleotides, which was fused to the head of exon 4 of TACC3. In FGFR3ex18-TACC3ex9, FGFR3 was to the 92nd nucleotide of exon 18 (not containing the remaining 1665 nucleotides of exon 18), followed by an insertion of 6 nucleotides, which was fused to the head of exon 9 of TACC3. In FGFR3ex17-TACC3ex11, FGFR3 was to the end of exon 17, which was fused to the head of exon 11 of TACC3.

[Example 4] Detection of FGFR3 Fusion Gene (RT-PCR (2))

mRNAs were collected from 4 specimens containing three kinds of variants (FGFR3ex18-TACC3ex4, FGFR3ex18-TACC3ex9, and FGFR3ex17-TACC3ex11), in which the presence of FGFR3-TACC3 fusion genes was confirmed in Example 3, and RT-PCR was carried out using a primer pair of a sense primer fgfr3-1781-F (SEQ ID NO: 14, Table 1) designed on the FGFR3 gene, and an antisense primer tacc3-2559-R (SEQ ID NO: 15, Table 1) designed on the TACC3 gene.

As a result, PCR-amplified products having lengths (3024 bp, 1581 bp, and 1290 bp) corresponding to the three kinds of variants were obtained. Accordingly, it was revealed that the variants of the FGFR3-TACC3 fusion gene, preferably three variants of FGFR3ex18-TACC3ex4, FGFR3ex18-TACC3ex9, and FGFR3ex17-TACC3ex11, can be detected by PCR, using the above-mentioned primer pair.

The presence of these fusion genes and their transcriptional products in a female genital cancer had not been reported, and it was shown for the first time. Further, the presence of the FGFR3 fusion genes and their transcriptional products in a female genital cancer had not been reported, and it was shown for the first time.

With respect to the fusion gene, transformation in transduced cells, and oncogenic potential in transduced-cell-transplanted mice were shown, and it is suggested that the presence of the fusion gene or its transcriptional product is a cause of cancer in the expression site (see Non-patent literature 1).

TABLE 1

| Primer | Sequence (5' → 3') | SEQ ID NO: (*1) |
|---|---|---|
| fgfr3-1990-F | CTACTCCTTCGACACCTGCAAG | 7 RT-PCR(1) |
| tacc3-2612-R | CCGTGGAGGTCAGATCTTCTC | 8 RT4CR(1) |
| fgfr3-469-F | CACTGTCTGGGTCAAGGATG | 9 Real-time PCR |
| fgfr3-651-R | TCCCCGTCTTCGTCATCTC | 10 Real-time PCR |
| fgfr3-3213-F | CTGAAATTACGGGTACCTGAAG | 11 Real-time PCR |
| fgfr3-3352-R | TCCGTTGTACCAGCCTTTTC | 12 Real-time PCR |
| fgfr3-2022-F | AGCAGCTCACCTTCAAGGACCTGG | 13 3'-RACE |
| fgfr3-1781-F | GTGAAGATGCTGAAAGACGATG | 14 RT-PCR(2) |
| tacc3-2559-R | GGTCAGCTCCTCGTTCTCTTTAG | 15 RT-PCR(2) |

(*1): Detection techniques in Examples

As described above, it was revealed in the present invention that the fusion gene of the FGFR3 gene was present in some of patients with a female genital cancer, and the fusion gene was a cause of cancer. Namely, it was clarified that cancer patients to be treated with an FGFR3 inhibitor could be selected by detecting the FGFR3 fusions, i.e., the FGFR3 fusion gene and its transcriptional product, preferably FGFR3ex18-TACC3ex4, FGFR3ex18-TACC3ex9, and FGFR3ex17-TACC3ex11, and their transcriptional products.

INDUSTRIAL APPLICABILITY

The detection method of the present invention is useful in the judgment of FGFR3 fusion-positive cancer patients. The detection kit and the primer set of the present invention can be used in the detection method. The inhibitor screening method of the present invention can be used in the screening of drugs effective for the treatment of the FGFR3 fusion-positive cancer patients. The drugs obtained by the screening can be used as the active ingredient for a pharmaceutical composition for the treatment of the FGFR3 fusion-positive cancer. It is possible to treat the cancer by administering the drug to a patient, who has been judged to be the FGFR3 fusion-positive cancer patient by the detection method.

Although the present invention has been described with reference to specific embodiments, various changes and modifications obvious to those skilled in the art are possible without departing from the scope of the appended claims.

FREE TEXT IN SEQUENCE LISTING

The nucleotide sequences of SEQ ID NOS: 7 to 15 in the sequence listing are synthetic primer sequences.

The invention claimed is:

1. A method for detecting a fusion protein of a Fibroblast Growth Factor Receptor 3 (FGFR3) protein and a Transforming, Acidic Coiled-coil Containing protein 3 (TACC3) protein, or a fusion gene encoding the fusion protein, said method comprising:
   obtaining a cervical squamous epithelial tissue sample from a subject; and
   detecting whether the fusion protein or the fusion gene is present in the cervical squamous epithelial tissue sample by:
   (a) using a first probe that specifically hybridizes to the 5' terminal region of an FGFR3 gene, and a second probe that specifically hybridizes to the 3' terminal region of a TACC3 gene, and detecting that the two gene regions are adjacent to each other on a chromosome;
   (b) using a first primer that specifically anneals to the 5' terminal region of the FGFR3 gene, and a second primer that specifically anneals to the 3' terminal region of the TACC3 gene, and confirming that a desired PCR product showing the presence of a fusion point can be obtained;
   (c) using a first antibody that specifically binds to the N-terminal region of the FGFR3 protein, and a second antibody that specifically binds to the C-terminal region of the TACC3 protein, and confirming that the two regions are present in the same protein; or
   (d) an immunoassay using an antibody that specifically recognizes a polypeptide containing a fusion point of the fusion protein,
   wherein the fusion protein is selected from the group consisting of:
   (i) a fusion protein in which the last exon of an FGFR3 protein portion is exon 18 of the FGFR3 protein, and the first exon of a TACC3 protein portion is exon 4 of the TACC3 protein;
   (ii) a fusion protein in which the last exon of an FGFR3 protein portion is exon 18 of the FGFR3 protein, and the first exon of a TACC3 protein portion is exon 9 of the TACC3 protein; and
   (iii) a fusion protein in which the last exon of an FGFR3 protein portion is exon 17 of the FGFR3 protein, and the first exon of a TACC3 protein portion is exon 11 of the TACC3 protein.

2. The method of claim 1, wherein the fusion protein is a polypeptide selected from the group consisting of:
   (a) a polypeptide consisting of the amino acid sequence of SEQ ID NO: 2,
   (b) a polypeptide consisting of the amino acid sequence of SEQ ID NO: 4, (c) a polypeptide consisting of the amino acid sequence of SEQ ID NO: 6, and
(d) a polypeptide with oncogenic potential comprising the amino acid sequence of SEQ ID NO: 2, SEQ ID NO: 4, or SEQ ID NO: 6.

3. The method of claim 1, wherein the fusion gene is a polynucleotide encoding the polypeptide selected from the group consisting of:
(a) a polypeptide consisting of the amino acid sequence of SEQ ID NO: 2,
(b) a polypeptide consisting of the amino acid sequence of SEQ ID NO: 4,
(c) a polypeptide consisting of the amino acid sequence of SEQ ID NO: 6, and
(d) a polypeptide with oncogenic potential comprising the amino acid sequence of SEQ ID NO: 2, SEQ ID NO: 4, or SEQ ID NO: 6.

4. The method of claim 1, wherein the fusion gene is DNA or mRNA.

5. The method of claim 1, wherein the fusion protein is a polypeptide selected from the group consisting of:
(a) a polypeptide consisting of the amino acid sequence of SEQ ID NO: 2,
(b) a polypeptide consisting of the amino acid sequence of SEQ ID NO: 4, and
(c) a polypeptide with oncogenic potential comprising the amino acid sequence of SEQ ID NO: 2 or SEQ ID NO: 4.

6. The method of claim 1, wherein the FGFR3 fusion gene is a polynucleotide encoding the polypeptide selected from the group consisting of:
(a) a polypeptide consisting of the amino acid sequence of SEQ ID NO: 2,
(b) a polypeptide consisting of the amino acid sequence of SEQ ID NO: 4, and
(c) a polypeptide with oncogenic potential comprising the amino acid sequence of SEQ ID NO: 2 or SEQ ID NO: 4.

* * * * *

SEQUENCE LISTING

<160> NUMBER OF SEQ ID NOS: 15

<210> SEQ ID NO 1
<211> LENGTH: 5004
<212> TYPE: DNA
<213> ORGANISM: Homo sapiens
<220> FEATURE:
<221> NAME/KEY: CDS
<222> LOCATION: (257)..(4846)

<400> SEQUENCE: 1

```
gtcgcgggca gctggcgccg cgcggtcctg ctctgccggt cgcacggacg caccggcggg      60
ccgccggccg gagggacggg gcgggagctg ggcccgcgga cagcgagccg gagcgggagc     120
cgcgcgtagc gagccgggct ccggcgctcg ccagtctccc gagcggcgcc cgcctcccgc     180
cggtgcccgc gccgggccgt gggggggcagc atgcccgcgc gcgctgcctg aggacgccgc     240 ggccccgcc cccgcc atg ggc gcc cct gcc tgc gcc ctc gcg ctc tgc gtg     292
            Met Gly Ala Pro Ala Cys Ala Leu Ala Leu Cys Val
             1               5                  10 gcc gtg gcc atc gtg gcc ggc gcc tcc tcg gag tcc ttg ggg acg gag     340
Ala Val Ala Ile Val Ala Gly Ala Ser Ser Glu Ser Leu Gly Thr Glu
             15                  20                  25 cag cgc gtc gtg ggg cga gcg gca gaa gtc ccg ggc cca gag ccc ggc     388
Gln Arg Val Val Gly Arg Ala Ala Glu Val Pro Gly Pro Glu Pro Gly
 30                  35                  40 cag cag gag cag ttg gtc ttc ggc agc ggg gat gct gtg gag ctg agc     436
Gln Gln Glu Gln Leu Val Phe Gly Ser Gly Asp Ala Val Glu Leu Ser
 45                  50                  55                  60 tgt ccc ccg ccc ggg ggt ggt ccc atg ggg ccc act gtc tgg gtc aag     484
Cys Pro Pro Pro Gly Gly Gly Pro Met Gly Pro Thr Val Trp Val Lys
                 65                  70                  75 gat ggc aca ggg ctg gtg ccc tcg gag cgt gtc ctg gtg ggg ccc cag     532
Asp Gly Thr Gly Leu Val Pro Ser Glu Arg Val Leu Val Gly Pro Gln
             80                  85                  90 cgg ctg cag gtg ctg aat gcc tcc cac gag gac tcc ggg gcc tac agc     580
Arg Leu Gln Val Leu Asn Ala Ser His Glu Asp Ser Gly Ala Tyr Ser
         95                  100                 105 tgc cgg cag cgg ctc acg cag cgc gta ctg tgc cac ttc agt gtg cgg     628
Cys Arg Gln Arg Leu Thr Gln Arg Val Leu Cys His Phe Ser Val Arg
     110                 115                 120 gtg aca gac gct cca tcc tcg gga gat gac gaa gac ggg gag gac gag     676
Val Thr Asp Ala Pro Ser Ser Gly Asp Asp Glu Asp Gly Glu Asp Glu
125                 130                 135                 140 gct gag gac aca ggt gtg gac aca ggg gcc cct tac tgg aca cgg ccc     724
Ala Glu Asp Thr Gly Val Asp Thr Gly Ala Pro Tyr Trp Thr Arg Pro
                 145                 150                 155 gag cgg atg gac aag aag ctg ctg gcc gtg ccg gcc gcc aac acc gtc     772
Glu Arg Met Asp Lys Lys Leu Leu Ala Val Pro Ala Ala Asn Thr Val
             160                 165                 170 cgc ttc cgc tgc cca gcc gct ggc aac ccc act ccc tcc atc tcc tgg     820
Arg Phe Arg Cys Pro Ala Ala Gly Asn Pro Thr Pro Ser Ile Ser Trp
         175                 180                 185 ctg aag aac ggc agg gag ttc cgc ggc gag cac cgc att gga ggc atc     868
Leu Lys Asn Gly Arg Glu Phe Arg Gly Glu His Arg Ile Gly Gly Ile
     190                 195                 200 aag ctg cgg cat cag cag tgg agc ctg gtc atg gaa agc gtg gtg ccc     916
Lys Leu Arg His Gln Gln Trp Ser Leu Val Met Glu Ser Val Val Pro
205                 210                 215                 220 tcg gac cgc ggc aac tac acc tgc gtc gtg gag aac aag ttt ggc agc     964
Ser Asp Arg Gly Asn Tyr Thr Cys Val Val Glu Asn Lys Phe Gly Ser
```

```
                        225                 230                 235
atc cgg cag acg tac acg ctg gac gtg ctg gag cgc tcc ccg cac cgg       1012
Ile Arg Gln Thr Tyr Thr Leu Asp Val Leu Glu Arg Ser Pro His Arg
            240                 245                 250 ccc atc ctg cag gcg ggg ctg ccg gcc aac cag acg gcg gtg ctg ggc       1060
Pro Ile Leu Gln Ala Gly Leu Pro Ala Asn Gln Thr Ala Val Leu Gly
        255                 260                 265 agc gac gtg gag ttc cac tgc aag gtg tac agt gac gca cag ccc cac       1108
Ser Asp Val Glu Phe His Cys Lys Val Tyr Ser Asp Ala Gln Pro His
    270                 275                 280 atc cag tgg ctc aag cac gtg gag gtg aat ggc agc aag gtg ggc ccg       1156
Ile Gln Trp Leu Lys His Val Glu Val Asn Gly Ser Lys Val Gly Pro
285                 290                 295                 300 gac ggc aca ccc tac gtt acc gtg ctc aag tcc tgg atc agt gag agt       1204
Asp Gly Thr Pro Tyr Val Thr Val Leu Lys Ser Trp Ile Ser Glu Ser
            305                 310                 315 gtg gag gcc gac gtg cgc ctc cgc ctg gcc aat gtg tcg gag cgg gac       1252
Val Glu Ala Asp Val Arg Leu Arg Leu Ala Asn Val Ser Glu Arg Asp
        320                 325                 330 ggg ggc gag tac ctc tgt cga gcc acc aat ttc ata ggc gtg gcc gag       1300
Gly Gly Glu Tyr Leu Cys Arg Ala Thr Asn Phe Ile Gly Val Ala Glu
    335                 340                 345 aag gcc ttt tgg ctg agc gtt cac ggg ccc cga gca gcc gag gag gag       1348
Lys Ala Phe Trp Leu Ser Val His Gly Pro Arg Ala Ala Glu Glu Glu
350                 355                 360 ctg gtg gag gct gac gag gcg ggc agt gtg tat gca ggc atc ctc agc       1396
Leu Val Glu Ala Asp Glu Ala Gly Ser Val Tyr Ala Gly Ile Leu Ser
365                 370                 375                 380 tac ggg gtg ggc ttc ttc ctg ttc atc ctg gtg gtg gcg gct gtg acg       1444
Tyr Gly Val Gly Phe Phe Leu Phe Ile Leu Val Val Ala Ala Val Thr
            385                 390                 395 ctc tgc cgc ctg cgc agc ccc ccc aag aaa ggc ctg ggc tcc ccc acc       1492
Leu Cys Arg Leu Arg Ser Pro Pro Lys Lys Gly Leu Gly Ser Pro Thr
        400                 405                 410 gtg cac aag atc tcc cgc ttc ccg ctc aag cga cag gtg tcc ctg gag       1540
Val His Lys Ile Ser Arg Phe Pro Leu Lys Arg Gln Val Ser Leu Glu
    415                 420                 425 tcc aac gcg tcc atg agc tcc aac aca cca ctg gtg cgc atc gca agg       1588
Ser Asn Ala Ser Met Ser Ser Asn Thr Pro Leu Val Arg Ile Ala Arg
430                 435                 440 ctg tcc tca ggg gag ggc ccc acg ctg gcc aat gtc tcc gag ctc gag       1636
Leu Ser Ser Gly Glu Gly Pro Thr Leu Ala Asn Val Ser Glu Leu Glu
445                 450                 455                 460 ctg cct gcc gac ccc aaa tgg gag ctg tct cgg gcc cgg ctg acc ctg       1684
Leu Pro Ala Asp Pro Lys Trp Glu Leu Ser Arg Ala Arg Leu Thr Leu
            465                 470                 475 ggc aag ccc ctt ggg gag ggc tgc ttc ggc cag gtg gtc atg gcg gag       1732
Gly Lys Pro Leu Gly Glu Gly Cys Phe Gly Gln Val Val Met Ala Glu
        480                 485                 490 gcc atc ggc att gac aag gac cgg gcc gcc aag cct gtc acc gta gcc       1780
Ala Ile Gly Ile Asp Lys Asp Arg Ala Ala Lys Pro Val Thr Val Ala
    495                 500                 505 gtg aag atg ctg aaa gac gat gcc act gac aag gac ctg tcg gac ctg       1828
Val Lys Met Leu Lys Asp Asp Ala Thr Asp Lys Asp Leu Ser Asp Leu
510                 515                 520 gtg tct gag atg gag atg atg aag atg atc ggg aaa cac aaa aac atc       1876
Val Ser Glu Met Glu Met Met Lys Met Ile Gly Lys His Lys Asn Ile
525                 530                 535                 540 atc aac ctg ctg ggc gcc tgc acg cag ggc ggg ccc ctg tac gtg ctg       1924
```

|   |   |   |   |   |   |   |   |   |   |   |   |   |   |   |   |   |
|---|---|---|---|---|---|---|---|---|---|---|---|---|---|---|---|---|
| Ile | Asn | Leu | Leu | Gly<br>545 | Ala | Cys | Thr | Gln<br>550 | Gly | Gly | Pro | Leu<br>555 | Tyr | Val | Leu | |

```
gtg gag tac gcg gcc aag ggt aac ctg cgg gag ttt ctg cgg gcg cgg      1972
Val Glu Tyr Ala Ala Lys Gly Asn Leu Arg Glu Phe Leu Arg Ala Arg
            560                 565                 570 cgg ccc ccg ggc ctg gac tac tcc ttc gac acc tgc aag ccg ccc gag      2020
Arg Pro Pro Gly Leu Asp Tyr Ser Phe Asp Thr Cys Lys Pro Pro Glu
        575                 580                 585 gag cag ctc acc ttc aag gac ctg gtg tcc tgt gcc tac cag gtg gcc      2068
Glu Gln Leu Thr Phe Lys Asp Leu Val Ser Cys Ala Tyr Gln Val Ala
    590                 595                 600 cgg ggc atg gag tac ttg gcc tcc cag aag tgc atc cac agg gac ctg      2116
Arg Gly Met Glu Tyr Leu Ala Ser Gln Lys Cys Ile His Arg Asp Leu
605                 610                 615                 620 gct gcc cgc aat gtg ctg gtg acc gag gac aac gtg atg aag atc gca      2164
Ala Ala Arg Asn Val Leu Val Thr Glu Asp Asn Val Met Lys Ile Ala
                625                 630                 635 gac ttc ggg ctg gcc cgg gac gtg cac aac ctc gac tac tac aag aag      2212
Asp Phe Gly Leu Ala Arg Asp Val His Asn Leu Asp Tyr Tyr Lys Lys
            640                 645                 650 acg acc aac ggc cgg ctg ccc gtg aag tgg atg gcg cct gag gcc ttg      2260
Thr Thr Asn Gly Arg Leu Pro Val Lys Trp Met Ala Pro Glu Ala Leu
        655                 660                 665 ttt gac cga gtc tac act cac cag agt gac gtc tgg tcc ttt ggg gtc      2308
Phe Asp Arg Val Tyr Thr His Gln Ser Asp Val Trp Ser Phe Gly Val
    670                 675                 680 ctg ctc tgg gag atc ttc acg ctg ggg ggc tcc ccg tac ccc ggc atc      2356
Leu Leu Trp Glu Ile Phe Thr Leu Gly Gly Ser Pro Tyr Pro Gly Ile
685                 690                 695                 700 cct gtg gag gag ctc ttc aag ctg ctg aag gag ggc cac cgc atg gac      2404
Pro Val Glu Glu Leu Phe Lys Leu Leu Lys Glu Gly His Arg Met Asp
                705                 710                 715 aag ccc gcc aac tgc aca cac gac ctg tac atg atc atg cgg gag tgc      2452
Lys Pro Ala Asn Cys Thr His Asp Leu Tyr Met Ile Met Arg Glu Cys
            720                 725                 730 tgg cat gcc gcg ccc tcc cag agg ccc acc ttc aag cag ctg gtg gag      2500
Trp His Ala Ala Pro Ser Gln Arg Pro Thr Phe Lys Gln Leu Val Glu
        735                 740                 745 gac ctg gac cgt gtc ctt acc gtg acg tcc acc gac gag tac ctg gac      2548
Asp Leu Asp Arg Val Leu Thr Val Thr Ser Thr Asp Glu Tyr Leu Asp
    750                 755                 760 ctg tcg gcg cct ttc gag cag tac tcc ccg ggt ggc cag gac acc ccc      2596
Leu Ser Ala Pro Phe Glu Gln Tyr Ser Pro Gly Gly Gln Asp Thr Pro
765                 770                 775                 780 agc tcc agc tcc tca ggg gac gac tcc gtg tta aac agc caa cag ctc      2644
Ser Ser Ser Ser Ser Gly Asp Asp Ser Val Leu Asn Ser Gln Gln Leu
                785                 790                 795 atc aag gaa gtg gat gcc aaa act act cat gga att cta cag aaa cca      2692
Ile Lys Glu Val Asp Ala Lys Thr Thr His Gly Ile Leu Gln Lys Pro
            800                 805                 810 gtg gag gct gac acc gac ctc ctg ggg gat gca agc cca gcc ttt ggg      2740
Val Glu Ala Asp Thr Asp Leu Leu Gly Asp Ala Ser Pro Ala Phe Gly
        815                 820                 825 agt ggc agc tcc agc gag tct ggc cca ggt gcc ctg gct gac ctg gac      2788
Ser Gly Ser Ser Ser Glu Ser Gly Pro Gly Ala Leu Ala Asp Leu Asp
    830                 835                 840 tgc tca agc tct tcc cag agc cca gga agt tct gag aac caa atg gtg      2836
Cys Ser Ser Ser Ser Gln Ser Pro Gly Ser Ser Glu Asn Gln Met Val
845                 850                 855                 860
```

-continued

| | |
|---|---|
| tct cca gga aaa gtg tct ggc agc cct gag caa gcc gtg gag gaa aac<br>Ser Pro Gly Lys Val Ser Gly Ser Pro Glu Gln Ala Val Glu Glu Asn<br>                865                   870                 875 | 2884 |
| ctt agt tcc tat tcc tta gac aga aga gtg aca ccc gcc tct gag acc<br>Leu Ser Ser Tyr Ser Leu Asp Arg Arg Val Thr Pro Ala Ser Glu Thr<br>        880                   885                 890 | 2932 |
| cta gaa gac cct tgc agg aca gag tcc cag cac aaa gcg gag act ccg<br>Leu Glu Asp Pro Cys Arg Thr Glu Ser Gln His Lys Ala Glu Thr Pro<br>          895                   900               905 | 2980 |
| cac gga gcc gag gaa gaa tgc aaa gcg gag act ccg cac gga gcc gag<br>His Gly Ala Glu Glu Glu Cys Lys Ala Glu Thr Pro His Gly Ala Glu<br>    910                 915               920 | 3028 |
| gag gaa tgc cgg cac ggt ggg gtc tgt gct ccc gca gca gtg gcc act<br>Glu Glu Cys Arg His Gly Gly Val Cys Ala Pro Ala Ala Val Ala Thr<br>925               930               935              940 | 3076 |
| tcg cct cct ggt gca atc cct aag gaa gcc tgc gga gga gca ccc ctg<br>Ser Pro Pro Gly Ala Ile Pro Lys Glu Ala Cys Gly Gly Ala Pro Leu<br>                945                 950              955 | 3124 |
| cag ggt ctg cct ggc gaa gcc ctg ggc tgc cct gcg ggt gtg ggc acc<br>Gln Gly Leu Pro Gly Glu Ala Leu Gly Cys Pro Ala Gly Val Gly Thr<br>                  960                 965              970 | 3172 |
| ccc gtg cca gca gat ggc act cag acc ctt acc tgt gca cac acc tct<br>Pro Val Pro Ala Asp Gly Thr Gln Thr Leu Thr Cys Ala His Thr Ser<br>          975                   980               985 | 3220 |
| gct cct gag agc aca gcc cca acc aac cac ctg gtg   gct ggc agg gcc<br>Ala Pro Glu Ser Thr Ala Pro Thr Asn His Leu Val   Ala Gly Arg Ala<br>          990                   995               1000 | 3268 |
| atg   acc ctg agt cct cag gaa gaa gtg gct gca   ggc caa atg gcc<br>Met   Thr Leu Ser Pro Gln Glu Glu Val Ala Ala   Gly Gln Met Ala<br>1005                   1010                    1015 | 3313 |
| agc   tcc tcg agg agc gga   cct gta aaa cta gaa   ttt gat gta tct<br>Ser   Ser Ser Arg Ser Gly   Pro Val Lys Leu Glu   Phe Asp Val Ser<br>1020                  1025                  1030 | 3358 |
| gat   ggc gcc acc agc aaa   agg gca ccc cca cca   agg aga ctg gga<br>Asp   Gly Ala Thr Ser Lys   Arg Ala Pro Pro Pro   Arg Arg Leu Gly<br>1035                  1040                  1045 | 3403 |
| gag   agg tcc ggc ctc aag   cct ccc ttg agg aaa   gca gca gtg agg<br>Glu   Arg Ser Gly Leu Lys   Pro Pro Leu Arg Lys   Ala Ala Val Arg<br>1050                  1055                  1060 | 3448 |
| cag   caa aag gcc ccg cag   gag gtg gag gag gac   gac ggt agg agc<br>Gln   Gln Lys Ala Pro Gln   Glu Val Glu Glu Asp   Asp Gly Arg Ser<br>1065                  1070                  1075 | 3493 |
| gga   gca gga gag gac ccc   ccc atg cca gct tct   cgg ggc tct tac<br>Gly   Ala Gly Glu Asp Pro   Pro Met Pro Ala Ser   Arg Gly Ser Tyr<br>1080                  1085                  1090 | 3538 |
| cac   ctc gac tgg gac aaa   atg gat gac cca aac   ttc atc ccg ttc<br>His   Leu Asp Trp Asp Lys   Met Asp Asp Pro Asn   Phe Ile Pro Phe<br>1095                  1100                  1105 | 3583 |
| gga   ggt gac acc aag tct   ggt tgc agt gag gcc   cag ccc cca gaa<br>Gly   Gly Asp Thr Lys Ser   Gly Cys Ser Glu Ala   Gln Pro Pro Glu<br>1110                  1115                  1120 | 3628 |
| agc   cct gag acc agg ctg   ggc cag cca gcg gct   gaa cag ttg cat<br>Ser   Pro Glu Thr Arg Leu   Gly Gln Pro Ala Ala   Glu Gln Leu His<br>1125                  1130                  1135 | 3673 |
| gct   ggg cct gcc acg gag   gag cca ggt ccc tgt   ctg agc cag cag<br>Ala   Gly Pro Ala Thr Glu   Glu Pro Gly Pro Cys   Leu Ser Gln Gln<br>1140                  1145                  1150 | 3718 |
| ctg   cat tca gcc tca gcg   gag gac acg cct gtg   gtg cag ttg gca<br>Leu   His Ser Ala Ser Ala   Glu Asp Thr Pro Val   Val Gln Leu Ala<br>1155                  1160                  1165 | 3763 |

-continued

| | |
|---|---|
| gcc gag acc cca aca gca gag agc aag gag aga gcc ttg aac tct<br>Ala Glu Thr Pro Thr Ala Glu Ser Lys Glu Arg Ala Leu Asn Ser<br>1170                        1175                      1180 | 3808 |
| gcc agc acc tcg ctt ccc aca agc tgt cca ggc agt gag cca gtg<br>Ala Ser Thr Ser Leu Pro Thr Ser Cys Pro Gly Ser Glu Pro Val<br>1185                        1190                      1195 | 3853 |
| ccc acc cat cag cag ggg cag cct gcc ttg gag ctg aaa gag gag<br>Pro Thr His Gln Gln Gly Gln Pro Ala Leu Glu Leu Lys Glu Glu<br>1200                        1205                      1210 | 3898 |
| agc ttc aga gac ccc gct gag gtt cta ggc acg ggc gcg gag gtg<br>Ser Phe Arg Asp Pro Ala Glu Val Leu Gly Thr Gly Ala Glu Val<br>1215                        1220                      1225 | 3943 |
| gat tac ctg gag cag ttt gga act tcc tcg ttt aag gag tcg gcc<br>Asp Tyr Leu Glu Gln Phe Gly Thr Ser Ser Phe Lys Glu Ser Ala<br>1230                        1235                      1240 | 3988 |
| ttg agg aag cag tcc tta tac ctc aag ttc gac ccc ctc ctg agg<br>Leu Arg Lys Gln Ser Leu Tyr Leu Lys Phe Asp Pro Leu Leu Arg<br>1245                        1250                      1255 | 4033 |
| gac agt cct ggt aga cca gtg ccc gtg gcc acc gag acc agc agc<br>Asp Ser Pro Gly Arg Pro Val Pro Val Ala Thr Glu Thr Ser Ser<br>1260                        1265                      1270 | 4078 |
| atg cac ggt gca aat gag act ccc tca gga cgt ccg cgg gaa gcc<br>Met His Gly Ala Asn Glu Thr Pro Ser Gly Arg Pro Arg Glu Ala<br>1275                        1280                      1285 | 4123 |
| aag ctt gtg gag ttc gat ttc ttg gga gca ctg gac att cct gtg<br>Lys Leu Val Glu Phe Asp Phe Leu Gly Ala Leu Asp Ile Pro Val<br>1290                        1295                      1300 | 4168 |
| cca ggc cca ccc cca ggt gtt ccc gcg cct ggg ggc cca ccc ctg<br>Pro Gly Pro Pro Pro Gly Val Pro Ala Pro Gly Gly Pro Pro Leu<br>1305                        1310                      1315 | 4213 |
| tcc acc gga cct ata gtg gac ctg ctc cag tac agc cag aag gac<br>Ser Thr Gly Pro Ile Val Asp Leu Leu Gln Tyr Ser Gln Lys Asp<br>1320                        1325                      1330 | 4258 |
| ctg gat gca gtg gta aag gcg aca cag gag gag aac cgg gag ctg<br>Leu Asp Ala Val Val Lys Ala Thr Gln Glu Glu Asn Arg Glu Leu<br>1335                        1340                      1345 | 4303 |
| agg agc agg tgt gag gag ctc cac ggg aag aac ctg gaa ctg ggg<br>Arg Ser Arg Cys Glu Glu Leu His Gly Lys Asn Leu Glu Leu Gly<br>1350                        1355                      1360 | 4348 |
| aag atc atg gac agg ttc gaa gag gtt gtg tac cag gcc atg gag<br>Lys Ile Met Asp Arg Phe Glu Glu Val Val Tyr Gln Ala Met Glu<br>1365                        1370                      1375 | 4393 |
| gaa gtt cag aag cag aag gaa ctt tcc aaa gct gaa atc cag aaa<br>Glu Val Gln Lys Gln Lys Glu Leu Ser Lys Ala Glu Ile Gln Lys<br>1380                        1385                      1390 | 4438 |
| gtt cta aaa gaa aaa gac caa ctt acc aca gat ctg aac tcc atg<br>Val Leu Lys Glu Lys Asp Gln Leu Thr Thr Asp Leu Asn Ser Met<br>1395                        1400                      1405 | 4483 |
| gag aag tcc ttc tcc gac ctc ttc aag cgt ttt gag aaa cag aaa<br>Glu Lys Ser Phe Ser Asp Leu Phe Lys Arg Phe Glu Lys Gln Lys<br>1410                        1415                      1420 | 4528 |
| gag gtg atc gag ggc tac cgc aag aac gaa gag tca ctg aag aag<br>Glu Val Ile Glu Gly Tyr Arg Lys Asn Glu Glu Ser Leu Lys Lys<br>1425                        1430                      1435 | 4573 |
| tgc gtg gag gat tac ctg gca agg atc acc cag gag ggc cag agg<br>Cys Val Glu Asp Tyr Leu Ala Arg Ile Thr Gln Glu Gly Gln Arg<br>1440                        1445                      1450 | 4618 |
| tac caa gcc ctg aag gcc cac gcg gag gag aag ctg cag ctg gca<br>Tyr Gln Ala Leu Lys Ala His Ala Glu Glu Lys Leu Gln Leu Ala | 4663 |

-continued

```
                     1455                 1460                 1465
aac  gag  gag  atc  gcc  cag  gtc  cgg  agc  aag  gcc  cag  gcg  gaa  gcg      4708
Asn  Glu  Glu  Ile  Ala  Gln  Val  Arg  Ser  Lys  Ala  Gln  Ala  Glu  Ala
1470                 1475                 1480 ttg  gcc  ctc  cag  gcc  agc  ctg  agg  aag  gag  cag  atg  cgc  atc  cag      4753
Leu  Ala  Leu  Gln  Ala  Ser  Leu  Arg  Lys  Glu  Gln  Met  Arg  Ile  Gln
1485                 1490                 1495 tcg  ctg  gag  aag  aca  gtg  gag  cag  aag  act  aaa  gag  aac  gag  gag      4798
Ser  Leu  Glu  Lys  Thr  Val  Glu  Gln  Lys  Thr  Lys  Glu  Asn  Glu  Glu
1500                 1505                 1510 ctg  acc  agg  atc  tgc  gac  gac  ctc  atc  tcc  aag  atg  gag  aag  atc      4843
Leu  Thr  Arg  Ile  Cys  Asp  Asp  Leu  Ile  Ser  Lys  Met  Glu  Lys  Ile
1515                 1520                 1525 tga cctccacgga gccgctgtcc ccgccccct gctcccgtct gtctgtcctg                       4896
tctgattctc ttaggtgtca tgttctttt tctgtcttgt cttcaacttt tttaaaaact                4956
agattgcttt gaaaacatga ctcaataaaa gtttcctttc aatttaaa                            5004

<210> SEQ ID NO 2
<211> LENGTH: 1529
<212> TYPE: PRT
<213> ORGANISM: Homo sapiens

<400> SEQUENCE: 2

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255
```

```
Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Glu Leu Val Glu Ala
        355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670
```

-continued

```
Tyr Thr His Gln Ser Asp Val Trp Ser Phe Gly Val Leu Leu Trp Glu
            675                 680                 685

Ile Phe Thr Leu Gly Gly Ser Pro Tyr Pro Gly Ile Pro Val Glu Glu
        690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
                740                 745                 750

Val Leu Thr Val Thr Ser Thr Asp Glu Tyr Leu Asp Leu Ser Ala Pro
            755                 760                 765

Phe Glu Gln Tyr Ser Pro Gly Gly Gln Asp Thr Pro Ser Ser Ser Ser
        770                 775                 780

Ser Gly Asp Asp Ser Val Leu Asn Ser Gln Gln Leu Ile Lys Glu Val
785                 790                 795                 800

Asp Ala Lys Thr Thr His Gly Ile Leu Gln Lys Pro Val Glu Ala Asp
                805                 810                 815

Thr Asp Leu Leu Gly Asp Ala Ser Pro Ala Phe Gly Ser Gly Ser Ser
                820                 825                 830

Ser Glu Ser Gly Pro Gly Ala Leu Ala Asp Leu Asp Cys Ser Ser Ser
            835                 840                 845

Ser Gln Ser Pro Gly Ser Ser Glu Asn Gln Met Val Ser Pro Gly Lys
        850                 855                 860

Val Ser Gly Ser Pro Glu Gln Ala Val Glu Glu Asn Leu Ser Ser Tyr
865                 870                 875                 880

Ser Leu Asp Arg Arg Val Thr Pro Ala Ser Glu Thr Leu Glu Asp Pro
                885                 890                 895

Cys Arg Thr Glu Ser Gln His Lys Ala Glu Thr Pro His Gly Ala Glu
                900                 905                 910

Glu Glu Cys Lys Ala Glu Thr Pro His Gly Ala Glu Glu Cys Arg
            915                 920                 925

His Gly Gly Val Cys Ala Pro Ala Ala Val Ala Thr Ser Pro Pro Gly
930                 935                 940

Ala Ile Pro Lys Glu Ala Cys Gly Gly Ala Pro Leu Gln Gly Leu Pro
945                 950                 955                 960

Gly Glu Ala Leu Gly Cys Pro Ala Gly Val Gly Thr Pro Val Pro Ala
                965                 970                 975

Asp Gly Thr Gln Thr Leu Thr Cys Ala His Thr Ser Ala Pro Glu Ser
                980                 985                 990

Thr Ala Pro Thr Asn His Leu Val Ala Gly Arg Ala Met Thr Leu Ser
        995                 1000                1005

Pro Gln Glu Glu Val Ala Ala Gly Gln Met Ala Ser Ser Ser Arg
    1010                1015                1020

Ser Gly Pro Val Lys Leu Glu Phe Asp Val Ser Asp Gly Ala Thr
    1025                1030                1035

Ser Lys Arg Ala Pro Pro Arg Arg Leu Gly Glu Arg Ser Gly
    1040                1045                1050

Leu Lys Pro Pro Leu Arg Lys Ala Ala Val Arg Gln Gln Lys Ala
    1055                1060                1065

Pro Gln Glu Val Glu Glu Asp Asp Gly Arg Ser Gly Ala Gly Glu
    1070                1075                1080

Asp Pro Pro Met Pro Ala Ser Arg Gly Ser Tyr His Leu Asp Trp
```

-continued

```
            1085                1090                1095

Asp Lys Met Asp Asp Pro Asn Phe Ile Pro Phe Gly Gly Asp Thr
            1100                1105                1110

Lys Ser Gly Cys Ser Glu Ala Gln Pro Pro Glu Ser Pro Glu Thr
            1115                1120                1125

Arg Leu Gly Gln Pro Ala Ala Glu Gln Leu His Ala Gly Pro Ala
            1130                1135                1140

Thr Glu Glu Pro Gly Pro Cys Leu Ser Gln Gln Leu His Ser Ala
            1145                1150                1155

Ser Ala Glu Asp Thr Pro Val Val Gln Leu Ala Ala Glu Thr Pro
            1160                1165                1170

Thr Ala Glu Ser Lys Glu Arg Ala Leu Asn Ser Ala Ser Thr Ser
            1175                1180                1185

Leu Pro Thr Ser Cys Pro Gly Ser Glu Pro Val Pro Thr His Gln
            1190                1195                1200

Gln Gly Gln Pro Ala Leu Glu Leu Lys Glu Glu Ser Phe Arg Asp
            1205                1210                1215

Pro Ala Glu Val Leu Gly Thr Gly Ala Glu Val Asp Tyr Leu Glu
            1220                1225                1230

Gln Phe Gly Thr Ser Ser Phe Lys Glu Ser Ala Leu Arg Lys Gln
            1235                1240                1245

Ser Leu Tyr Leu Lys Phe Asp Pro Leu Leu Arg Asp Ser Pro Gly
            1250                1255                1260

Arg Pro Val Pro Val Ala Thr Glu Thr Ser Ser Met His Gly Ala
            1265                1270                1275

Asn Glu Thr Pro Ser Gly Arg Pro Arg Glu Ala Lys Leu Val Glu
            1280                1285                1290

Phe Asp Phe Leu Gly Ala Leu Asp Ile Pro Val Pro Gly Pro Pro
            1295                1300                1305

Pro Gly Val Pro Ala Pro Gly Gly Pro Pro Leu Ser Thr Gly Pro
            1310                1315                1320

Ile Val Asp Leu Leu Gln Tyr Ser Gln Lys Asp Leu Asp Ala Val
            1325                1330                1335

Val Lys Ala Thr Gln Glu Glu Asn Arg Glu Leu Arg Ser Arg Cys
            1340                1345                1350

Glu Glu Leu His Gly Lys Asn Leu Glu Leu Gly Lys Ile Met Asp
            1355                1360                1365

Arg Phe Glu Glu Val Val Tyr Gln Ala Met Glu Glu Val Gln Lys
            1370                1375                1380

Gln Lys Glu Leu Ser Lys Ala Glu Ile Gln Lys Val Leu Lys Glu
            1385                1390                1395

Lys Asp Gln Leu Thr Thr Asp Leu Asn Ser Met Glu Lys Ser Phe
            1400                1405                1410

Ser Asp Leu Phe Lys Arg Phe Glu Lys Gln Lys Glu Val Ile Glu
            1415                1420                1425

Gly Tyr Arg Lys Asn Glu Glu Ser Leu Lys Lys Cys Val Glu Asp
            1430                1435                1440

Tyr Leu Ala Arg Ile Thr Gln Glu Gly Gln Arg Tyr Gln Ala Leu
            1445                1450                1455

Lys Ala His Ala Glu Glu Lys Leu Gln Leu Ala Asn Glu Glu Ile
            1460                1465                1470

Ala Gln Val Arg Ser Lys Ala Gln Ala Glu Ala Leu Ala Leu Gln
            1475                1480                1485
```

```
Ala Ser  Leu Arg Lys Glu Gln  Met Arg Ile Gln Ser  Leu Glu Lys
    1490             1495                 1500

Thr Val  Glu Gln Lys Thr Lys  Glu Asn Glu Glu Leu  Thr Arg Ile
    1505             1510                 1515

Cys Asp  Asp Leu Ile Ser Lys  Met Glu Lys Ile
    1520             1525

<210> SEQ ID NO 3
<211> LENGTH: 3561
<212> TYPE: DNA
<213> ORGANISM: Homo sapiens
<220> FEATURE:
<221> NAME/KEY: CDS
<222> LOCATION: (257)..(3403)

<400> SEQUENCE: 3
```

| | | |
|---|---|---|
| gtcgcgggca gctggcgccg cgcggtcctg ctctgccggt cgcacggacg caccggcggg | 60 |
| ccgccggccg gagggacggg gcgggagctg ggcccgcgga cagcgagccg gagcgggagc | 120 |
| cgcgcgtagc gagccgggct ccggcgctcg ccagtctccc gagcggcgcc cgcctcccgc | 180 |
| cggtgcccgc gccgggccgt ggggggcagc atgcccgcgc gcgctgcctg aggacgccgc | 240 |
| ggccccccgcc cccgcc atg ggc gcc cct gcc tgc gcc ctc gcg ctc tgc gtg | 292 |
|                 Met Gly Ala Pro Ala Cys Ala Leu Ala Leu Cys Val | |
|                   1               5                  10 | |
| gcc gtg gcc atc gtg gcc ggg gcc tcc tcg gag tcc ttg ggg acg gag | 340 |
| Ala Val Ala Ile Val Ala Gly Ala Ser Ser Glu Ser Leu Gly Thr Glu | |
|         15                 20                 25 | |
| cag cgc gtc gtg ggg cga gcg gca gaa gtc ccg ggc cca gag ccc ggc | 388 |
| Gln Arg Val Val Gly Arg Ala Ala Glu Val Pro Gly Pro Glu Pro Gly | |
|     30                 35                 40 | |
| cag cag gag cag ttg gtc ttc ggc agc ggg gat gct gtg gag ctg agc | 436 |
| Gln Gln Glu Gln Leu Val Phe Gly Ser Gly Asp Ala Val Glu Leu Ser | |
| 45                 50                 55                 60 | |
| tgt ccc ccg ccc ggg ggt ggt ccc atg ggg ccc act gtc tgg gtc aag | 484 |
| Cys Pro Pro Pro Gly Gly Gly Pro Met Gly Pro Thr Val Trp Val Lys | |
|                 65                 70                 75 | |
| gat ggc aca ggg ctg gtg ccc tcg gag cgt gtc ctg gtg ggg ccc cag | 532 |
| Asp Gly Thr Gly Leu Val Pro Ser Glu Arg Val Leu Val Gly Pro Gln | |
|                 80                 85                 90 | |
| cgg ctg cag gtg ctg aat gcc tcc cac gag gac tcc ggg gcc tac agc | 580 |
| Arg Leu Gln Val Leu Asn Ala Ser His Glu Asp Ser Gly Ala Tyr Ser | |
|                 95                 100                105 | |
| tgc cgg cag cgg ctc acg cag cgc gta ctg tgc cac ttc agt gtg cgg | 628 |
| Cys Arg Gln Arg Leu Thr Gln Arg Val Leu Cys His Phe Ser Val Arg | |
|                 110                115                120 | |
| gtg aca gac gct cca tcc tcg gga gat gac gaa gac ggg gag gac gag | 676 |
| Val Thr Asp Ala Pro Ser Ser Gly Asp Asp Glu Asp Gly Glu Asp Glu | |
| 125                130                135                140 | |
| gct gag gac aca ggt gtg gac aca ggg gcc cct tac tgg aca cgg ccc | 724 |
| Ala Glu Asp Thr Gly Val Asp Thr Gly Ala Pro Tyr Trp Thr Arg Pro | |
|                 145                150                155 | |
| gag cgg atg gac aag aag ctg ctg gcc gtg ccg gcc gcc aac acc gtc | 772 |
| Glu Arg Met Asp Lys Lys Leu Leu Ala Val Pro Ala Ala Asn Thr Val | |
|                 160                165                170 | |
| cgc ttc cgc tgc cca gcc gct ggc aac ccc act ccc tcc atc tcc tgg | 820 |
| Arg Phe Arg Cys Pro Ala Ala Gly Asn Pro Thr Pro Ser Ile Ser Trp | |
|                 175                180                185 | |
| ctg aag aac ggc agg gag ttc cgc ggc gag cac cgc att gga ggc atc | 868 |
| Leu Lys Asn Gly Arg Glu Phe Arg Gly Glu His Arg Ile Gly Gly Ile | |

```
                190                 195                 200
aag ctg cgg cat cag cag tgg agc ctg gtc atg gaa agc gtg gtg ccc          916
Lys Leu Arg His Gln Gln Trp Ser Leu Val Met Glu Ser Val Val Pro
205                 210                 215                 220 tcg gac cgc ggc aac tac acc tgc gtc gtg gag aac aag ttt ggc agc          964
Ser Asp Arg Gly Asn Tyr Thr Cys Val Val Glu Asn Lys Phe Gly Ser
                225                 230                 235 atc cgg cag acg tac acg ctg gac gtg ctg gag cgc tcc ccg cac cgg         1012
Ile Arg Gln Thr Tyr Thr Leu Asp Val Leu Glu Arg Ser Pro His Arg
        240                 245                 250 ccc atc ctg cag gcg ggg ctg ccg gcc aac cag acg gcg gtg ctg ggc         1060
Pro Ile Leu Gln Ala Gly Leu Pro Ala Asn Gln Thr Ala Val Leu Gly
        255                 260                 265 agc gac gtg gag ttc cac tgc aag gtg tac agt gac gca cag ccc cac         1108
Ser Asp Val Glu Phe His Cys Lys Val Tyr Ser Asp Ala Gln Pro His
270                 275                 280 atc cag tgg ctc aag cac gtg gag gtg aat ggc agc aag gtg ggc ccg         1156
Ile Gln Trp Leu Lys His Val Glu Val Asn Gly Ser Lys Val Gly Pro
285                 290                 295                 300 gac ggc aca ccc tac gtt acc gtg ctc aag tcc tgg atc agt gag agt         1204
Asp Gly Thr Pro Tyr Val Thr Val Leu Lys Ser Trp Ile Ser Glu Ser
                305                 310                 315 gtg gag gcc gac gtg cgc ctc cgc ctg gcc aat gtg tcg gag cgg gac         1252
Val Glu Ala Asp Val Arg Leu Arg Leu Ala Asn Val Ser Glu Arg Asp
        320                 325                 330 ggg ggc gag tac ctc tgt cga gcc acc aat ttc ata ggc gtg gcc gag         1300
Gly Gly Glu Tyr Leu Cys Arg Ala Thr Asn Phe Ile Gly Val Ala Glu
        335                 340                 345 aag gcc ttt tgg ctg agc gtt cac ggg ccc cga gca gcc gag gag gag         1348
Lys Ala Phe Trp Leu Ser Val His Gly Pro Arg Ala Ala Glu Glu Glu
350                 355                 360 ctg gtg gag gct gac gag gcg ggc agt gtg tat gca ggc atc ctc agc         1396
Leu Val Glu Ala Asp Glu Ala Gly Ser Val Tyr Ala Gly Ile Leu Ser
365                 370                 375                 380 tac ggg gtg ggc ttc ttc ctg ttc atc ctg gtg gtg gcg gct gtg acg         1444
Tyr Gly Val Gly Phe Phe Leu Phe Ile Leu Val Val Ala Ala Val Thr
                385                 390                 395 ctc tgc cgc ctg cgc agc ccc ccc aag aaa ggc ctg ggc tcc ccc acc         1492
Leu Cys Arg Leu Arg Ser Pro Pro Lys Lys Gly Leu Gly Ser Pro Thr
        400                 405                 410 gtg cac aag atc tcc cgc ttc ccg ctc aag cga cag gtg tcc ctg gag         1540
Val His Lys Ile Ser Arg Phe Pro Leu Lys Arg Gln Val Ser Leu Glu
        415                 420                 425 tcc aac gcg tcc atg agc tcc aac aca cca ctg gtg cgc atc gca agg         1588
Ser Asn Ala Ser Met Ser Ser Asn Thr Pro Leu Val Arg Ile Ala Arg
430                 435                 440 ctg tcc tca ggg gag ggc ccc acg ctg gcc aat gtc tcc gag ctc gag         1636
Leu Ser Ser Gly Glu Gly Pro Thr Leu Ala Asn Val Ser Glu Leu Glu
445                 450                 455                 460 ctg cct gcc gac ccc aaa tgg gag ctg tct cgg gcc cgg ctg acc ctg         1684
Leu Pro Ala Asp Pro Lys Trp Glu Leu Ser Arg Ala Arg Leu Thr Leu
                465                 470                 475 ggc aag ccc ctt ggg gag ggc tgc ttc ggc cag gtg gtc atg gcg gag         1732
Gly Lys Pro Leu Gly Glu Gly Cys Phe Gly Gln Val Val Met Ala Glu
        480                 485                 490 gcc atc ggc att gac aag gac cgg gcc gcc aag cct gtc acc gta gcc         1780
Ala Ile Gly Ile Asp Lys Asp Arg Ala Ala Lys Pro Val Thr Val Ala
        495                 500                 505 gtg aag atg ctg aaa gac gat gcc act gac aag gac ctg tcg gac ctg         1828
```

| | | | | | | | | | | | | | | | |
|---|---|---|---|---|---|---|---|---|---|---|---|---|---|---|---|
| | Val | Lys | Met | Leu | Lys | Asp | Asp | Ala | Thr | Asp | Lys | Asp | Leu | Ser | Asp | Leu |
| | 510 | | | | 515 | | | | | 520 | | | | | |

```
gtg tct gag atg gag atg atg aag atg atc ggg aaa cac aaa aac atc      1876
Val Ser Glu Met Glu Met Met Lys Met Ile Gly Lys His Lys Asn Ile
525             530             535             540 atc aac ctg ctg ggc gcc tgc acg cag ggc ggg ccc ctg tac gtg ctg      1924
Ile Asn Leu Leu Gly Ala Cys Thr Gln Gly Gly Pro Leu Tyr Val Leu
            545             550             555 gtg gag tac gcg gcc aag ggt aac ctg cgg gag ttt ctg cgg gcg cgg      1972
Val Glu Tyr Ala Ala Lys Gly Asn Leu Arg Glu Phe Leu Arg Ala Arg
        560             565             570 cgg ccc ccg ggc ctg gac tac tcc ttc gac acc tgc aag ccg ccc gag      2020
Arg Pro Pro Gly Leu Asp Tyr Ser Phe Asp Thr Cys Lys Pro Pro Glu
    575             580             585 gag cag ctc acc ttc aag gac ctg gtg tcc tgt gcc tac cag gtg gcc      2068
Glu Gln Leu Thr Phe Lys Asp Leu Val Ser Cys Ala Tyr Gln Val Ala
590             595             600 cgg ggc atg gag tac ttg gcc tcc cag aag tgc atc cac agg gac ctg      2116
Arg Gly Met Glu Tyr Leu Ala Ser Gln Lys Cys Ile His Arg Asp Leu
605             610             615             620 gct gcc cgc aat gtg ctg gtg acc gag gac aac gtg atg aag atc gca      2164
Ala Ala Arg Asn Val Leu Val Thr Glu Asp Asn Val Met Lys Ile Ala
            625             630             635 gac ttc ggg ctg gcc cgg gac gtg cac aac ctc gac tac tac aag aag      2212
Asp Phe Gly Leu Ala Arg Asp Val His Asn Leu Asp Tyr Tyr Lys Lys
        640             645             650 acg acc aac ggc cgg ctg ccc gtg aag tgg atg gcg cct gag gcc ttg      2260
Thr Thr Asn Gly Arg Leu Pro Val Lys Trp Met Ala Pro Glu Ala Leu
    655             660             665 ttt gac cga gtc tac act cac cag agt gac gtc tgg tcc ttt ggg gtc      2308
Phe Asp Arg Val Tyr Thr His Gln Ser Asp Val Trp Ser Phe Gly Val
670             675             680 ctg ctc tgg gag atc ttc acg ctg ggg ggc tcc ccg tac ccc ggc atc      2356
Leu Leu Trp Glu Ile Phe Thr Leu Gly Gly Ser Pro Tyr Pro Gly Ile
685             690             695             700 cct gtg gag gag ctc ttc aag ctg ctg aag gag ggc cac cgc atg gac      2404
Pro Val Glu Glu Leu Phe Lys Leu Leu Lys Glu Gly His Arg Met Asp
            705             710             715 aag ccc gcc aac tgc aca cac gac ctg tac atg atc atg cgg gag tgc      2452
Lys Pro Ala Asn Cys Thr His Asp Leu Tyr Met Ile Met Arg Glu Cys
        720             725             730 tgg cat gcc gcg ccc tcc cag agg ccc acc ttc aag cag ctg gtg gag      2500
Trp His Ala Ala Pro Ser Gln Arg Pro Thr Phe Lys Gln Leu Val Glu
    735             740             745 gac ctg gac cgt gtc ctt acc gtg acg tcc acc gac gag tac ctg gac      2548
Asp Leu Asp Arg Val Leu Thr Val Thr Ser Thr Asp Glu Tyr Leu Asp
750             755             760 ctg tcg gcg cct ttc gag cag tac tcc ccg ggt ggc cag gac acc ccc      2596
Leu Ser Ala Pro Phe Glu Gln Tyr Ser Pro Gly Gly Gln Asp Thr Pro
765             770             775             780 agc tcc agc tcc tca ggg gac gac tcc gtg tta aac agc atg cac ggt      2644
Ser Ser Ser Ser Ser Gly Asp Asp Ser Val Leu Asn Ser Met His Gly
            785             790             795 gca aat gag act ccc tca gga cgt ccg cgg gaa gcc aag ctt gtg gag      2692
Ala Asn Glu Thr Pro Ser Gly Arg Pro Arg Glu Ala Lys Leu Val Glu
        800             805             810 ttc gat ttc ttg gga gca ctg gac att cct gtg cca ggc cca ccc cca      2740
Phe Asp Phe Leu Gly Ala Leu Asp Ile Pro Val Pro Gly Pro Pro Pro
815             820             825
```

```
ggt gtt ccc gcg cct ggg ggc cca ccc ctg tcc acc gga cct ata gtg   2788
Gly Val Pro Ala Pro Gly Gly Pro Pro Leu Ser Thr Gly Pro Ile Val
        830                 835                 840 gac ctg ctc cag tac agc cag aag gac ctg gat gca gtg gta aag gcg   2836
Asp Leu Leu Gln Tyr Ser Gln Lys Asp Leu Asp Ala Val Val Lys Ala
845                 850                 855                 860 aca cag gag gag aac cgg gag ctg agg agc agg tgt gag gag ctc cac   2884
Thr Gln Glu Glu Asn Arg Glu Leu Arg Ser Arg Cys Glu Glu Leu His
                865                 870                 875 ggg aag aac ctg gaa ctg ggg aag atc atg gac agg ttc gaa gag gtt   2932
Gly Lys Asn Leu Glu Leu Gly Lys Ile Met Asp Arg Phe Glu Glu Val
            880                 885                 890 gtg tac cag gcc atg gag gaa gtt cag aag cag aag gaa ctt tcc aaa   2980
Val Tyr Gln Ala Met Glu Glu Val Gln Lys Gln Lys Glu Leu Ser Lys
        895                 900                 905 gct gaa atc cag aaa gtt cta aaa gaa aaa gac caa ctt acc aca gat   3028
Ala Glu Ile Gln Lys Val Leu Lys Glu Lys Asp Gln Leu Thr Thr Asp
910                 915                 920 ctg aac tcc atg gag aag tcc ttc tcc gac ctc ttc aag cgt ttt gag   3076
Leu Asn Ser Met Glu Lys Ser Phe Ser Asp Leu Phe Lys Arg Phe Glu
925                 930                 935                 940 aaa cag aaa gag gtg atc gag ggc tac cgc aag aac gaa gag tca ctg   3124
Lys Gln Lys Glu Val Ile Glu Gly Tyr Arg Lys Asn Glu Glu Ser Leu
                945                 950                 955 aag aag tgc gtg gag gat tac ctg gca agg atc acc cag gag ggc cag   3172
Lys Lys Cys Val Glu Asp Tyr Leu Ala Arg Ile Thr Gln Glu Gly Gln
            960                 965                 970 agg tac caa gcc ctg aag gcc cac gcg gag gag aag ctg cag ctg gca   3220
Arg Tyr Gln Ala Leu Lys Ala His Ala Glu Glu Lys Leu Gln Leu Ala
        975                 980                 985 aac gag gag atc gcc cag gtc cgg agc aag gcc cag  gcg gaa gcg ttg   3268
Asn Glu Glu Ile Ala Gln Val Arg Ser Lys Ala Gln  Ala Glu Ala Leu
                990                 995                 1000 gcc  ctc cag gcc agc ctg  agg aag gag cag atg  cgc atc cag tcg     3313
Ala  Leu Gln Ala Ser Leu  Arg Lys Glu Gln Met  Arg Ile Gln Ser
1005                 1010                 1015 ctg  gag aag aca gtg gag  cag aag act aaa gag  aac gag gag ctg     3358
Leu  Glu Lys Thr Val Glu  Gln Lys Thr Lys Glu  Asn Glu Glu Leu
1020                 1025                 1030 acc  agg atc tgc gac gac  ctc atc tcc aag atg  gag aag atc tga     3403
Thr  Arg Ile Cys Asp Asp  Leu Ile Ser Lys Met  Glu Lys Ile
1035                 1040                 1045 cctccacgga gccgctgtcc ccgcccccct gctcccgtct gtctgtcctg tctgattctc   3463
ttaggtgtca tgttcttttt tctgtcttgt cttcaacttt tttaaaaact agattgcttt   3523
gaaaacatga ctcaataaaa gtttcctttc aatttaaa                          3561

<210> SEQ ID NO 4
<211> LENGTH: 1048
<212> TYPE: PRT
<213> ORGANISM: Homo sapiens

<400> SEQUENCE: 4

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45
```

```
Leu Val Phe Gly Ser Gly Asp Ala Val Glu Leu Ser Cys Pro Pro Pro
         50                  55                  60

Gly Gly Gly Pro Met Gly Pro Thr Val Trp Val Lys Asp Gly Thr Gly
 65              70                  75                  80

Leu Val Pro Ser Glu Arg Val Leu Val Gly Pro Gln Arg Leu Gln Val
                 85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
        130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
        290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Leu Val Glu Ala
        355                 360                 365

Asp Glu Ala Gly Ser Val Tyr Ala Gly Ile Leu Ser Tyr Gly Val Gly
370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
                420                 425                 430

Met Ser Ser Asn Thr Pro Leu Val Arg Ile Ala Arg Leu Ser Ser Gly
            435                 440                 445

Glu Gly Pro Thr Leu Ala Asn Val Ser Glu Leu Glu Leu Pro Ala Asp
450                 455                 460

Pro Lys Trp Glu Leu Ser Arg Ala Arg Leu Thr Leu Gly Lys Pro Leu
```

-continued

```
465                 470                 475                 480
Gly Glu Gly Cys Phe Gly Gln Val Val Met Ala Glu Ala Ile Gly Ile
                    485                 490                 495
Asp Lys Asp Arg Ala Ala Lys Pro Val Thr Val Ala Val Lys Met Leu
                500                 505                 510
Lys Asp Asp Ala Thr Asp Lys Asp Leu Ser Asp Leu Val Ser Glu Met
                515                 520                 525
Glu Met Met Lys Met Ile Gly Lys His Lys Asn Ile Ile Asn Leu Leu
            530                 535                 540
Gly Ala Cys Thr Gln Gly Gly Pro Leu Tyr Val Leu Val Glu Tyr Ala
545                 550                 555                 560
Ala Lys Gly Asn Leu Arg Glu Phe Leu Arg Ala Arg Arg Pro Pro Gly
                565                 570                 575
Leu Asp Tyr Ser Phe Asp Thr Cys Lys Pro Pro Glu Glu Gln Leu Thr
                580                 585                 590
Phe Lys Asp Leu Val Ser Cys Ala Tyr Gln Val Ala Arg Gly Met Glu
                595                 600                 605
Tyr Leu Ala Ser Gln Lys Cys Ile His Arg Asp Leu Ala Ala Arg Asn
            610                 615                 620
Val Leu Val Thr Glu Asp Asn Val Met Lys Ile Ala Asp Phe Gly Leu
625                 630                 635                 640
Ala Arg Asp Val His Asn Leu Asp Tyr Tyr Lys Lys Thr Thr Asn Gly
                645                 650                 655
Arg Leu Pro Val Lys Trp Met Ala Pro Glu Ala Leu Phe Asp Arg Val
                660                 665                 670
Tyr Thr His Gln Ser Asp Val Trp Ser Phe Gly Val Leu Leu Trp Glu
            675                 680                 685
Ile Phe Thr Leu Gly Gly Ser Pro Tyr Pro Gly Ile Pro Val Glu Glu
            690                 695                 700
Leu Phe Lys Leu Leu Lys Glu Gly His Arg Met Asp Lys Pro Ala Asn
705                 710                 715                 720
Cys Thr His Asp Leu Tyr Met Ile Met Arg Glu Cys Trp His Ala Ala
                725                 730                 735
Pro Ser Gln Arg Pro Thr Phe Lys Gln Leu Val Glu Asp Leu Asp Arg
                740                 745                 750
Val Leu Thr Val Thr Ser Thr Asp Glu Tyr Leu Asp Leu Ser Ala Pro
                755                 760                 765
Phe Glu Gln Tyr Ser Pro Gly Gly Gln Asp Thr Pro Ser Ser Ser Ser
            770                 775                 780
Ser Gly Asp Asp Ser Val Leu Asn Ser Met His Gly Ala Asn Glu Thr
785                 790                 795                 800
Pro Ser Gly Arg Pro Arg Glu Ala Lys Leu Val Glu Phe Asp Phe Leu
                805                 810                 815
Gly Ala Leu Asp Ile Pro Val Pro Gly Pro Pro Gly Val Pro Ala
                820                 825                 830
Pro Gly Gly Pro Pro Leu Ser Thr Gly Pro Ile Val Asp Leu Leu Gln
            835                 840                 845
Tyr Ser Gln Lys Asp Leu Asp Ala Val Val Lys Ala Thr Gln Glu Glu
            850                 855                 860
Asn Arg Glu Leu Arg Ser Arg Cys Glu Glu Leu His Gly Lys Asn Leu
865                 870                 875                 880
Glu Leu Gly Lys Ile Met Asp Arg Phe Glu Glu Val Val Tyr Gln Ala
                885                 890                 895
```

```
Met Glu Glu Val Gln Lys Gln Lys Glu Leu Ser Lys Ala Glu Ile Gln
            900                 905                 910
Lys Val Leu Lys Glu Lys Asp Gln Leu Thr Thr Asp Leu Asn Ser Met
        915                 920                 925
Glu Lys Ser Phe Ser Asp Leu Phe Lys Arg Phe Glu Lys Gln Lys Glu
    930                 935                 940
Val Ile Glu Gly Tyr Arg Lys Asn Glu Glu Ser Leu Lys Lys Cys Val
945                 950                 955                 960
Glu Asp Tyr Leu Ala Arg Ile Thr Gln Glu Gly Gln Arg Tyr Gln Ala
                965                 970                 975
Leu Lys Ala His Ala Glu Glu Lys Leu Gln Leu Ala Asn Glu Glu Ile
            980                 985                 990
Ala Gln Val Arg Ser Lys Ala Gln  Ala Glu Ala Leu Ala  Leu Gln Ala
        995                 1000                1005
Ser Leu  Arg Lys Glu Gln Met  Arg Ile Gln Ser Leu  Glu Lys Thr
       1010                1015                1020
Val Glu  Gln Lys Thr Lys Glu  Asn Glu Glu Leu Thr  Arg Ile Cys
       1025                1030                1035
Asp Asp  Leu Ile Ser Lys Met  Glu Lys Ile
       1040                1045
```

<210> SEQ ID NO 5
<211> LENGTH: 3270
<212> TYPE: DNA
<213> ORGANISM: Homo sapiens
<220> FEATURE:
<221> NAME/KEY: CDS
<222> LOCATION: (257)..(3112)

<400> SEQUENCE: 5

```
gtcgcgggca gctggcgccg cgcggtcctg ctctgccggt cgcacggacg caccggcggg      60
ccgccggccg gagggacggg gcgggagctg ggcccgcgga cagcgagccg gagcgggagc     120
cgcgcgtagc gagccgggct ccggcgctcg ccagtctccc gagcggcgcc cgcctcccgc     180
cggtgcccgc gccgggccgt gggggcagc atgcccgcgc gcgctgcctg aggacgccgc      240 ggccccgcc ccgc atg ggc gcc cct gcc tgc gcc ctc gcg ctc tgc gtg       292
             Met Gly Ala Pro Ala Cys Ala Leu Ala Leu Cys Val
               1               5                  10 gcc gtg gcc atc gtg gcc ggc gcc tcc tcg gag tcc ttg ggg acg gag     340
Ala Val Ala Ile Val Ala Gly Ala Ser Ser Glu Ser Leu Gly Thr Glu
         15                  20                  25 cag cgc gtc gtg ggg cga gcg gca gaa gtc ccg ggc cca gag ccc ggc     388
Gln Arg Val Val Gly Arg Ala Ala Glu Val Pro Gly Pro Glu Pro Gly
     30                  35                  40 cag cag gag cag ttg gtc ttc ggc agc ggg gat gct gtg gag ctg agc     436
Gln Gln Glu Gln Leu Val Phe Gly Ser Gly Asp Ala Val Glu Leu Ser
45                  50                  55                  60 tgt ccc ccg ccc ggg ggt ggt ccc atg ggg ccc act gtc tgg gtc aag     484
Cys Pro Pro Pro Gly Gly Gly Pro Met Gly Pro Thr Val Trp Val Lys
                 65                  70                  75 gat ggc aca ggg ctg gtg ccc tcg gag cgt gtc ctg gtg ggg ccc cag     532
Asp Gly Thr Gly Leu Val Pro Ser Glu Arg Val Leu Val Gly Pro Gln
             80                  85                  90 cgg ctg cag gtg ctg aat gcc tcc cac gag gac tcc ggg gcc tac agc     580
Arg Leu Gln Val Leu Asn Ala Ser His Glu Asp Ser Gly Ala Tyr Ser
         95                 100                 105 tgc cgg cag cgg ctc acg cag cgc gta ctg tgc cac ttc agt gtg cgg     628
```

```
                Cys Arg Gln Arg Leu Thr Gln Arg Val Leu Cys His Phe Ser Val Arg
                    110                 115                 120 gtg aca gac gct cca tcc tcg gga gat gac gaa gac ggg gag gac gag           676
Val Thr Asp Ala Pro Ser Ser Gly Asp Asp Glu Asp Gly Glu Asp Glu
125                 130                 135                 140 gct gag gac aca ggt gtg gac aca ggg gcc cct tac tgg aca cgg ccc           724
Ala Glu Asp Thr Gly Val Asp Thr Gly Ala Pro Tyr Trp Thr Arg Pro
                        145                 150                 155 gag cgg atg gac aag aag ctg ctg gcc gtg ccg gcc gcc aac acc gtc           772
Glu Arg Met Asp Lys Lys Leu Leu Ala Val Pro Ala Ala Asn Thr Val
            160                 165                 170 cgc ttc cgc tgc cca gcc gct ggc aac ccc act ccc tcc atc tcc tgg           820
Arg Phe Arg Cys Pro Ala Ala Gly Asn Pro Thr Pro Ser Ile Ser Trp
                175                 180                 185 ctg aag aac ggc agg gag ttc cgc ggc gag cac cgc att gga ggc atc           868
Leu Lys Asn Gly Arg Glu Phe Arg Gly Glu His Arg Ile Gly Gly Ile
        190                 195                 200 aag ctg cgg cat cag cag tgg agc ctg gtc atg gaa agc gtg gtg ccc           916
Lys Leu Arg His Gln Gln Trp Ser Leu Val Met Glu Ser Val Val Pro
205                 210                 215                 220 tcg gac cgc ggc aac tac acc tgc gtc gtg gag aac aag ttt ggc agc           964
Ser Asp Arg Gly Asn Tyr Thr Cys Val Val Glu Asn Lys Phe Gly Ser
                        225                 230                 235 atc cgg cag acg tac acg ctg gac gtg ctg gag cgc tcc ccg cac cgg          1012
Ile Arg Gln Thr Tyr Thr Leu Asp Val Leu Glu Arg Ser Pro His Arg
            240                 245                 250 ccc atc ctg cag gcg ggg ctg ccg gcc aac cag acg gcg gtg ctg ggc          1060
Pro Ile Leu Gln Ala Gly Leu Pro Ala Asn Gln Thr Ala Val Leu Gly
                255                 260                 265 agc gac gtg gag ttc cac tgc aag gtg tac agt gac gca cag ccc cac          1108
Ser Asp Val Glu Phe His Cys Lys Val Tyr Ser Asp Ala Gln Pro His
        270                 275                 280 atc cag tgg ctc aag cac gtg gag gtg aat ggc agc aag gtg ggc ccg          1156
Ile Gln Trp Leu Lys His Val Glu Val Asn Gly Ser Lys Val Gly Pro
285                 290                 295                 300 gac ggc aca ccc tac gtt acc gtg ctc aag tcc tgg atc agt gag agt          1204
Asp Gly Thr Pro Tyr Val Thr Val Leu Lys Ser Trp Ile Ser Glu Ser
                        305                 310                 315 gtg gag gcc gac gtg cgc ctc cgc ctg gcc aat gtg tcg gag cgg gac          1252
Val Glu Ala Asp Val Arg Leu Arg Leu Ala Asn Val Ser Glu Arg Asp
            320                 325                 330 ggg ggc gag tac ctc tgt cga gcc acc aat ttc ata ggc gtg gcc gag          1300
Gly Gly Glu Tyr Leu Cys Arg Ala Thr Asn Phe Ile Gly Val Ala Glu
                335                 340                 345 aag gcc ttt tgg ctg agc gtt cac ggg ccc cga gca gcc gag gag gag          1348
Lys Ala Phe Trp Leu Ser Val His Gly Pro Arg Ala Ala Glu Glu Glu
        350                 355                 360 ctg gtg gag gct gac gag gcg ggc agt gtg tat gca ggc atc ctc agc          1396
Leu Val Glu Ala Asp Glu Ala Gly Ser Val Tyr Ala Gly Ile Leu Ser
365                 370                 375                 380 tac ggg gtg ggc ttc ttc ctg ttc atc ctg gtg gtg gcg gct gtg acg          1444
Tyr Gly Val Gly Phe Phe Leu Phe Ile Leu Val Val Ala Ala Val Thr
                        385                 390                 395 ctc tgc cgc ctg cgc agc ccc ccc aag aaa ggc ctg ggc tcc ccc acc          1492
Leu Cys Arg Leu Arg Ser Pro Pro Lys Lys Gly Leu Gly Ser Pro Thr
            400                 405                 410 gtg cac aag atc tcc cgc ttc ccg ctc aag cga cag gtg tcc ctg gag          1540
Val His Lys Ile Ser Arg Phe Pro Leu Lys Arg Gln Val Ser Leu Glu
                415                 420                 425
```

```
tcc aac gcg tcc atg agc tcc aac aca cca ctg gtg cgc atc gca agg    1588
Ser Asn Ala Ser Met Ser Ser Asn Thr Pro Leu Val Arg Ile Ala Arg
        430                 435                 440 ctg tcc tca ggg gag ggc ccc acg ctg gcc aat gtc tcc gag ctc gag    1636
Leu Ser Ser Gly Glu Gly Pro Thr Leu Ala Asn Val Ser Glu Leu Glu
445                 450                 455                 460 ctg cct gcc gac ccc aaa tgg gag ctg tct cgg gcc cgg ctg acc ctg    1684
Leu Pro Ala Asp Pro Lys Trp Glu Leu Ser Arg Ala Arg Leu Thr Leu
                465                 470                 475 ggc aag ccc ctt ggg gag ggc tgc ttc ggc cag gtg gtc atg gcg gag    1732
Gly Lys Pro Leu Gly Glu Gly Cys Phe Gly Gln Val Val Met Ala Glu
            480                 485                 490 gcc atc ggc att gac aag gac cgg gcc gcc aag cct gtc acc gta gcc    1780
Ala Ile Gly Ile Asp Lys Asp Arg Ala Ala Lys Pro Val Thr Val Ala
        495                 500                 505 gtg aag atg ctg aaa gac gat gcc act gac aag gac ctg tcg gac ctg    1828
Val Lys Met Leu Lys Asp Asp Ala Thr Asp Lys Asp Leu Ser Asp Leu
    510                 515                 520 gtg tct gag atg gag atg atg aag atg atc ggg aaa cac aaa aac atc    1876
Val Ser Glu Met Glu Met Met Lys Met Ile Gly Lys His Lys Asn Ile
525                 530                 535                 540 atc aac ctg ctg ggc gcc tgc acg cag ggc ggg ccc ctg tac gtg ctg    1924
Ile Asn Leu Leu Gly Ala Cys Thr Gln Gly Gly Pro Leu Tyr Val Leu
                545                 550                 555 gtg gag tac gcg gcc aag ggt aac ctg cgg gag ttt ctg cgg gcg cgg    1972
Val Glu Tyr Ala Ala Lys Gly Asn Leu Arg Glu Phe Leu Arg Ala Arg
            560                 565                 570 cgg ccc ccg ggc ctg gac tac tcc ttc gac acc tgc aag ccg ccc gag    2020
Arg Pro Pro Gly Leu Asp Tyr Ser Phe Asp Thr Cys Lys Pro Pro Glu
        575                 580                 585 gag cag ctc acc ttc aag gac ctg gtg tcc tgt gcc tac cag gtg gcc    2068
Glu Gln Leu Thr Phe Lys Asp Leu Val Ser Cys Ala Tyr Gln Val Ala
    590                 595                 600 cgg ggc atg gag tac ttg gcc tcc cag aag tgc atc cac agg gac ctg    2116
Arg Gly Met Glu Tyr Leu Ala Ser Gln Lys Cys Ile His Arg Asp Leu
605                 610                 615                 620 gct gcc cgc aat gtg ctg gtg acc gag gac aac gtg atg aag atc gca    2164
Ala Ala Arg Asn Val Leu Val Thr Glu Asp Asn Val Met Lys Ile Ala
                625                 630                 635 gac ttc ggg ctg gcc cgg gac gtg cac aac ctc gac tac tac aag aag    2212
Asp Phe Gly Leu Ala Arg Asp Val His Asn Leu Asp Tyr Tyr Lys Lys
            640                 645                 650 acg acc aac ggc cgg ctg ccc gtg aag tgg atg gcg cct gag gcc ttg    2260
Thr Thr Asn Gly Arg Leu Pro Val Lys Trp Met Ala Pro Glu Ala Leu
        655                 660                 665 ttt gac cga gtc tac act cac cag agt gac gtc tgg tcc ttt ggg gtc    2308
Phe Asp Arg Val Tyr Thr His Gln Ser Asp Val Trp Ser Phe Gly Val
    670                 675                 680 ctg ctc tgg gag atc ttc acg ctg ggg ggc tcc ccg tac ccc ggc atc    2356
Leu Leu Trp Glu Ile Phe Thr Leu Gly Gly Ser Pro Tyr Pro Gly Ile
685                 690                 695                 700 cct gtg gag gag ctc ttc aag ctg ctg aag gag ggc cac cgc atg gac    2404
Pro Val Glu Glu Leu Phe Lys Leu Leu Lys Glu Gly His Arg Met Asp
                705                 710                 715 aag ccc gcc aac tgc aca cac gac ctg tac atg atc atg cgg gag tgc    2452
Lys Pro Ala Asn Cys Thr His Asp Leu Tyr Met Ile Met Arg Glu Cys
            720                 725                 730 tgg cat gcc gcg ccc tcc cag agg ccc acc ttc aag cag ctg gtg gag    2500
Trp His Ala Ala Pro Ser Gln Arg Pro Thr Phe Lys Gln Leu Val Glu
        735                 740                 745
```

```
gac ctg gac cgt gtc ctt acc gtg acg tcc acc gac gta aag gcg aca    2548
Asp Leu Asp Arg Val Leu Thr Val Thr Ser Thr Asp Val Lys Ala Thr
750                 755                 760 cag gag gag aac cgg gag ctg agg agc agg tgt gag gag ctc cac ggg    2596
Gln Glu Glu Asn Arg Glu Leu Arg Ser Arg Cys Glu Glu Leu His Gly
765                 770                 775                 780 aag aac ctg gaa ctg ggg aag atc atg gac agg ttc gaa gag gtt gtg    2644
Lys Asn Leu Glu Leu Gly Lys Ile Met Asp Arg Phe Glu Glu Val Val
                785                 790                 795 tac cag gcc atg gag gaa gtt cag aag cag aag gaa ctt tcc aaa gct    2692
Tyr Gln Ala Met Glu Glu Val Gln Lys Gln Lys Glu Leu Ser Lys Ala
            800                 805                 810 gaa atc cag aaa gtt cta aaa gaa aaa gac caa ctt acc aca gat ctg    2740
Glu Ile Gln Lys Val Leu Lys Glu Lys Asp Gln Leu Thr Thr Asp Leu
        815                 820                 825 aac tcc atg gag aag tcc ttc tcc gac ctc ttc aag cgt ttt gag aaa    2788
Asn Ser Met Glu Lys Ser Phe Ser Asp Leu Phe Lys Arg Phe Glu Lys
830                 835                 840 cag aaa gag gtg atc gag ggc tac cgc aag aac gaa gag tca ctg aag    2836
Gln Lys Glu Val Ile Glu Gly Tyr Arg Lys Asn Glu Glu Ser Leu Lys
845                 850                 855                 860 aag tgc gtg gag gat tac ctg gca agg atc acc cag gag ggc cag agg    2884
Lys Cys Val Glu Asp Tyr Leu Ala Arg Ile Thr Gln Glu Gly Gln Arg
                865                 870                 875 tac caa gcc ctg aag gcc cac gcg gag gag aag ctg cag ctg gca aac    2932
Tyr Gln Ala Leu Lys Ala His Ala Glu Glu Lys Leu Gln Leu Ala Asn
            880                 885                 890 gag gag atc gcc cag gtc cgg agc aag gcc cag gcg gaa gcg ttg gcc    2980
Glu Glu Ile Ala Gln Val Arg Ser Lys Ala Gln Ala Glu Ala Leu Ala
        895                 900                 905 ctc cag gcc agc ctg agg aag gag cag atg cgc atc cag tcg ctg gag    3028
Leu Gln Ala Ser Leu Arg Lys Glu Gln Met Arg Ile Gln Ser Leu Glu
    910                 915                 920 aag aca gtg gag cag aag act aaa gag aac gag gag ctg acc agg atc    3076
Lys Thr Val Glu Gln Lys Thr Lys Glu Asn Glu Glu Leu Thr Arg Ile
925                 930                 935                 940 tgc gac gac ctc atc tcc aag atg gag aag atc tga cctccacgga         3122
Cys Asp Asp Leu Ile Ser Lys Met Glu Lys Ile
                945                 950 gccgctgtcc cgccccccct gctccgtct gtcgtcctg tctgattctc ttaggtgtca   3182
tgttcttttt tctgtcttgt cttcaacttt tttaaaaact agattgcttt gaaaacatga 3242 ctcaataaaa gtttcctttc aatttaaa                                    3270

<210> SEQ ID NO 6
<211> LENGTH: 951
<212> TYPE: PRT
<213> ORGANISM: Homo sapiens

<400> SEQUENCE: 6

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60
```

-continued

```
Gly Gly Gly Pro Met Gly Pro Thr Val Trp Val Lys Asp Gly Thr Gly
 65                  70                  75                  80

Leu Val Pro Ser Glu Arg Val Leu Val Gly Pro Gln Arg Leu Gln Val
                 85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Glu Leu Val Glu Ala
        355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
```

```
                485                 490                 495
Asp Lys Asp Arg Ala Lys Pro Val Thr Val Ala Val Lys Met Leu
            500                 505                 510

Lys Asp Asp Ala Thr Asp Lys Asp Leu Ser Asp Leu Val Ser Glu Met
            515                 520                 525

Glu Met Met Lys Met Ile Gly Lys His Lys Asn Ile Ile Asn Leu Leu
        530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
        610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
        690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Val Lys Ala Thr Gln Glu Glu Asn
        755                 760                 765

Arg Glu Leu Arg Ser Arg Cys Glu Glu Leu His Gly Lys Asn Leu Glu
        770                 775                 780

Leu Gly Lys Ile Met Asp Arg Phe Glu Val Val Tyr Gln Ala Met Glu
785                 790                 795                 800

Glu Val Gln Lys Gln Lys Glu Leu Ser Lys Ala Glu Ile Gln Lys
                805                 810                 815

Val Leu Lys Glu Lys Asp Gln Leu Thr Thr Asp Leu Asn Ser Met Glu
            820                 825                 830

Lys Ser Phe Ser Asp Leu Phe Lys Arg Phe Glu Lys Gln Lys Glu Val
        835                 840                 845

Ile Glu Gly Tyr Arg Lys Asn Glu Glu Ser Leu Lys Lys Cys Val Glu
        850                 855                 860

Asp Tyr Leu Ala Arg Ile Thr Gln Glu Gly Gln Arg Tyr Gln Ala Leu
865                 870                 875                 880

Lys Ala His Ala Glu Glu Lys Leu Gln Leu Ala Asn Glu Glu Ile Ala
                885                 890                 895

Gln Val Arg Ser Lys Ala Gln Ala Glu Ala Leu Ala Leu Gln Ala Ser
            900                 905                 910
```

```
Leu Arg Lys Glu Gln Met Arg Ile Gln Ser Leu Glu Lys Thr Val Glu
        915                 920                 925

Gln Lys Thr Lys Glu Asn Glu Glu Leu Thr Arg Ile Cys Asp Asp Leu
    930                 935                 940

Ile Ser Lys Met Glu Lys Ile
945                 950

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 7
ctactccttc gacacctgca ag                                              22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: synthetic
      primer

<400> SEQUENCE: 8
ccgtggaggt cagatcttct c                                               21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 9
cactgtctgg gtcaaggatg                                                 20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 10
tccccgtctt cgtcatctc                                                  19

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 11
ctgaaattac gggtacctga ag                                              22

<210> SEQ ID NO 12
<211> LENGTH: 20
<212> TYPE: DNA
```

```
<213> ORGANISM: Artificial Sequence
<220> FEATURE:
<223> OTHER INFORMATION: Description of Artificial Sequence: synthetic
      primer

<400> SEQUENCE: 12
tccgttgtac cagccttttc                                                    20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 13
agcagctcac cttcaaggac ctgg                                               24

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 14
gtgaagatgc tgaaagacga tg                                                 22

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: synthetic
      primer

<400> SEQUENCE: 15
ggtcagctcc tcgttctctt tag                                                23
```